United States Patent [19]
Brown et al.

[11] Patent Number: 5,929,081
[45] Date of Patent: Jul. 27, 1999

[54] METHOD FOR TREATING DISEASES MEDIATED BY CELLULAR PROLIFERATION IN RESPONSE TO PDGF, EGF, FGF AND VEGF

[75] Inventors: Paul A. Brown, Snohomish; Stuart L. Bursten, Snoqualmie; Glenn C. Rice; Jack W. Singer, both of Seattle, all of Wash.

[73] Assignee: Cell Therapeutics Inc., Seattle, Wash.

[21] Appl. No.: 08/485,320

[22] Filed: Jun. 7, 1995

Related U.S. Application Data

[62] Division of application No. 08/181,947, Jan. 14, 1994.

[51] Int. Cl.$^6$ .......................... A61K 31/52; A61K 31/535; A61K 31/51; A61K 31/44
[52] U.S. Cl. .................. 514/263; 514/228.8; 514/229.5; 514/277; 514/300; 514/302
[58] Field of Search ................................ 514/263, 228.8, 514/229.5, 277, 300, 302

[56] References Cited

PUBLICATIONS

Brown et al., *The New England Journal of Medicine*, "Regression of Coronary Artery Disease As A Result of Intensive Lipid–Lowering Therapy In Men With High Levels Of Apolipoprotein B", vol. 323, No. 19, pp. 1289–1298, 1990.

Casscells et al., *Proc. Natl. Acad. Sci. USA*, "Elimination Of Smooth Muscle Cells In Experimental Restenosis: Targeting Of Fibroblast Growth Factor Receptors", vol. 89, pp. 7159–7163, 1992.

Ferns et al., *Science*, "Inhibition Of Neointimal Smooth Muscle Accumulation After Angioplasty By An Antibody To PDGF", vol. 253, pp. 1129–1132, 1991.

Ferrara, et al., *J. Clin. Invest.*, "Expression Of Vascular Endothelial Growth Factor Does Not Promote Transformation But Confers A Growth Advantage In Vivo To Chinese Hamster Ovary Cells", vol. 91, pp. 160–170, 1993.

Fingerle et al., *Proc. Natl. Acad. Sci. USA*, "Rose Of Platelets In Smooth Muscle Cell Proliferation And Migration After Vascular Injury In Rat Carotid Artery", vol. 86, pp. 8412–8416, 1989.

Folkman, et al., *Nature*, "Induction Of Angiogenesis During The Transition From Hyperplasia To Neoplasia", vol. 339, pp. 58–61, 1989.

Harris, Jr., *Arthritis and Rheumatism*, "Recent Insights Into The Pathogenesis Of The Proliferative Lesion In Rheumatoid Arthritis", vol. 19, No. 1, pp. 68–72, 1976.

Hori et al., *Cancer Research*, "Suppression Of Solid Tumor Growth By Immunoneutralizing Monoclonal Antibody Against Human Basic Fibroblast Growth Factor", vol. 51, pp. 6180–6184, 1991.

Kane et al., *JAMA*, "Regression Of Coronary Atherosclerosis During Treatment Of Familial Hypercholesterolemia With Combined Drug Regimens", vol. 264, No. 23, 1990.

Kim et al., *Nature*, "Inhibition Of Vascular Endothelial Growth Factor–Inducted Angiogenesis Suppresses Tumor Growth in vivo", vol. 362, pp. 841–844, 1993.

Lindner et al., *Proc. Natl. Acad. Sci. USA*, "Proliferation Of Smooth Muscle Cells After Vascular Injury Is Inhibited By An Antibody Against Basic Fibroblast Growth Factor", vol. 88, pp. 3739–3743, 1991.

McLeskey et al., *Cancer Research*, "Fibroblast Growth Factor 4 Transfection Of MCF–7 Cells Produces Cell Lines That Are Tumorigenic And Metastatic in Ovariectomized Or Tamoxifen–Treated Athymic Nude Mice", vol. 53, pp. 2168–2177, 1993.

(List continued on next page.)

*Primary Examiner*—Theodore J. Criares
*Attorney, Agent, or Firm*—Stephen Faciszewski

[57] ABSTRACT

There is disclosed a method for:

(1) inhibiting new blood vessel formation that is useful for treating or preventing progression of diabetic retinopathy, cavernous haemangiomas, Kaposi's sarcoma, tumors composed of endothelial-like cells, and growth of cancer cells by preventing their development of a new blood supply;

(2) suppressing development of kidney diseases due to cytokine induced proliferation of mesangial cells and/or glomerular epithelial cells that is useful for treating or preventing progression of diabetic glomerulosclerosis and other glomerulonephritides of various types and etiologies;

(3) preventing joint destruction accompanying rheumatoid arthritis due to proliferation of synovial cells;

(4) suppressing manifestations of psoriasis due to proliferation of keratinocytes and accumulation of inflammatory cells;

(5) suppressing accelerated atherogenesis involved in restenosis of coronary vessels or other arterial vessels following angioplasty;

(6) suppressing atherogenesis, coronary artery disease and other vasculopathies due to atherogenesis; and (7) suppressing tumor growth via paracrine or autocrine mediated responses to PDGF, FGF EGF or VEGF that is useful for treating or preventing progression of tumors such as breast cancer stimulated through overexpression of her-2-neu receptor, wherein the inventive method comprises administering a compound that inhibits signal transduction through cellular accumulation of non-arachidonyl phosphatidic acid (PA) selected from the group consisting of 1-o-octadecanyl 2-oleoyl PA (687), 1-oleoyl 2-linoleoyl PA (697 or 698), 1-o-octadecanyl 2-linoleoyl PA (681), 1-o-octadecanyl-9, 12-dienyl 2-linoleoyl PA (679), 1-myristoyl 2-oleoyl PA (645), 1-o-myristoyl 2-stearoyl PA (633), 1,2-sn-dilinoleoyl PA (695), 1-oleoyl 2-linoleoyl PA (697), 1-stearoyl 2-oleoyl PA (701), 1-o-oleoyl 2-20:4 PA (707), 1-o-linoleoyl 2-20:4 PA (705), 1-o-linoleoyl 2-20:5 PA (703), and combinations thereof.

13 Claims, 30 Drawing Sheets

OTHER PUBLICATIONS

Morisaki et al., *Atherosclerosis*, "Cell Cycle–Dependent Inhibition Of DNA Synthesis By Prostaglandin $I_2$ In Cultured Rabbit Aortic Smooth Muscle Cells", vol. 71, pp. 165–171, 1988.

Nabel et al., *J. Clin. Invest.*, "Recombinant Platelet–Derived Growth Factor B Gene Expression In Porcine Arteries Induces Intimal Hyperplasia In Vivo", vol. 91, pp. 1822–1829, 1993.

Pickering et al., *J. Clin. Invest.*, "Proliferative Activity In Peripheral And Coronary Atherosclerotic Plaque Among Patients Undergoing Percutaneous Revascularization", vol. 91, pp. 1469–1480, 1993.

Popma et al., *Circulation*, "Clinical Trials Of Restenosis After Coronary Angioplasty", vol. 84, No. 3, pp. 1426–1436, 1991.

Ross, *Nature*, "The Pathogenesis Of Atherosclerosis: A Perspective for the 1990s", vol. 362, pp. 801–809, 1993.

Ross et al., *Science*, "Localization Of PDGF–B Protein In Macrophages In All Phases Of Atherogenesis", vol. 248, pp. 1009–1012, 1990.

Sano et al., *J. Clin. Invest.*, "Coexpression Of Phosphotyrosine–Containing Proteins, Platelet–Derived Growth Factor–B, And Fibroblast Growth Factor–1 In Situ In Synovial Tissues Of Patients With Rheumatoid Arthritis And Lewis Rats With Adjuvant Or Streptococcal Cell Wall Arthritis", vol. 91, pp. 553–565, 1993.

Sano et al., *J. Cell Biology*, "Detection Of High Levels Of Heparin Binding Growth Factor–1 (Acidic Fibroblast Growth Factor) In Inflammatory Arthritic Joints", vol. 110, pp. 1417–1426, 1990.

Shimokado et al., *Cell*, "A Signifigant Part Of Macrophage-–Derived Growth Factor Consists Of At Least Two Forms Of PDGF", vol. 43, pp. 277–286, 1985.

Tzeng et al., *Blood*, "Platelet–Derived Growth Factor Promotes Human Peripheral Monocyte Activation", vol. 66, pp. 179–183, 1985.

METHOD FOR TREATING DISEASES MEDIATED BY CELLULAR PROLIFERATION IN RESPONSE TO PDGF, EGF, FGF AND VEGF

This is a Division of U.S. application Ser. No. 08/181,947 filed Jan. 14, 1994.

TECHNICAL FIELD OF THE INVENTION

The present invention provides a method for treating diseases mediated by cellular proliferation in response to platelet derived growth factor (PDGF), fibroblast derived growth factor (FGF), epidermal derived growth factor (EGF) and vascular endothelial growth factor (VEGF), comprising administering an effective amount of a compound that inhibits the intracellular accumulation and activity of a defined group of phosphatidic acid (PA) species in response to PDGF, FGF, EGF or VEGF (or combinations thereof) signaling. The specific anti-proliferative response results in pharmacologic activity useful for treatment or prevention of coronary restenosis, tumor-associated angiogenesis, atherosclerosis, autoimmune diseases, acute inflammation, certain kidney diseases associated with proliferation of glomerular or mesangial cells, and occular diseases associated with retinal vessel proliferation.

BACKGROUND OF THE INVENTION

Atherosclerosis is a principal cause of heart attack, stroke, hypertention and gangrene of the extremities and is (directly or indirectly) responsible for about 50% of all mortality in the United States, Western Europe and Japan (Ross, *Nature* 362:801–809, 1993). Atherosclerosis is a disease characterized by focal thickening of the inner portion of the artery wall, predisposing an individual to myocardial infarction (heart attack), cerebral infarction (stroke), hypertension (high blood pressure) and gangrene of the extremities. A common underlying events responsible for the formation of lesions are the intimal thickening of proliferating smooth muscle cells, probably in response to endothelial cell injury. Accumulation of smooth muscle cells in coronary arteries physically treated by angioplasty or by bypass surgery is also a prominent feature of restenosis. In addition to consisting primarily of proliferated smooth muscle cells, lesions of atherosclerosis are surrounded by large amounts of lipid-laden macrophages, varying numbers of lymphocytes and large amounts of connective tissue. PDGF is considered to be a principal growth-regulatory molecule responsible for smooth muscle cell proliferation. For instance, PDGF, as measured by mRNA analysis as well as in situ staining using an antibody against PDGF, was found within macrophages of all stages of lesion development in both human and nonhuman primate atherosclerosis (Ross et al., *Science*, 248: 1009–1012, 1990). PDGF was found in both non-foam cells and lipid rich macrophage foam cells. These data are consistent with PDGF playing a critical role in the atherosclerosis disease process. In addition, analysis of advanced human lesions examined by atherectomy catheter indicate that atherosclerotic and restenotic lesions contain high levels of PDGF as measured by in situ hybridization.

One of the principal surgical approaches to the treatment of atherosclerosis is transluminal angioplasty, or PCTA. Restenosis is due principally to the accumulation of neointimal smooth muscle cells, which is also a prominent feature of lesions of atherosclerosis. The failure rate due to restenosis after PCTA is 30–50% (Ross, *Nature* 362:801, 1993). Much of the restenosis is due to further inflammation, smooth muscle accumulation and thrombosis. Results from balloon angioplasty of a normal rat carotid artery, an animal model for PCTA, has demonstrated that PDGF and FGF may mediate intimal thickening that forms 7–21 days following injury (Ferns et al., *Science* 253:1129, 1991; Morisaki et al., *Atherosclerosis* 71:165, 1988; and Fingerle et al., *Proc. Natl. Acad. Sci. USA* 86:8412, 1989). Antibodies against bFGF prevented medial smooth muscle replication that occurred 24–48 hr. following injury of medial cells to the inflated balloon (Linder and Reidy, *Proc. Natl. Acad. Sci. USA* 88:3739, 1988). Antibodies against PDGF induced a statistically significant diminution in the neointimal accumulation of smooth muscle cells that resulted 3–6 days after ballooning (Ferns et al., *Science* 253:1129, 1991). Thus, similar growth factors are probably involved in both restenosis and atherogenesis. Inhibition of proliferative responses of these growth factors to smooth muscle cells can abrogate the diseases in animal models.

Restenosis is primarily due to proliferation of the neointimal smooth muscle cells rather than simple chemotaxis of smooth muscle cells. Pickering et al. (*J. Clin. Invest.* 91:1469–1480 1993) have shown in situ evidence of underlying proliferating smooth muscle cells in 11 of 11 restenotic lesions isolated from humans that had underwent angioplasty. The percentage of proliferating cells in some of the lesions approximated those found in human tumors and were observed up to 1 year following angioplasty. Further evidence that PDGF can play a role in arterial lesions was provided by Nabel et al. (*J. Clin. Invest* 91:1822–1829 1993) who showed that intimal thickening could be induced in porcine iliofemoral arteries by direct transfection and expression of a gene encoding PDGF. Thus, these data show that expression of PDGF within arteries in vivo can cause intimal hyperplasia and induce lesions relevant to pathogenesis of atherosclerosis and restenosis.

Occlusive lesions of atherosclerosis in humans can be reversed with aggressive treatment with lipid-lowering drugs (Brown et al., *N. Engl. J. Med.* 323:1289, 1990; and Kane et al., *J. Am. Med. Assoc.,* 264:3007, 1990). Current therapies for inhibition of restenotic lesions are more limited, involving anticoagulants, steroids, fish oil with omega-3 fatty acids, anti-platelet therapies, and cytotoxic drugs, all with questionable benefit (Pompa et al., *Circulation* 84:1426, 1991). Other therapies have been tried in predictive in vivo models, including, for example, antibodies to FGF and PDGF, and conjugates of saporin and FGF (Casscells et al., *Proc. Natl. Acad Sci. USA* 89:7159–7163 1992).

Aberrant overexpression of FGF and PDGF has been found in synovial tissues from patients with rheumatoid arthritis. Overexpression was also found in various animal models of arthritis. These data implicate FGF and PDGF in inflammatory joint disease. RA is characterized by diffuse and nodular mononuclear cell infiltration and massive hyperplasia of the stromal connective tissues, comprised of fibroblast-like cells and new blood vessels. The highly invasive lesions resembles a localized nonmetastatic invasive neoplasm (Harris, *Arthritis Rheum.* 19:68–72, 1976). FGF directly stimulates angiogenesis in vivo. Both PDGF and FGF are mitogenic agents for synovial fibroblasts. Furthermore, PDGF can, in part, be produced by infiltrating monocytes, seen early in the pathogenesis of RA (Shimokado et al., *Cell* 43:277–286, 1985). In addition, PDGF can directly activate both neutrophils and monocytes, including release of superoxide, release of granule enzymes, and increased cell adherence and aggregation. These data suggest that PDGF is an important mediator of inflammatory responses in general (Tzeng et al., *Blood,* 66:179–183 1985).

Synovial tissues of RA patients express high levels of FGF and PDGF compared with synovial tissues of osteoarthritis patients, a non invasive joint disease (Sano et al., *J. Cell. Biol.* 110:1417–1426, 1990). These data are consistent with the theory that PDGF and FGF play a role in generating an invasive tumor-like behavior in arthritic joints of RA synovial connective tissues (Sano et al., *J. Clin. Invest.* 91:553–565 1993). Thus, there is a need in the art to develop an agent that can inhibit PDGF and FGF signaling of cellular activation and proliferation of synovial fibroblasts, activation of migration of PMN and monocytes. Such agents are useful agents for the treatment or prevention of progression of RA and other inflammatory-disease states involving monocytes, PMNs or platelets.

Neovascularization is critical for the growth for tumors and is important in a variety of angiogenic diseases, such as diabetic retinopathy, arthritis, psoriasis and haemangiomas. More than 70% of cancer patients die from metastatic dissemination of the initial tumor. Tumor neovascularization is the crucial process for survival of a primary tumor and for metastatic dissemination. Angiostatic steroids and heparin with anti-angiogenic agents such as protamin have been used as therapies to suppress tumor growth. These therapeutic approaches have serious limitations, because when the dose of heparin exceeded an optimum level for inhibition of angiogenesis, both tumor growth and angiogenesis were stimulated. Also, high doses of cortisone that are required for antiangiogenesis led to immunosuppression. Acquisition of an angiogenic phenotype marked a transition from hyperplasia to neoplasia (Folkman et al., *Nature*, 339:58–60 1989).

Both FGF and VEGF are potent angiogenic factors which induce formation of new capillary blood vessels. Transfection of human breast carcinoma cell line MCF-7 with FGF resulted in cell lines that form progressively growing and metastatic tumors when injected (s.c.) into nude mice. FGF may play a critical role in progression of breast tumors to an estrogen-independent, anti-estrogen resistant metastatic phenotype (McLeskey et al., *Cancer Res.* 53:2168–2177 1993). Breast tumor cells exhibited increased neovascularization, increased spontaneous metastasis and more rapid growth in vivo than did the non-transfected tumors. FGF has been shown to be transforming in NIH-3T3 cells and implicated in tumorigenesis and metastasis of mouse mammary tumors. FGF overexpression conferred a tumorigenic phenotype on a human adrenal carcinoma cell line suggesting that FGF's may also play a role in the transformation of epithelial cells. Polyclonal neutralizing antibodies to FGF inhibited tumor growth in Balb/c nude mice transplanted with K1000 cells (transfected with the leader sequence of bFGF) which form tumors in these mice (Hori et al., *Cancer Res.* 51:6180–9184 1991). Due to a role of FGF in neovascularization, tumorigenesis and metastasis there is a need in the art for FGF inhibitors as potent anti-cancer agents that exert their anti-FGF activity by preventing intracellular signaling of FGF.

VEGF is an endothelial cell-specific mitogen and an angiogenesis inducer that is released by a variety of tumor cells and expressed in human tumor cells in situ. Unlike FGF, transfection of cell lines with a cDNA sequence encoding VEGF, did not promote transformation, but did facilitate tumor growth in vivo (Ferrara et al., *J Clin. Invest.* 91:160–170 1993). This was likely due to paracrine stimulation of neovasculagenesis Furthermore, administration of polyclonal antibody which neutralize VEGF inhibited growth of human rhabdomyosarcoma, glioblastoma multiforme and leiomyosarcoma cell lines in nude mice (Kim et al., *Nature* 362:841–843 1993.)

Therefore, there is a need in the art to develop small molecule antagonists of PDGF, FGF, EGF and VEGF individually or as a group. Moreover, if these cytokines signal through a common second messenger pathway within the cell, such antagonists will have broad therapeutic activity to treat or prevent the progression of a broad array of diseases, such as coronary restenosis, tumor-associated angiogenesis, atherosclerosis, autoimmune diseases, acute inflammation, certain kidney diseases associated with proliferation of glomerular or mesangial cells, and occular diseases associated with retinal vessel proliferation. The present invention was made by discovering a common signaling mechanism, a group of active therapeutic agents, shown to be active by a large number of and variety of predictive assays, and discovering a common intracellular signaling intermediate.

SUMMARY OF THE INVENTION

The present invention provides a method for:

(1) inhibiting new blood vessel formation that is useful for treating or preventing progression of diabetic retinopathy, cavernous haemangiomas, Kaposi's sarcoma, tumors composed of endothelial-like cells, and growth of cancer cells by preventing their development of a new blood supply:

(2) suppressing development of kidney diseases due to cytokine induced proliferation of mesangial cells and/or glomerular epithelial cells that is useful for treating or preventing progression of diabetic glomerulosclerosis and other glomerulonephritides of various types and etiologies;

(3) preventing joint destruction accompanying rheumatoid arthritis due to proliferation of synovial cells;

(4) suppressing manifestations of psoriasis due to proliferation of keratinocytes and accumulation of inflammatory cells;

(5) suppressing accelerated atherogenesis involved in restenosis of coronary vessels or other arterial vessels following angioplasty;

(6) suppressing atherogenesis, coronary artery disease and other vasculopathies due to atherogenesis; and (7) suppressing tumor growth via paracrine or autocrine mediated responses to PDGF, FGF, EGF or VEGF that is useful for treating or preventing progression of tumors such as breast cancer stimulated through overexpression of her-2-neu receptor, wherein the inventive method comprises administering a compound that inhibits signal transduction through cellular accumulation of and activity of a non-arachidonyl phosphatidic acid (PA) selected from the group consisting of 1-o-octadecanyl 2-oleoyl PA (687), 1-oleoyl 2-linoleoyl PA (697 or 698), 1-o-octadecanyl 2-linoleoyl PA (681), 1-o-octadecanyl-9,12-dienyl 2-linoleoyl PA (679), 1-myristoyl 2-oleoyl PA (645), 1-o-myristoyl 2-stearoyl PA (633), 1,2-sn-dilinoleoyl PA (695), 1-oleoyl 2-linoleoyl PA (697), 1-stearoyl 2-oleoyl PA (701), 1-o-oleoyl 2-20:4 PA (707), 1-o-linoleoyl 2-20:4 PA (705), 1-o-linoleoyl 2-20:5 PA (703), and combinations thereof. The numbers in parens next to each PA species show the approximate molecular weight of the PA species as seen by mass spectroscopy analysis. More specifically, compounds comprise compounds and pharmaceutical compositions having the formula:

(X)j-(core moiety), wherein j is an integer from one to three, the core moiety comprises at least one five to seven-membered ring or an open chain analog of such a ring group and X is a racemate mixture or R or S enantiomer of:

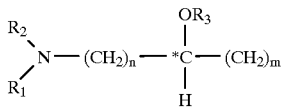

wherein *C is a chiral carbon atom; n is an integer from one to four; one or more carbon atoms of $(CH_2)_n$ may be substituted by a keto or hydroxy group; m is an integer from one to fourteen; independently, $R_1$ and $R_2$ are hydrogen, a straight or branched chain alkane or alkene of up to twelve carbon atoms in length, or $-(CH_2)_W R_5$, w being an integer from two to fourteen and $R_5$ being a mono-, di- or tri-substituted or unsubstituted aryl group, substituents on $R_5$ being selected from the group consisting of hydroxy, chloro, fluoro, bromo, or $C_{1-6}$ alkoxy; or jointly, $R_1$ and $R_2$ form a substituted or unsubstituted, saturated or unsaturated heterocyclic group having from four to eight carbon atoms, N being a hetero atom; and $R_3$ is hydrogen or $C_{1-3}$; or

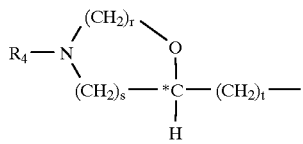

wherein $R_4$ is a hydrogen, a straight or branched chain alkane or alkene of up to eight carbon atoms in length, $-(CH_2)_w R_5$, w being an integer from two to fourteen and $R_5$ being a mono-, di- or tri-substituted or unsubstituted aryl group, substituents on $R_5$ being selected from the group consisting of hydroxy, chloro, fluoro, bromo, or alkoxy $C_{1-6}$ alkoxy, or a substituted or unsubstituted, saturated or unsaturated heterocyclic group having from four to eight carbon atoms, N being a hetero atom; r and s are independently integers from one to four; the sum (r+s) is not greater than five; t is an integer from one to fourteen; and one or more carbon atoms of $(CH_2)_s$ or $(CH_2)_t$ may be substituted by a keto or hydroxy group, or X is independently a resolved enantiomer ω-1 secondary alcohol-substituted alkyl $(C_{5-8})$ substantially free of the other enantiomer, or X is a branched $-(CH_2)_a-CHR_6-(CH_2)_b-R_7$, wherein a is an integer from about 4 to about 12, b is an integer from 0 to 4, $R_6$ is an enantiomer (R or S) or racemic mixture $(C_{1-6})$ alkyl or alkenyl, and $R_7$ is a hydroxy, keto, cyano, chloro, iodo, flouro, or chloro group.

Preferably, the core moiety has from one to three, five to six-membered ring structures in a predominantly planar configuration. Preferably, the amino alcohol substituent (X) is bonded to a ring nitrogen if one exists. For example, the core moiety may be selected from the group consisting of substituted or unsubstituted barbituric acid; benzamide; benzene; cyclohexanedione; cyclopentanedione; delta-lactam; flutarimide; glutarimide; homophthalimide; imidazole amide; isocarbostyrile; lumazine; napthlalene; pthalimide; piperidine; pyridine; pyrimidine; pyrrole amide; quinazolinedione; quinazolinone; quinolone; recorsinol; succinimide; thymine; triazine; uracil or xanthine. Preferred cores include substituted or unsubstituted xanthine, more preferably halogen-substituted xanthine. Exemplary preferred cores include, but are not limited to: 1,3-cyclohexanedione, 1,3-cyclopentanedione; 1,3-dihydroxynaphthalene; 1-methyllumazine; methylbarbituric acid; 3,3-dimethylflutarimide; 2-hydroxypyridine; methyldihydroxy-pyrazolopyrimidine (preferably, 1,3-dimethyldihydroxypyrazolo[4,3-d] pyrimidine); methylpyrrolopyrimidine (preferably, 1-methylpyrrolo [2,3-d] pyrimidine); 2-pyrrole amides; 3-pyrrole amides; 1,2,3, 4-tetrahydroisoquinolone; 1-methyl-2,4(1H,3H) quinazolinedione (1-methylbenzoyleneurea); quinazolin-4 (3H)-one; alkyl-substituted $(C_{1-6})$thymine; methylthymine; alkyl-substituted $(C_{1-6})$ uracil; 6-aminouracil; 1-methyl-5,6-dihydrouracil; 1-methyluracil; 5- and/or 6-position substituted uracils; 1,7-dimethylxanthine, 3,7-dimethylxanthine; 3-methylxanthine; 3-methyl-7-methylpivaloylxanthine; 8-amino-3-methylxanthine; and 7-methylhypoxanthine. Alternatively, the compound is a resolved R or S (preferably R) enantiomer of an ω-1 alcohol of a straight chain alkyl $(C_{5-8})$ substituted at the 1-position of 3,7-disubstituted xanthine. Preferably, the amino alcohol substituent (X) is bonded to a ring nitrogen if one exists. For example, the core moiety is selected from the group consisting of xanthine, halogen-substituted xanthines, 3,7-dimethylxanthine, 3-methylxanthine, 3-methyl-7-methylpivaloylxanthine, 8-amino-3-methylxanthine, 7-methylhypoxanthine, 1-methyluracil, 1-methylthymine, 1-methyl-5,6-dihydrouracil, glutarimides, phthalimide, 1-methyl-2,4(1H, 3H)-quinazolinedione (1-methylbenzoyleneurea), 6-aminouracil, homophthalimide, succinimide, 1,3-cyclohexanedione, resorcinol, 1,3-dihydroxynaphthalene, 1,3-cyclopentanedione, 1,3-dimethyldihydroxypyrazolo[4, 3-d] pyrimidine, 5-substituted uracils, 6-substituted uracils, 1-methylpyrrolo [2,3-d] pyrimidine, 1-methyllumazine, imidazole amides, 2-pyrrole amides, 3-pyrrole amides, benzamides, methylbarbituric acid, benzene, piperdine, delta-lactam, 2-hydroxypyridine, 1,2,3,4-tetrahydroisoquinolone, isocarbostyril, and quinazolin-4 (3H)-one. Most preferably, the core moiety is a substituted xanthine, such as a 3,7 dimethylxanthine. The core moiety can also include a non-cyclic group. Examples of non-cyclic core groups include open chain analogs of glutarimide, carboxilic acid, a hydroxyl group, sulfone, sulfonate, and the like. Examples of compounds with demonstrated activity include compounds selected from the group consisting of R-1-(5-hydroxyhexyl)-3,7-dimethylxanthine, N-(11-octylamino-10-hydroxyundecyl)-homophthalimide, N-(11-octylamino-10-hydroxyundecyl)-3-methylxanthine, N-(11-octylamino-10-hydroxyundecyl)-2-piperdone, 3-(11-octylamino-10 -hydroxyundecyl-1-methyluracil,3-(11-octylamino-10-hydroxyundecyl)-1-methyldihydrouracil, 1-(9-dodecylamino-8-hydroxynonyl)-3,7-dimethyxanthine, 1-(11-hexylamino-8-hydroxyundecyl)-3,7-dimethylxanthine, N-(11-phenylamino-10-hydroxundecyl)-3,7-dimethylxanthine, 1(9(2-hydroxydecyl-1-amino)nonyl)-3,7-dimethylxanthine, and combinations thereof.

Preferably, the core moiety is a member selected from the group consisting of substituted or unsubstituted: barbituric acid; benzamide; benzene; biphenyl; cyclohexanedione; cyclopentanedione; delta-lactam; flutarimide; glutarimide; homophthalimide; imidazole amide; isocarbostyrile; lumazine; napthlalene; pteridine; pthalimide; piperidine; pyridine; pyrimidine; pyrrole amide; quinazolinedione; quinazolinone; quinolone; recorsinol; stilbene; succinimide; theobromine; thymine; triazine; tricyclododecane; uracil and xanthine.

BRIEF DESCRIPTION OF THE DRAWINGS

As seen in FIG. 6, the drug inhibited VEGF-induced proliferation in these cells. This is a predictive model for angiogenesis.

As seen in FIG. 7, the compounds inhibited VEGF-induced proliferation in these cells. This is a predictive model for angiogenesis.

As seen in FIG. 8, all of the compounds inhibited EGF-induced proliferation in a dose-dependent manner, with CT-2510 being the least potent of the compounds tested. These data show that the compounds tested block EGF-mediated proliferative activity which is an important determinant in inflammation, cancer cell growth and metastasis.

However, CT-3501 had a minimal effect on serum induced proliferation. Cells were rested overnight and then pre incubated for 1 hr with CT-3501, incubated with PDGFBB. Tritiated-thymidine was added for 24 hours. The cells were harvested and counted using a liquid scintillation counter as a measure of proliferation. This is a predictive model for restenosis and other proliferative disease states associated with PDGF. These data indicate that PDGF proliferative responses are blocked by CT-3501.

Figure 14A:
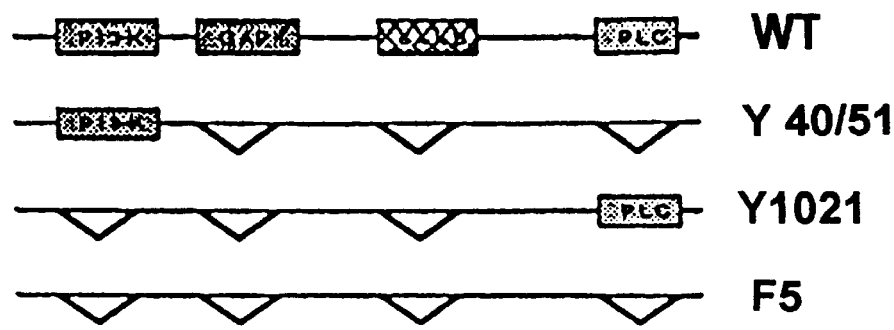
Figure 14B:
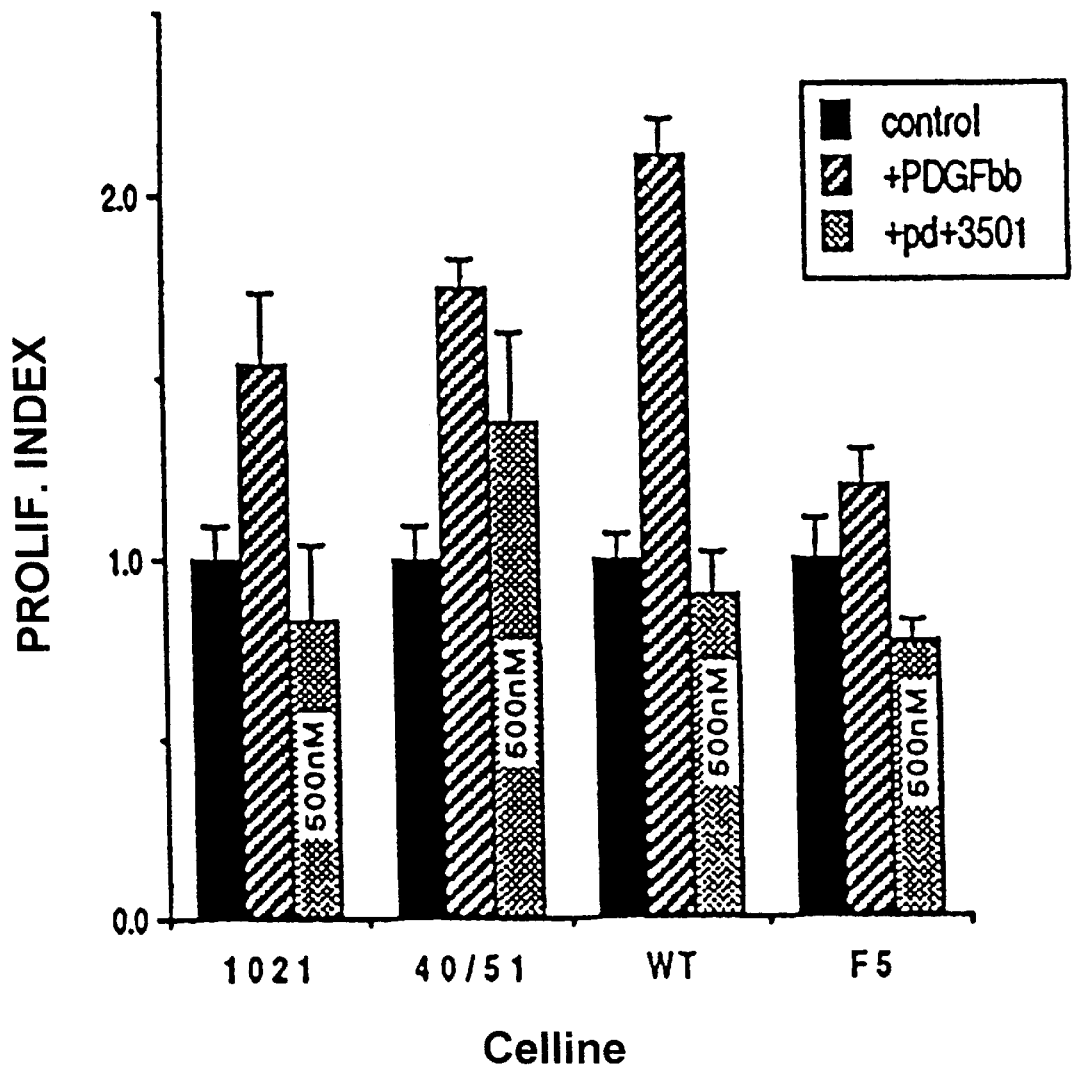

FIG. 14 illustrates data from an experiment showing that compound CT-3501 blocked a PDGF-induced proliferative signal in HepG2 cells transfected with portions of the PDGF receptor shown in the panel on the left. Cells transfected with receptor capable of binding phospholipase c gamma or phosphotidylinositol-3-kinase only were inhibited by CT-3501 (500 nM).

Figure 15:
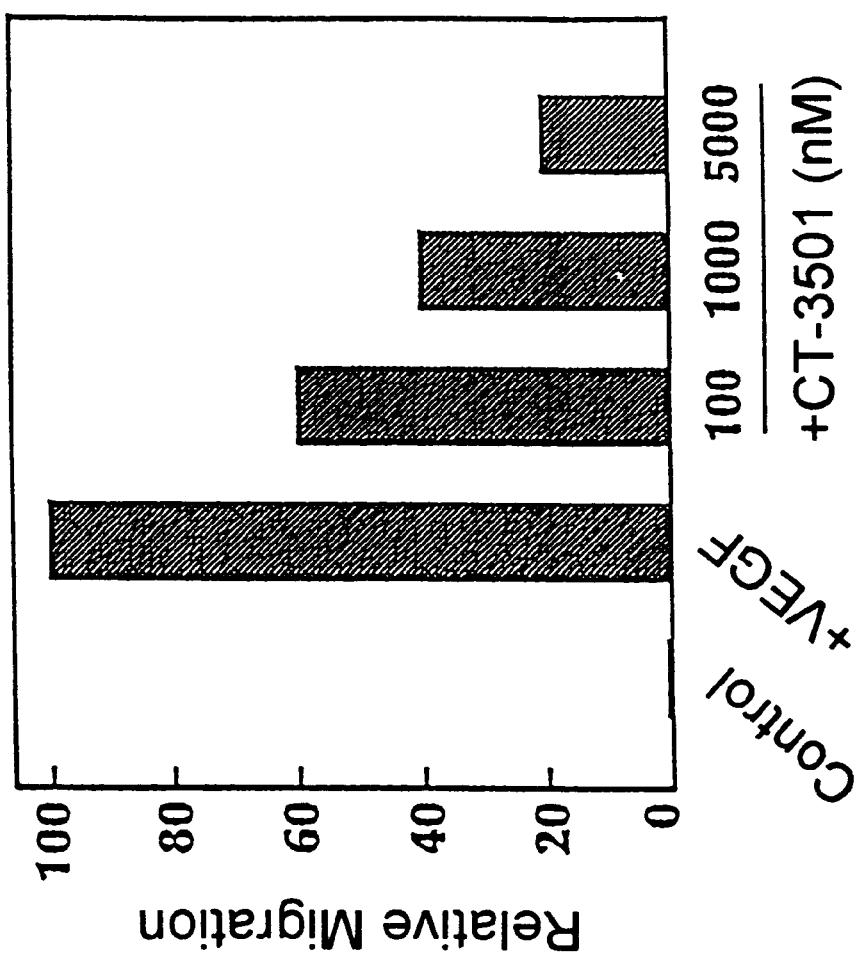
Figure 16A:
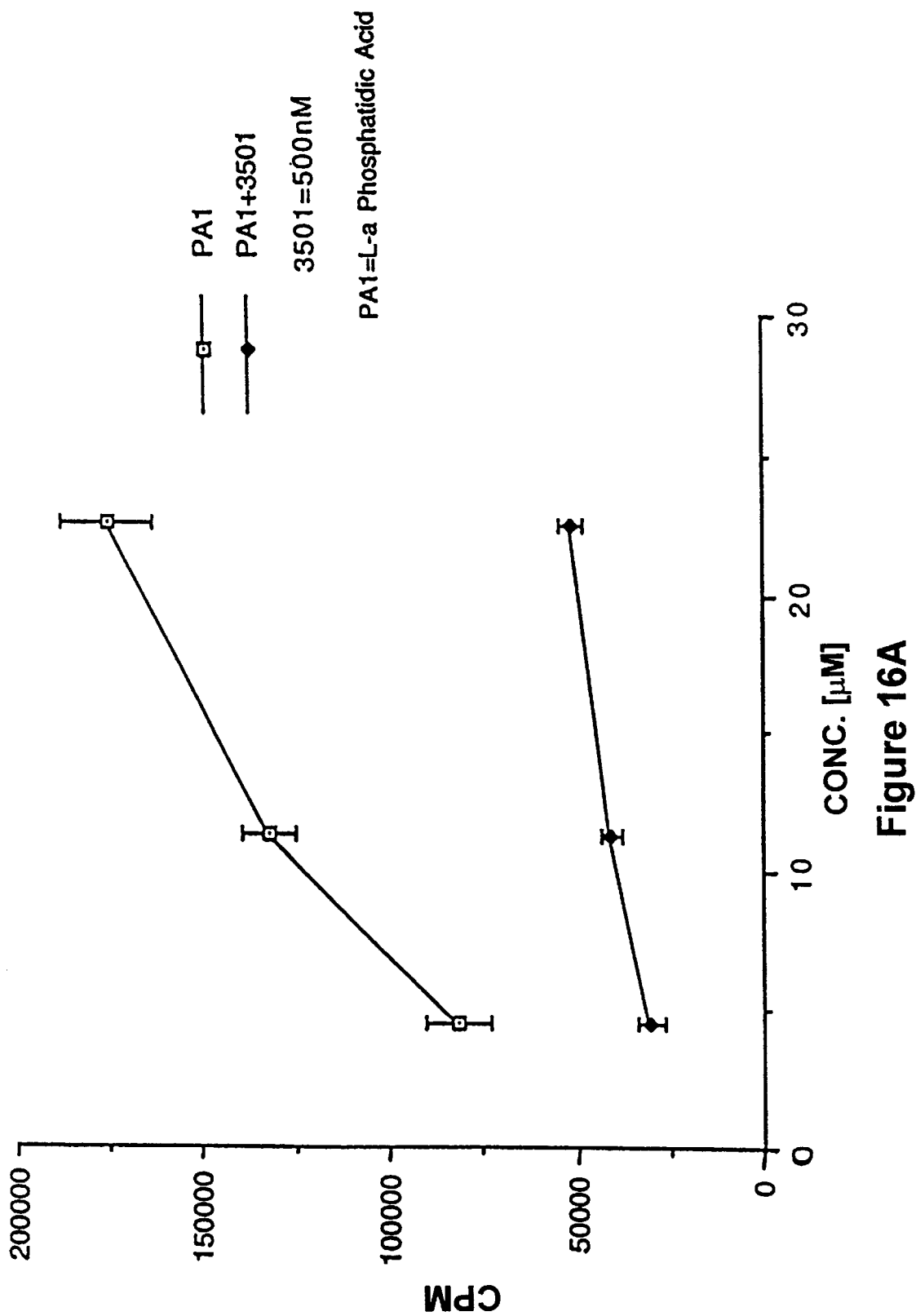
Figure 16B:
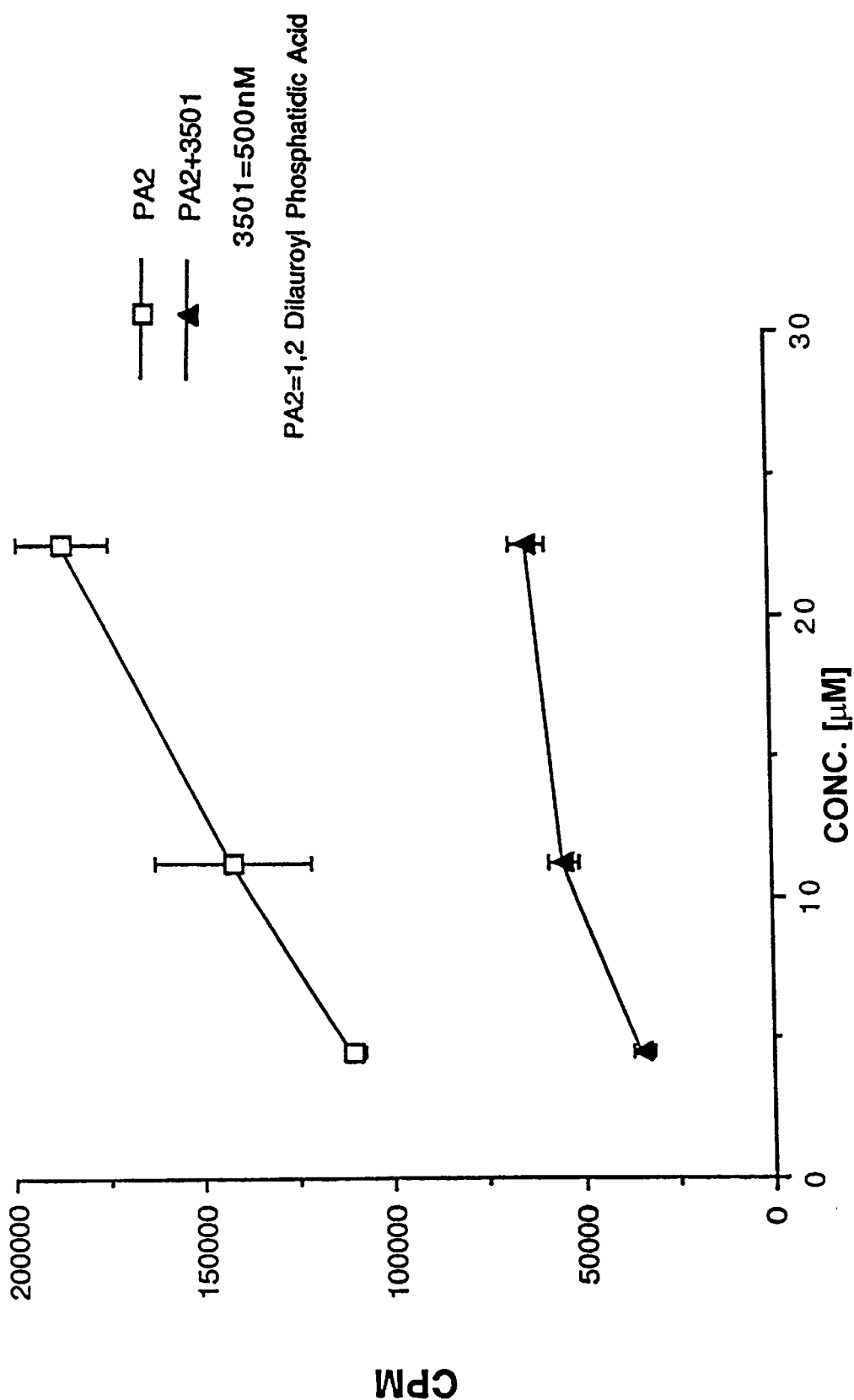
Figure 16C:
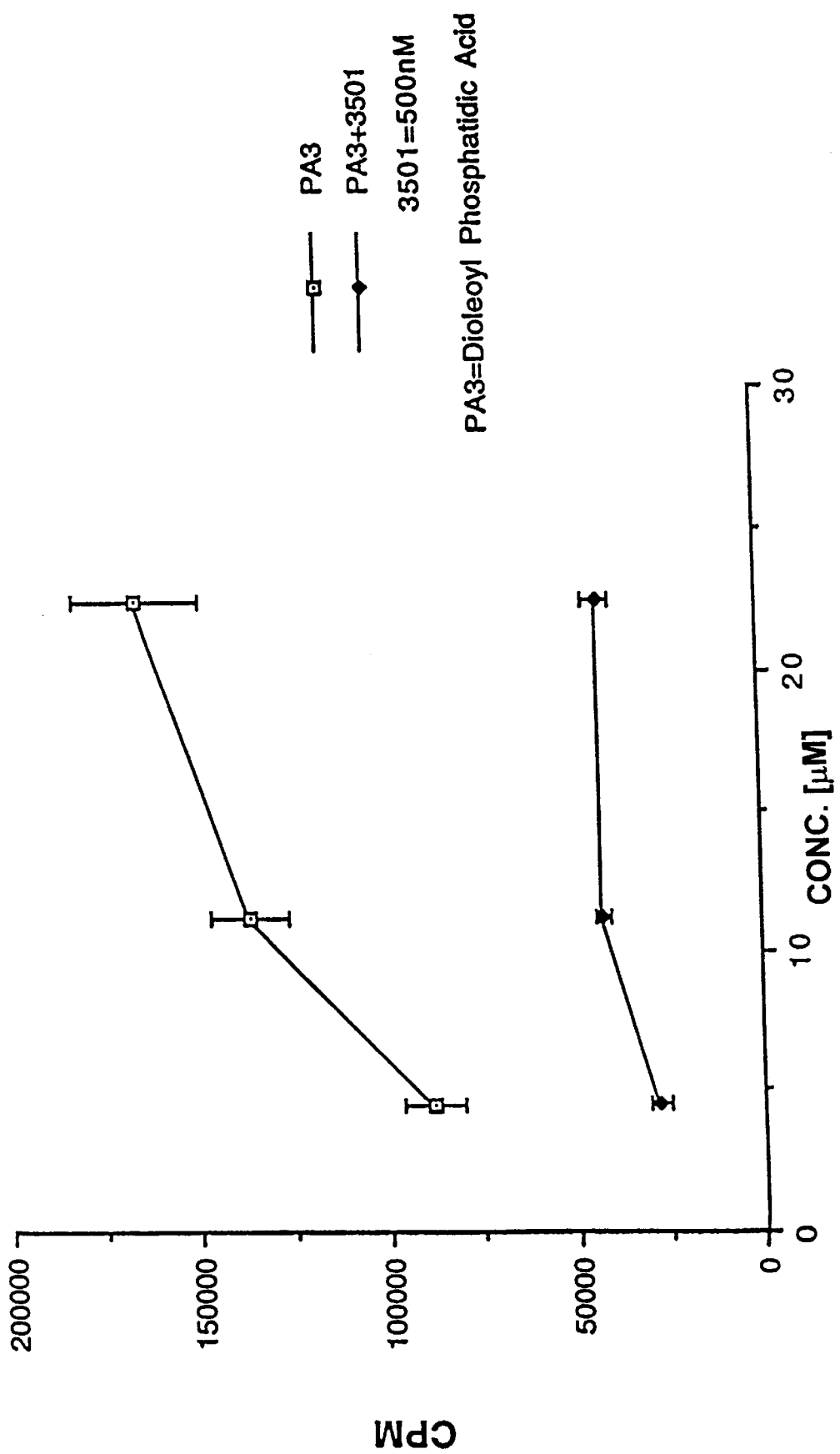
Figure 16D:
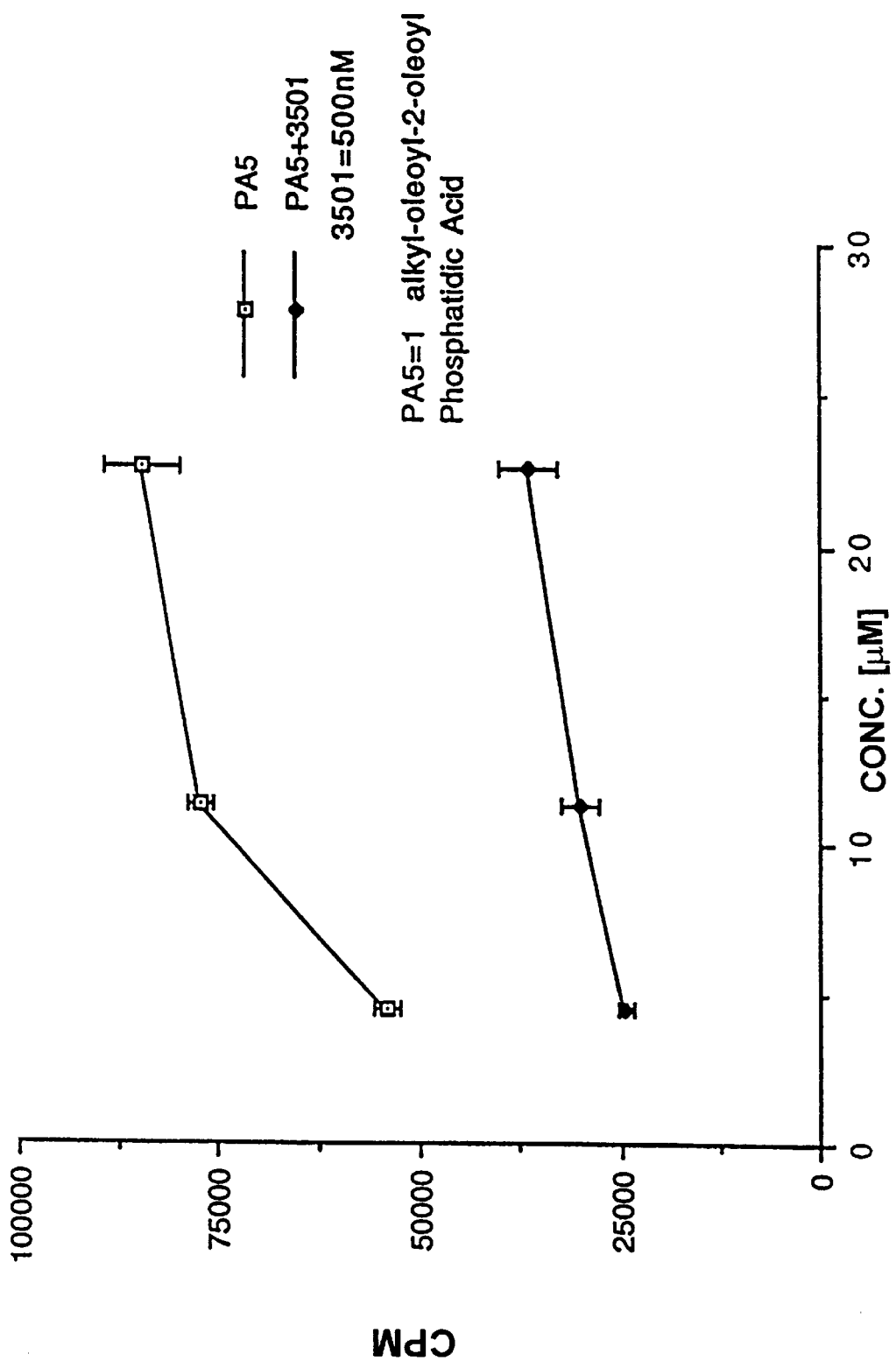
Figure 16E:
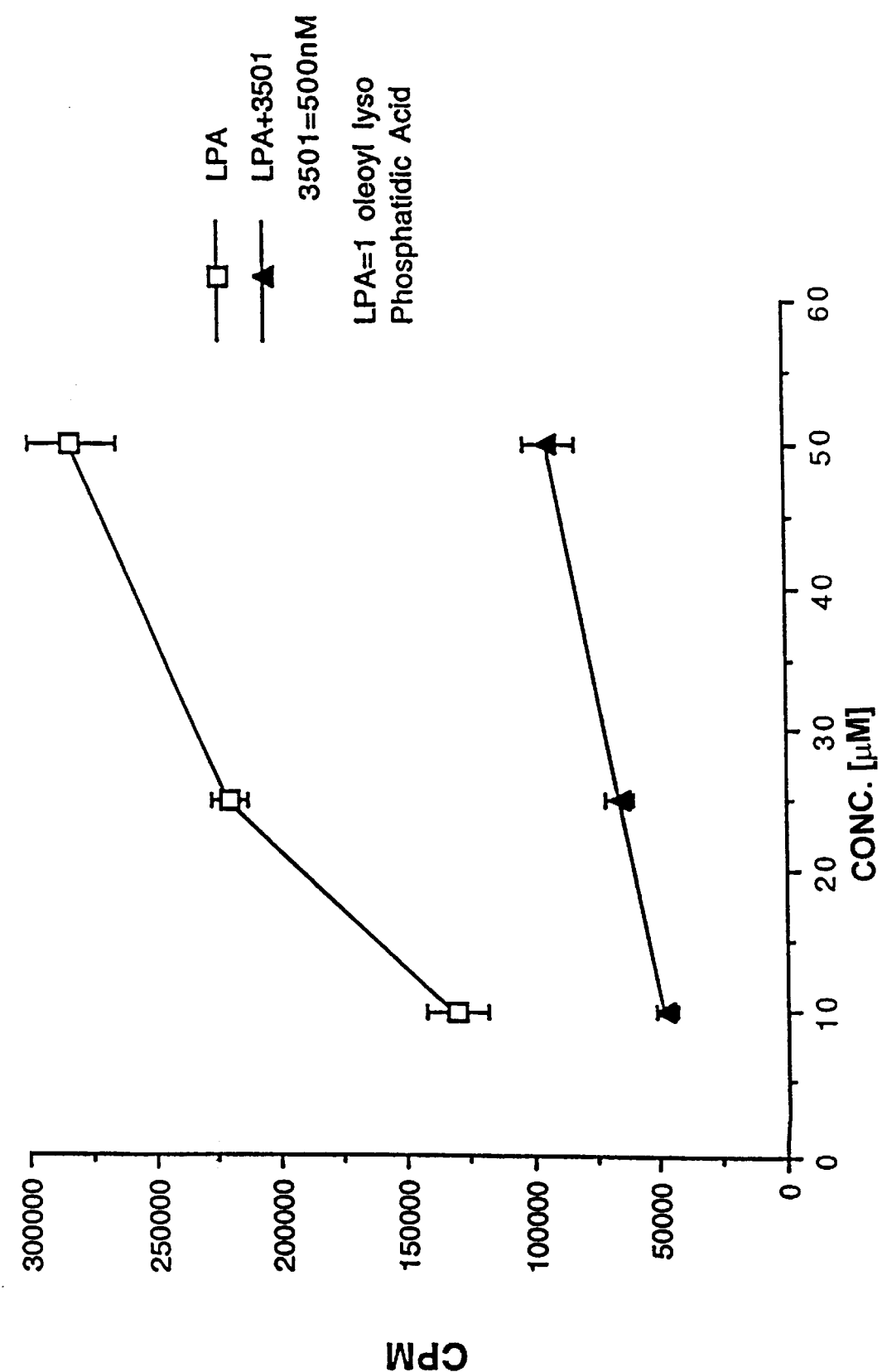

FIG. 15 illustrates a comparison CT-3501 inhibiting invasiveness of 3LL cells (left panel) and VEGF-induced migration of HUVEC's with three dose levels of CT-3501. Cells were placed into a Matrigel invasion assay system (Becton Dickinson, Bedford, Mass.) and assessed for invasiveness (3LL cells) or VEGF induced migration (HUVEC's) with or without CT-3501 after 48 hours. CT-3501 decreased invasiveness at a concentration of 5 $\mu$M and inhibited VEGF-induced migration in a dose-response manner. These data indicate that CT-3501 will block VEGF-mediated proliferative events which have been associated with cancer cell metastasis, invasiveness and angiogenesis.

FIGS. 16a–e illustrates that various species of PA and lyso-Phosphatidic acid induced Balb/3T3 cells to proliferate and that this proliferation is inhibited by CT-3501 at a concentration of 500 nM. The various species of PA are indicated on each figure. As shown in FIGS. 16a–e, addition of various types of PA's, including L-a PA (derived from natural sources), 1,2 dilauroyl-sn-glycero-3-phosphate, 1,2 dioleoyl-sn-glycero-3-phosphate, 1-oleoyl lysoPA and 1-alkyl-oleoyl-2-oleoyl-PA, were mitogenic in Balb/3T3 cells. All of the mitogenic responses induced through the addition of these PA's to the cells were inhibited by CT-3501. Thus, CT-3501 inhibits formation and activity of specific PA species.

Figure 17A:
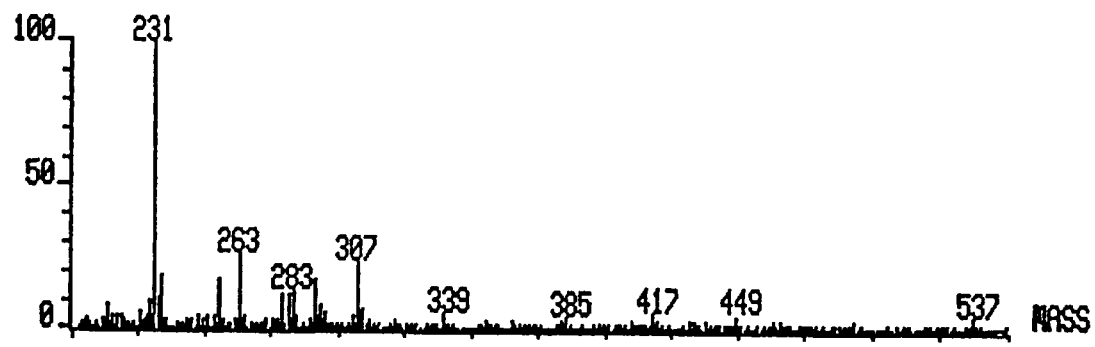
Figure 17B:
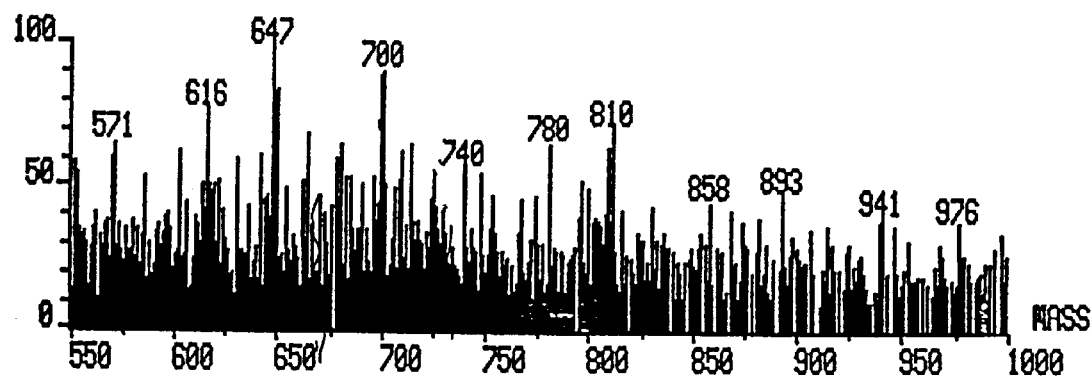
Figure 18A:
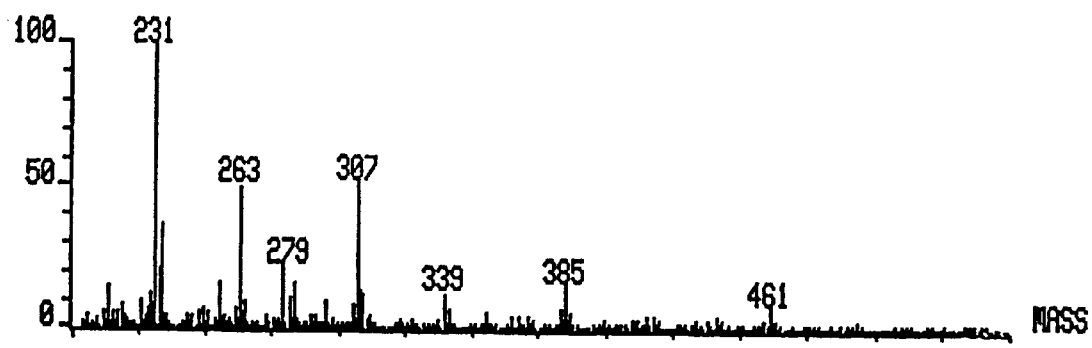
Figure 18B:
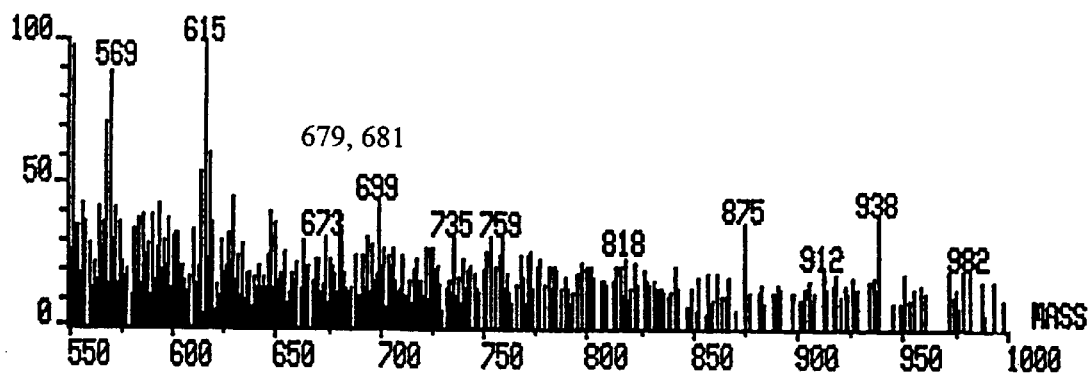
Figure 19A:
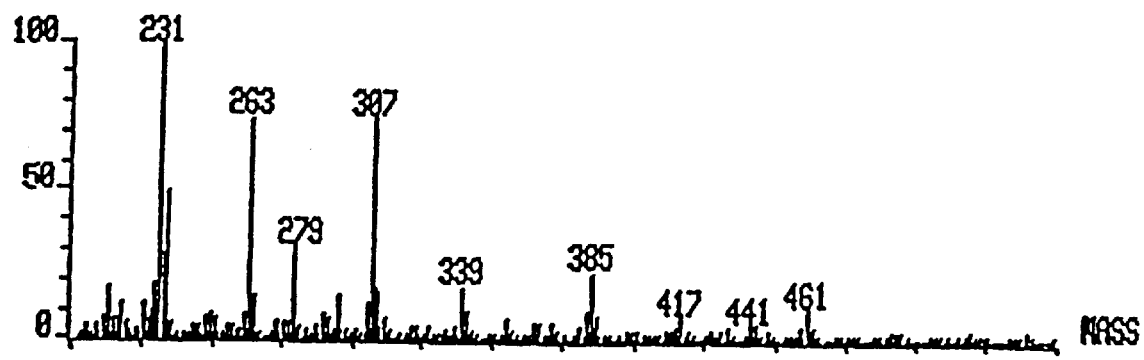
Figure 19B:
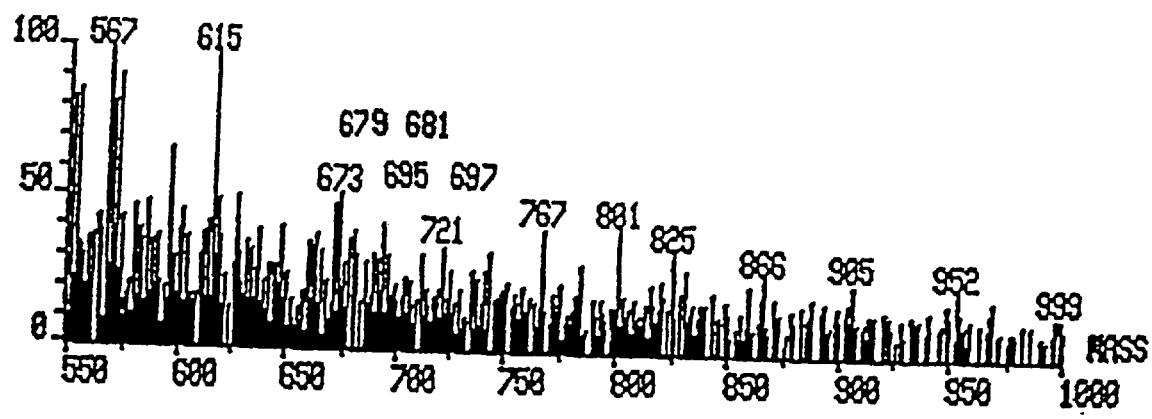

FIGS. 17–21 illustrate a mass spectrograph of a designated lipid fraction isolated from Balb 3T3 fibroblasts stimulated with PDGF (25 ng/ml) in the presence or absence of compound CT-3501. Specifically, FIG. 17 shows a mass spec of a PA HPLC peak 5 seconds after stimulation with PDGF including the 1-o-alkyl C18 PA derivatives including 697 (1-o-'en-octadeca-9,12-dienyl 2 linoleoyl PA), 681 (1-o-octadeca-9,12-dienyl 2-linoleoyl PA), 683 (1-o-octadeca-9-enyl 2-linoleoyl 2-stearoyl PA), and related PA derivatives with C20 sn-2 components such as 703 (1-o-octadeca-9,12-dienyl 2-arachidonoyl PA), and 707 (1-o-octadeca-9-enyl 2-arachidonoyl PA). FIG. 18 shows that synthesis of Type 1B PA species (especially 679 and 681) was maintained after 15 seconds of stimulation with PDGF. Type 1B PA species include, for example, 1-o-octadecanyl 2-oleoyl PA (687), 1-oleoyl 2-linoleoyl PA (697 or 698), 1-o-octadecanyl 2-linoleoyl PA (681), 1-o-octadecanyl-9,12-dienyl 2-linoleoyl PA (679), 1-myristoyl 2-oleoyl PA (645), and 1-o-myristoyl 2-stearoyl PA (633) PA species. FIG. 19 further shows the 15 second stimulation maintaining the Type 1B PA species and, in addition, 673 (1-palmitoyl, 2-oleoyl PA) and 671 (1-palmitoyl, 2-linoleoyl PA) PA species.

Figure 20A:
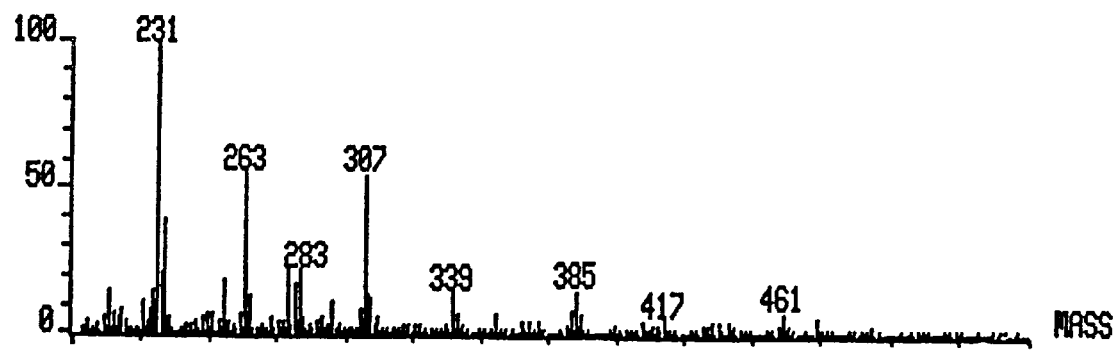
Figure 20B:
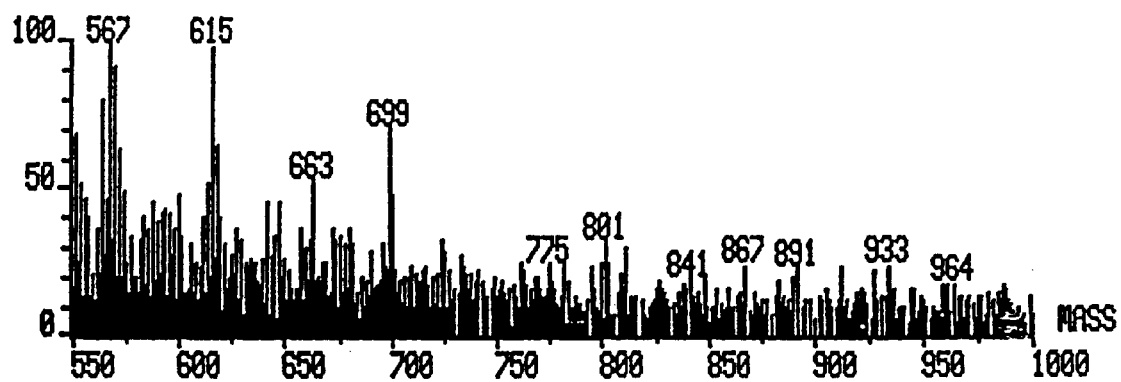
Figure 21A:
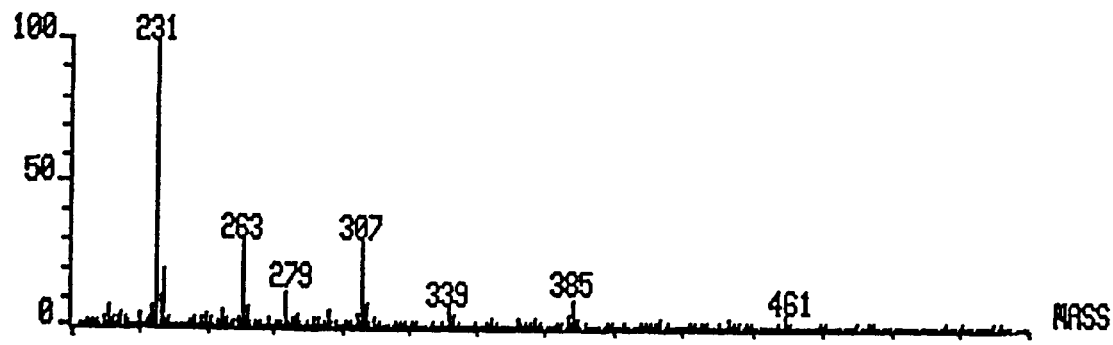
Figure 21B:
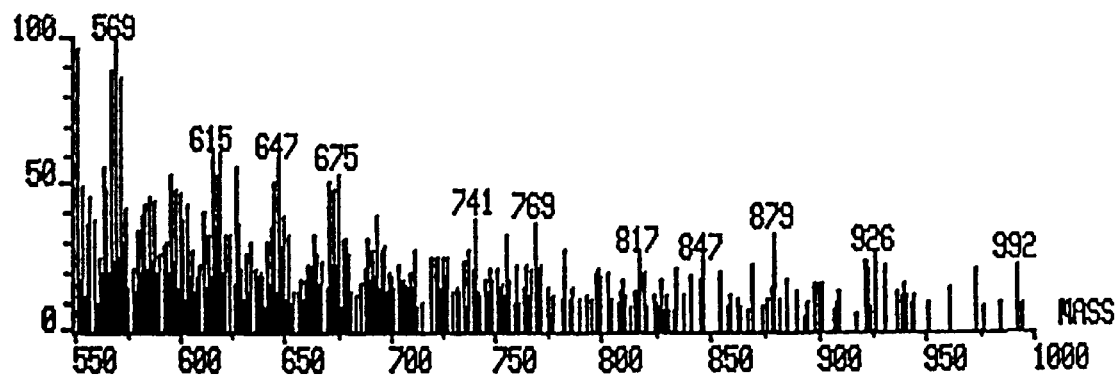

In FIG. 20, 5 $\mu$M CT-3501 was added. FIG. 20 is the 5 second time point and shows (in comparison to FIG. 17 without drug) that whereas synthesis of 1-stearoyl 2-linoleoyl PA is maintained, the synthesis of the other PA species was greatly reduced. Similarly, in FIG. 21, PA species with masses from 675 to 740 were all but obliterated by CT-3501 treatment, but the synthesis of saturated palmitoyl and myristoyl PA's was maintained or increased (675 is 1-palmitoyl, 2-stearoyl PA or 1-stearoyl, 2-palmitoyl PA, 647 is 1-palmitoyl, 2-palmitoyl PA or 1-myristoyl, 2-stearoyl PA, and 619 is 1-myristoyl, 2-palmitoyl PA).

DETAILED DESCRIPTION OF THE INVENTION

The present invention is based upon the pioneering discovery that certain PA species are released in response to pro-inflammatory stimuli mediated by, by example, PDGF, EGF, FGF and VEGF, and that the increase in the PA species can be inhibited by addition of certain compounds. Therefore, this invention has resulted in the discovery of a new class of compounds useful for treating or preventing the progression of a large group of diseases mediated by such pro-inflammatory cytokines and treatable by inhibition of intracellular signaling of such pro-inflammatory cytokines. The data described herein shows that PA inhibition in response to inflammatory stimulus is useful for treating diseases associated with increased proliferation in response to PDGF, VEGF, EGF, or FGF or other heparin-binding growth factors such as Her2,3,4/regulin, IGF-1 or 2.

A number of intracellular signaling events take place following PDGF, EGF, FGF or VEGF binding to their respective cell surface receptors. All of the receptors in this class of cytokines possess intrinsic tyrosine phosphorylation activity. Shortly after binding, the receptors are phosphorylated at various sites in their intracellular domain by intrinsic tyrosine kinase activity of the receptor. This leads to the creation of additional binding sites for intracellular proteins. For instance, for PDGF these include phospholipase C-g-1 (PLC-$\gamma$-1), the ras GTPase activating protein (GAP), phosphatidylinositol 3 kinase (PI3kinase), pp60c-src, p62c-yes, p50-fyn, Nck, and CRB2 as well as a 120 kd and a 64 kd species. Some of the proteins that associate with the receptor are signal transduction enzymes. For example, PLC-g-1 is a specific phosphodiesterase that produces diacylglycerol (DAG) and inositol triphosphate, two second messengers that activate a serine/threonine specific protein kinase protein kinase C (PKC) and increase intracellular calcium levels. PI3kinase is a lipid kinase that phosphorylates the D3 position of phosphatidylinositol phosphatidylinositol-4-phosphate, or PI 4,5,P2. The physiological significance of this intracellular lipid species is unclear, but mutant PDGF receptors that no longer bind PI3kinase by virtue of a substitution of a specific tyrosine residue no longer proliferate in response to PDGF. In addition, PDGF induces activation of the serine/threonine kinase MAP kinase, via MAP kinase kinase, which may be activated by activation of ras/raf pathway. MAP kinase acts to activate the nuclear transcription factors c-jun, c-fos and possibly c-myc. PDGF, also up regulates increased transcription of these transcription factors.

PDGF, FGF, VEGF, EGF, Her2,3,4/regulin, and IGF-1 or 2 induce increased levels of phosphatidic acid (PA). PA can be produced by either a membrane associated lysophosphatidic acyl transferase (LPAAT), by phospholipase D catalyzed hydrolysis of phosphatidyl choline or phosphatidylethanolamine, or via DAG kinase conversion of diacyl glycerol (DAG) to PA. PA is a potent intracellular signaling lipid and can be converted to DAG by phosphatidyl phosphohydrolase (PAPH). The data presented herein show that a class of small molecule inhibitors of PA specifically block cellular mitogenesis in a variety of cell types to PDGF (FIGS. 1, 3, 5, 9, 10, 11, 13, 14, and 17–21), VEGF (FIGS. 7 and 15), FGF (FIGS. 2 and 4) and EGF (FIG. 8). The compounds do not inhibit receptor tyrosine phosphorylation (FIG. 14), PI3-kinase activation, PLC-γ activation or calcium mobilization (FIG. 11). These compounds do not block MAP kinase or MAP kinase kinase activity, nor do they inhibit increased transcription of intracellular transcription factors jun, fos or myc. What they do have in common, is inhibition of PA induction (FIGS. 16a–e and 17–21) and the ability of PA to stimulate mitogenesis (FIG. 16).

As shown in FIG. 16a–e, addition of various types of PA's, including L-a PA (derived from natural sources), 1,2 dilauroyl-sn-glycero-3-phosphate, 1,2 dioleoyl-sn-glycero-3-phosphate, 1-stearolyl-2-aracidonyl-sn-glycero-3-phosphate and 1-alkyl-oleoyl-2-oleoyl-PA, are all mitogenic in Balb/3T3 cells.

PA inhibition in response to inflammatory stimuli is useful for treating or preventing various diseases associated with increased proliferation in response to PDGF, VEGF, EGF, or FGF or other heparin-binding growth factors such as Her2, 3,4/regulin, IGF-1 or 2. The present invention provides a method for:

(1) inhibiting new blood vessel formation that is useful for treating or preventing progression of diabetic retinopathy, cavernous haemangiomas, Kaposi's sarcoma, tumors composed of endothelial-like cells, and growth of cancer cells by preventing their development of a new blood supply;

(2) suppressing development of kidney diseases due to cytokine induced proliferation of mesangial cells and/or glomerular epithelial cells that is useful for treating or preventing progression of diabetic glomerulosclerosis and other glomerulonephritides of various types and etiologies;

(3) preventing joint destruction accompanying rheumatoid arthritis due to proliferation of synovial cells;

(4) suppressing manifestations of psoriasis due to proliferation of keratinocytes and accumulation of inflammatory cells;

(5) suppressing accelerated atherogenesis involved in restenosis of coronary vessels or other arterial vessels following angioplasty;

(6) suppressing atherogenesis, coronary artery disease and other vasculopathies due to atherogenesis; and (7) suppressing tumor growth via paracrine or autocrine mediated responses to PDGF, FGF EGF or VEGF that is useful for treating or preventing progression of tumors such as breast cancer stimulated through overexpression of her-2-neu receptor, wherein the inventive method comprises administering a compound that inhibits signal transduction through cellular accumulation of non-arachidonyl phosphatidic acid (PA) selected from the group consisting of 1-o-octadecanyl 2-oleoyl PA (687), 1-oleoyl 2-linoleoyl PA (697 or 698), 1-o-octadecanyl 2-linoleoyl PA (681), 1-o-octadecanyl-9,12-dienyl 2-linoleoyl PA (679), 1-myristoyl 2-oleoyl PA (645), 1-o-myristoyl 2-stearoyl PA (633), 1,2-sn-dilinoleoyl PA (695), 1-oleoyl 2-linoleoyl PA (697), 1-stearoyl 2-oleoyl PA (701), 1-o-oleoyl 2-20:4 PA (707), 1-o-linoleoyl 2-20:4 PA (705), 1-o-linoleoyl 2-20:5 PA (703), and combinations thereof. The numbers in parens next to each PA species shows the approximate molecular weight of the PA species as seen by mass spectroscopy analysis. More specifically, compounds comprise compounds and pharmaceutical compositions having the formula:

(X)j–(core moiety), wherein j is an integer from one to three, the core moiety comprises at least one five to seven-membered ring or an open chain analog of such a ring group and X is a racemate mixture or R or S enantiomer of:

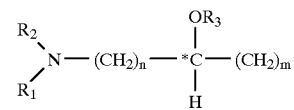

wherein * C is a chiral carbon atom; n is an integer from one to four; one or more carbon atoms of $(CH_2)_n$ may be substituted by a keto or hydroxy group; m is an integer from one to fourteen; independently, $R_1$ and $R_2$ are hydrogen, a straight or branched chain alkane or alkene of up to twelve carbon atoms in length, or $—(CH_2)_w R_5$, w being an integer from two to fourteen and $R_5$ being a mono-, di- or tri-substituted or unsubstituted aryl group, substituents on $R_5$ being selected from the group consisting of hydroxy, chloro, fluoro, bromo, or $C_{1-6}$ alkoxy; or jointly, $R_1$ and $R_2$ form a substituted or unsubstituted, saturated or unsaturated heterocyclic group having from four to eight carbon atoms, N being a hetero atom; and $R_3$ is hydrogen or $C_{1-3}$: or

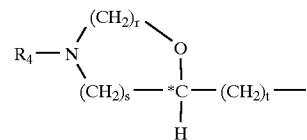

wherein $R_4$ is a hydrogen, a straight or branched chain alkane or alkene of up to eight carbon atoms in length, $—(CH_2)_w R_5$, w being an integer from two to fourteen and $R_5$ being a mono-, di- or tri-substituted or unsubstituted aryl group, substituents on $R_5$ being selected from the group consisting of hydroxy, chloro, fluoro, bromo, or alkoxy $C_{1-6}$ alkoxy, or a substituted or unsubstituted, saturated or unsaturated heterocyclic group having from four to eight carbon atoms, N being a hetero atom; r and s are independently integers from one to four; the sum (r+s) is not greater than five; t is an integer from one to fourteen; and one or more carbon atoms of $(CH_2)_s$ or $(CH_2)_t$ may be substituted by a keto or hydroxy group, or X is independently a resolved enantiomer ω-1 secondary alcohol-substituted alkyl $(C_{5-8})$ substantially free of the other enantiomer, or X is a branched $—(CH_2)_a—CHR_6—(CH_2)_b—R_7$, wherein a is an integer from about 4 to about 12, b is an integer from 0 to 4, $R_6$ is an enantiomer (R or S) or racemic mixture $(C_{1-6})$ alkyl or alkenyl, and $R_7$ is a hydroxy, keto, cyano, chloro, iodo, flouro, or chloro group.

Preferably, the core moiety has from one to three, five to six-membered ring structures in a predominantly planar configuration. Preferably, the amino alcohol substituent (X) is bonded to a ring nitrogen if one exists. For example, the core moiety may be selected from the group consisting of substituted or unsubstituted barbituric acid; benzamide; benzene; cyclohexanedione; cyclopentanedione; delta-lactam; flutarimide; glutarimide; homophthalimide; imidazole amide; isocarbostyrile; lumazine; napthlalene; pthalimide; piperidine; pyridine; pyrimidine; pyrrole amide; quinazolinedione; quinazolinone; quinolone; recorsinol; succinimide; thymine; triazine; uracil or xanthine. Preferred cores include substituted or unsubstituted xanthine, more preferably halogen-substituted xanthine. Exemplary preferred cores include, but are not limited to: 1,3-cyclohexanedione, 1,3-cyclopentanedione; 1,3-dihydroxynaphthalene; 1-methyllumazine; methylbarbituric acid; 3,3-dimethylflutarimide; 2-hydroxypyridine; methyldihydroxypyrazolopyrimidine (preferably, 1,3-dimethyldihydroxypyrazolo[4,3-d] pyrimidine); methylpyrrolopyrimidine (preferably, 1-methylpyrrolo [2,3-d]pyrimidine); 2-pyrrole amides; 3-pyrrole amides; 1,2,3,4-tetrahydroisoquinolone; 1-methyl-2,4(1H,3H) quinazolinedione (1-methylbenzoyleneurea); quinazolin-4 (3H)-one; alkyl-substituted ($C_{1-6}$) thymine; methylthymine; alkyl-substituted ($C_{1-6}$) uracil; 6-aminouracil; 1-methyl-5,6-dihydrouracil; 1-methyluracil; 5- and/or 6-position substituted uracils; 1,7-dimethylxanthine, 3,7-dimethylxanthine; 3-methylxanthine; 3-methyl-7-methylpivaloylxanthine; 8-amino-3-methylxanthine; and 7-methylhypoxanthine. Alternatively, the compound are a resolved R or S (preferably R) enantiomer of an ω-1 alcohol of a straight chain alkyl ($C_{5-8}$) substituted at the 1-position of 3,7-disubstituted xanthine. Preferably, the amino alcohol substituent (X) is bonded to a ring nitrogen if one exists. For example, the core moiety is selected from the group consisting of xanthine, halogen-substituted xanthines, 3,7-dimethylxanthine, 3-methylxanthine, 3-methyl-7-methylpivaloylxanthine, 8-amino-3-methylxanthine, 7-methylhypoxanthine, 1-methyluracil, 1-methylthymine, 1-methyl-5,6-dihydrouracil, glutarimides, phthalimide, 1-methyl-2,4(1H,3H)-quinazolinedione (1-methylbenzoyleneurea), 6-aminouracil, homophthalimide, succinimide, 1,3-cyclohexanedione, resorcinol, 1,3-dihydroxynaphthalene, 1,3-cyclopentanedione, 1,3-dimethyldihydroxypyrazolo[4,3-d] pyrimidine, 5-substituted uracils, 6-substituted uracils, 1-methylpyrrolo[2,3-d] pyrimidine, 1-methyllumazine, imidazole amides, 2-pyrrole amides, 3-pyrrole amides, benzamides, methylbarbituric acid, benzene, piperdine, delta-lactam, 2-hydroxypyridine, 1,2,3,4-tetrahydroisoquinolone, isocarbostyril, and quinazolin-4 (3H)-one. Most preferably, the core moiety is a substituted xanthine, such as a 3,7 dimethylxanthine. The core moiety can also include a non-cyclic group. Examples of non-cyclic core groups include open chain analogs of glutarimide, carboxilic acid, a hydroxyl group, sulfone, sulfonate, and the like. Examples of compounds with demonstrated activity include compounds selected from the group consisting of R-1-(5-hydroxyhexyl)-3,7-dimethylxanthine, N-(11-octylamino-10-hydroxyundecyl)-homophthalimide, N-(11-octylamino-10-hydroxyundecyl)-3-methylxanthine, N-(11-octylamino-10-hydroxyundecyl)-2-piperdone, 3-(11-octylamino-10-hydroxyundecyl)-1-methyluracil, 3-(11-octylamino-10-hydroxyundecyl)-1-methyldihydrouracil, 1-(9-decylamino-8-hydroxynonyl)-3,7-dimethylxanthine, 1-(9-dodecylamino-8-hydroxynonyl)-3,7dimethylxanthine, 1-(11-hexylamino-8-hydroxyundecyl)-3,7-dimethylxanthine, N-(11-phenylamino-10-hydroxyundecyl)-3,7-dimethylxanthine, 1-(9-(2-hydroxydecyl-1-amino)nonyl)-3,7-dimethylxanthine, and combination thereof.

Preferably, the core moiety is a member selected from the group consisting of substituted or unsubstituted: barbituric acid; benzamide; benzene; biphenyl; cyclohexanedione; cyclopentanedione; delta-lactam; flutarimide; glutarimide; homophthalimide; imidazole amide; isocarbostyrile; lumazine; napthlalene; pteridine; pthalimide; piperidine; pyridine; pyrimidine; pyrrole amide; quinazolinedione; quinazolinone; quinolone; recorsinol; stilbene; succinimide; theobromine; thymine; triazine; tricyclododecane; uracil and xanthine. Specific compounds are listed below.

TABLE 1

R-1-(5-hydroxyhexyl)-3,7-dimethylxanthine
N-(11-octylamino-10-hydroxyundecyl)-homophthalimide
N-(11-octylamino-10-hydroxyundecyl)-3-methylxanthine
N-(11-octylamino-10-hydroxyundecyl)-2-piperdone
3-(11-octylamino-10-hydroxyundecyl)-1-methyluracil
3-(11-octylamino-10-hydroxyundecyl)-1-methyldihydrouracil
1-(9-decylamino-8-hydroxynonyl)-3,7-dimethylxanthine
1-(9-dodecylamino-8-hydroxynonyl)-3,7-dimethylxanthine
1-(11-hexylamino-8-hydroxyundecyl)-3,7-dimethylxanthine
N-(11-phenylamino-10-hydroxundecyl)-3,7-dimethylxanthine
1-(9-(2-hydroxydecyl-1-amino)nonyl)-3,7-dimethylxanthine
N-(9-Octylamino-8-hydroxynonyl)phthalimide

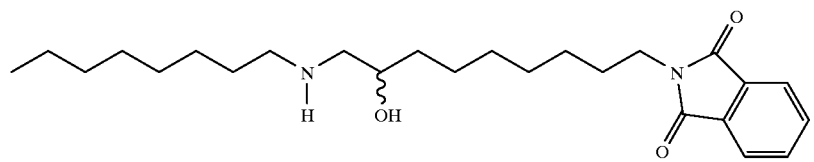

N-(11-Octylamino-10-hydroxyundecyl)homophthalimide

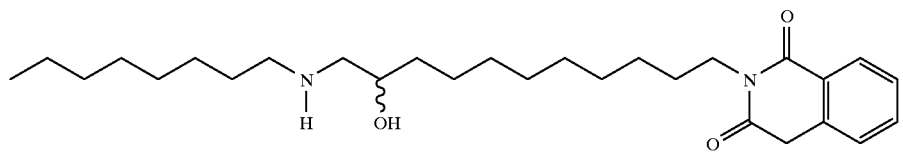

TABLE 1-continued
1-(5-hydroxy-6-(N-benzyl)aminohexyl)-3-methylbenzoyleneurea
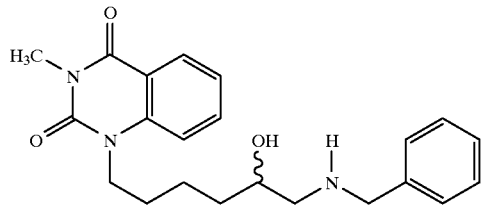
3-(11,10-Oxidoundecyl)quinazoline-4(3H)-one
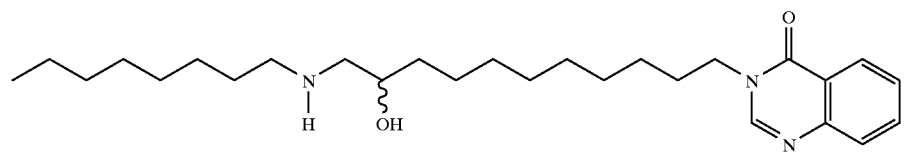
N²-(5-hydroxy-6-(N³-propyl)aminohexyl)-(N¹-propyl)glutaramide
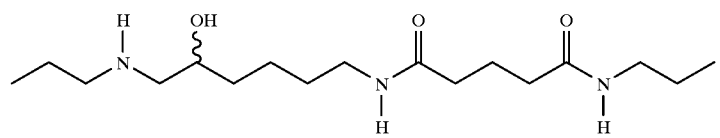
2-(11-Octylamino-10-hydroxyundeclcarboxamido)-octylcarboxamidobenzyl
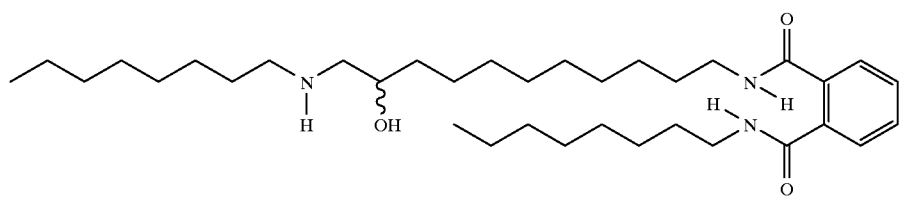
1-Octylamino-2,11-undecadiol
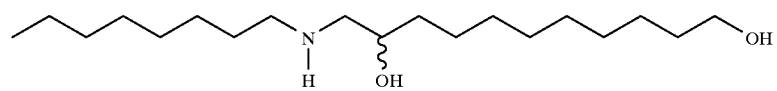
1-(9-Octylamino-8-hydroxynonyl)-3-methylxanthine
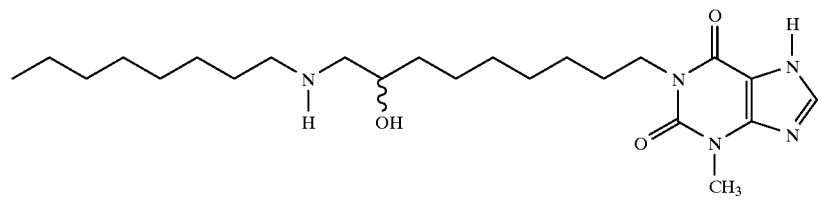
1-(9-Tetradecylamino-8-hydroxynonyl-3-methylxanthine
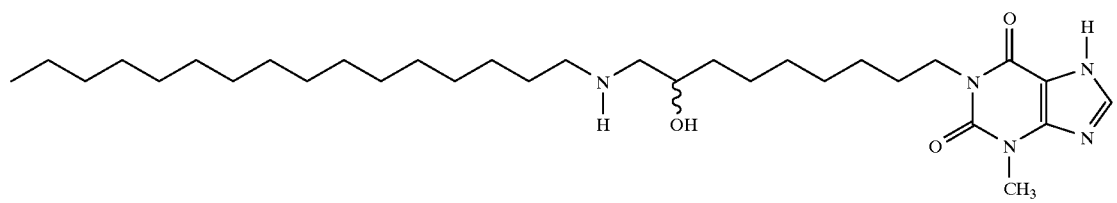

TABLE 1-continued
1-(11-Octylamino-10-hydroxyundecyl)-3-methylxanthine
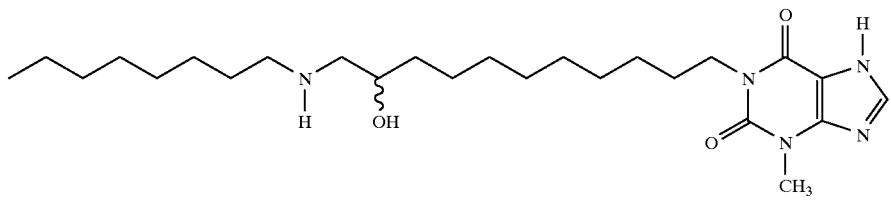
7-(11-Octylamino-10-hydroxyundecyl)-1,3-dimethylxanthine
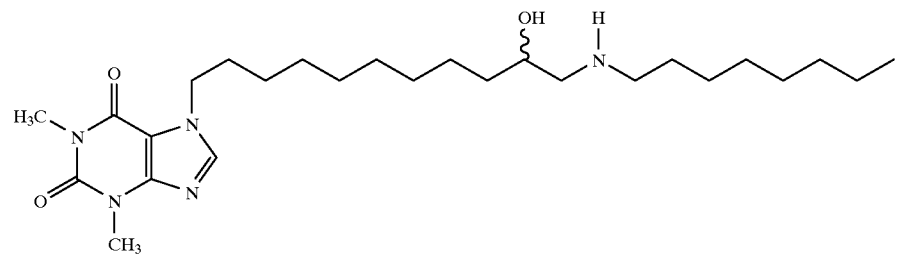
1-(11,10-Octylamino-10-hydroxyundecyl)-1-methyl-2,4-dioxotetrahydropteridine
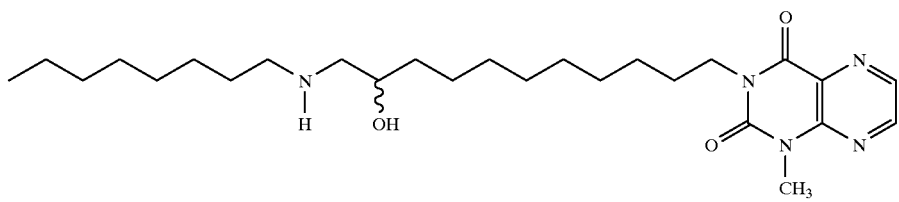
1-(5-hydroxy-6-(N-benzyl)aminohexyl)-3,7-dimethylxanthine
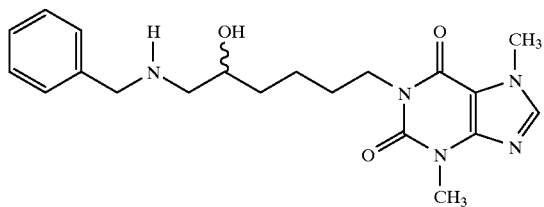
1-(5-hydroxy-6-(N-propyl)aminohexyl)-3,7-dimethylxanthine
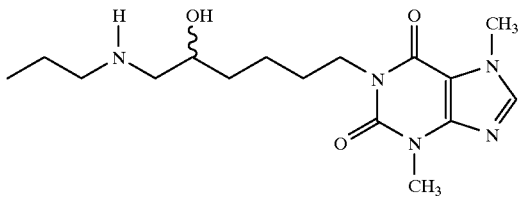
N-(11-Octylamino-10-hydroxyundecyl)glutarimide
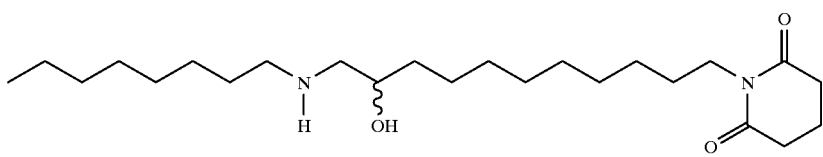

TABLE 1-continued
N-(11-Octylamino-10-hydroxyundecyl)-2-piperidone
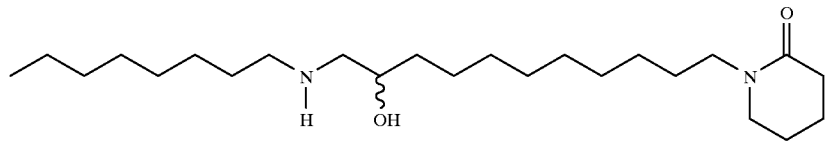
N-(11-Octylamino-10-hydroxyundecyl)succinimide
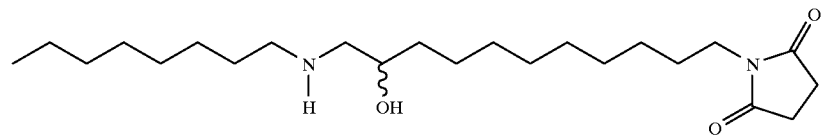
2-(11-Octylamino-10-hyroxyundecyl)-1,3-dimethoxybenzene
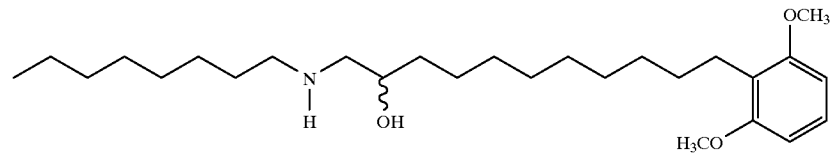
3-(5-hydroxy-6-(N-propyl)aminohexyl)-1-methyluracil
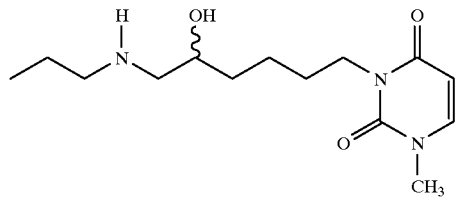
3-(9-Octylamino-8-hydroxynonyl)-1-methyluracil
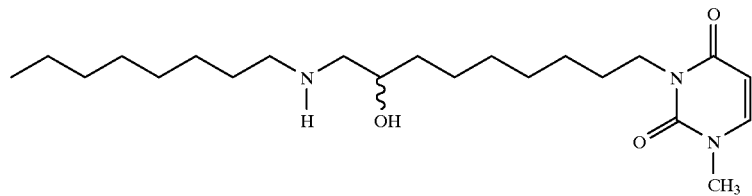
3-(11-Octylamino-10-hydroxyundecyl)-1-methyluracil
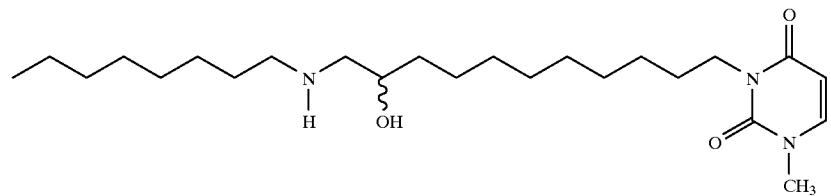

TABLE 1-continued
3-(11-Octylamino-10-hydroxyundecyl)-1-methyldihydrouracil
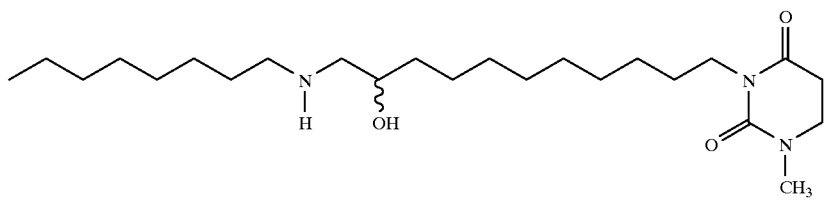
3-(8-Octylamino-9-hydroxynonyl)-1-methylthymine
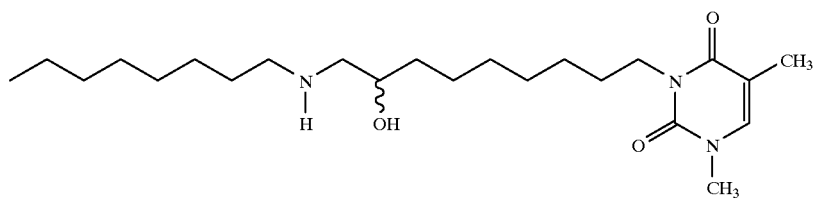
3-(5-hydroxy-6-(N-undecyl)aminohexyl)-1-methylthymine
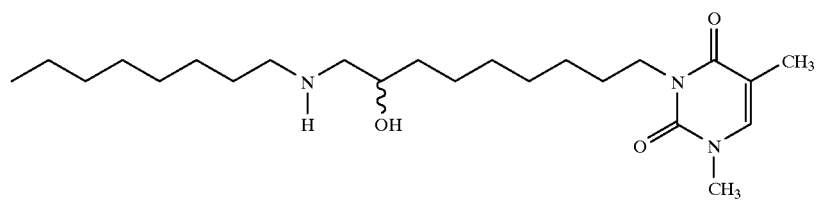
3-(11-Octylamino-10-hydroxyundexyl)-1-methylthymine
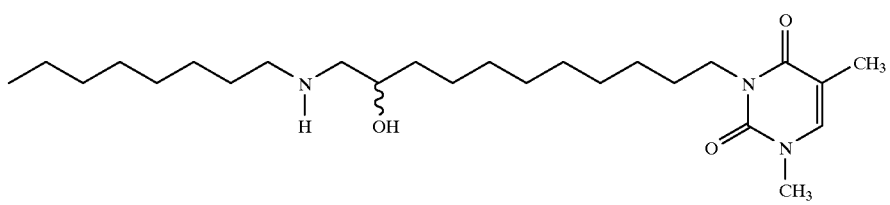
3-(6-Propylamino-5-hydroxyhexyl)-1-methylthymine
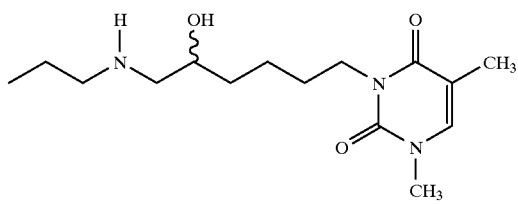
1-(8-hydroxy-9-(N-benzyl)aminononyl)-3,7-dimethylxanthine
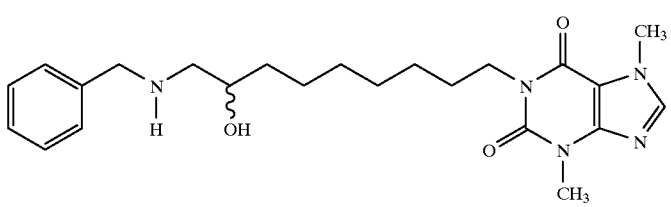

TABLE 1-continued
1-(5-(hydroxy-6-(N-octyl)aminohexyl)-3,7-dimethylxanthine
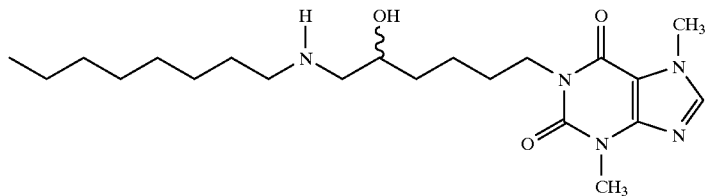
1-(5-hydroxy-6-(N-(4-phenyl)butyl)aminohexyl)-3,7-dimethylxanthine
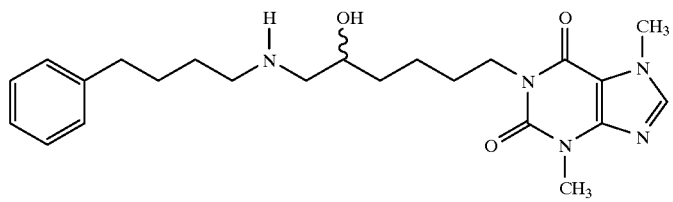
1-(6-Undecylamino-5-hydroxyhexyl)-3,7-dimethylxanthine
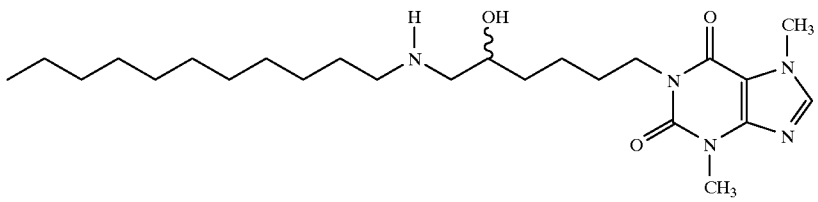
1-(5-hydroxy-6-(N-cyclohexylmethyl)aminohexyl)-3,7-dimethylxanthine
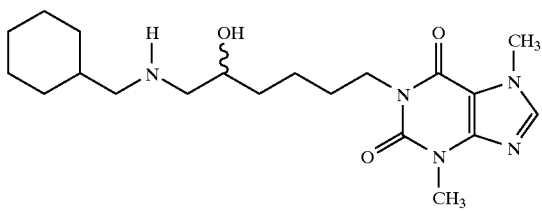
1-(5-hydroxy-6-(N-(6-hydroxy)hexyl)aminohexyl)-3,7-dimethylxanthine
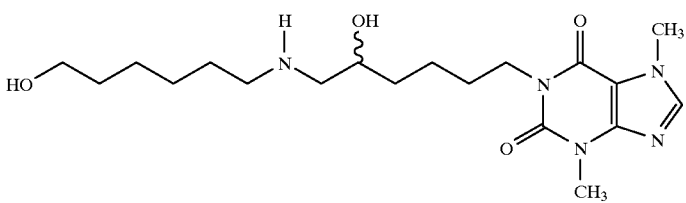
1-(5-hydroxy-6-(N,N-dihexyl)aminohexyl)-3,7-dimethylxanthine
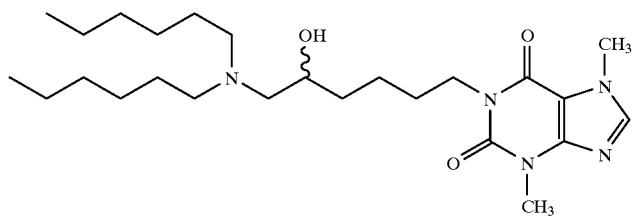

TABLE 1-continued
1-(5-hydroxy-6-(N-(4-methoxy)benzyl)aminohexyl)-3,7-dimethylxanthine
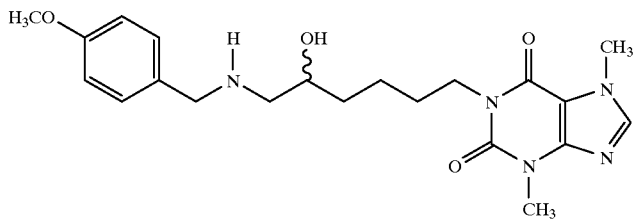
1-(8-hydroxy-9-(N-octyl)aminononyl)-3,7-dimethylxanthine
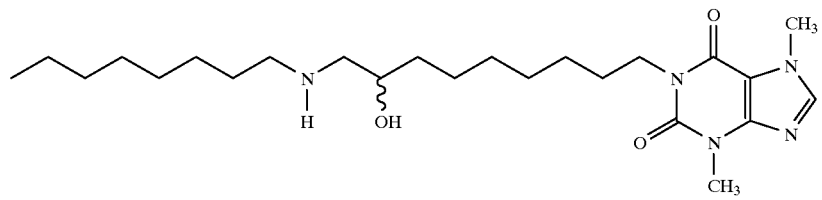
1-(5-hydroxy-6-(N-tetradecyl)aminohexyl)-3,7-dimethylxanthine
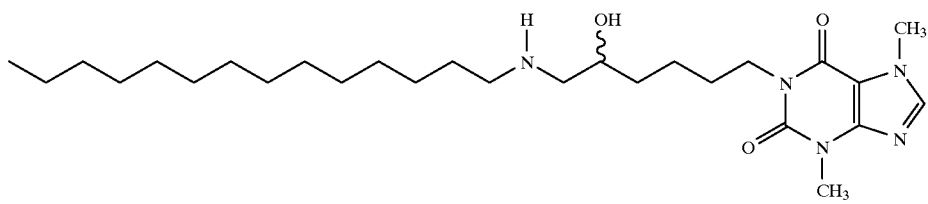
1[6-(Cyclopropymethylamino)-5-hydroxyhexyl)]-3,7-dimethylxanthine
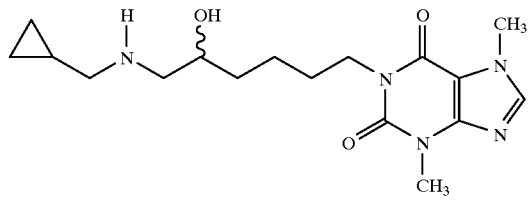
1-(6-Decylamino-5-hydroxyhexyl)-3,7-dimethylxanthine
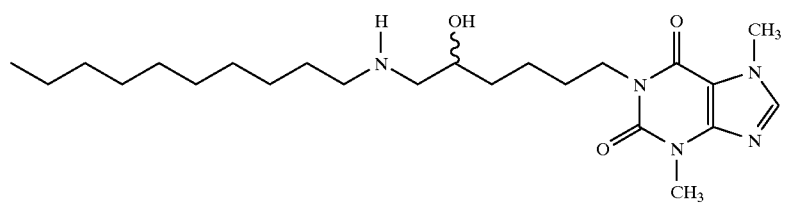
1-(6-Dodecylamino-5-hydroxyhexyl)-3,7-dimethylxanthine
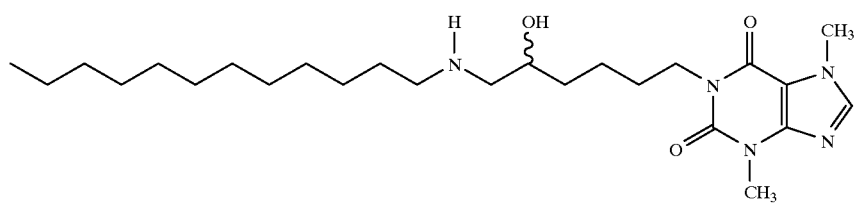

TABLE 1-continued
1-(11-Benzylamino-10-hydroxyundecyl-3,7-dimethylxanthine
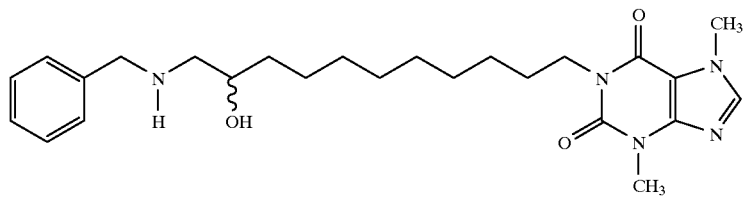
1-(9-Decylamino-8-hydroxynonyl)-3,7-dimethylxanthine
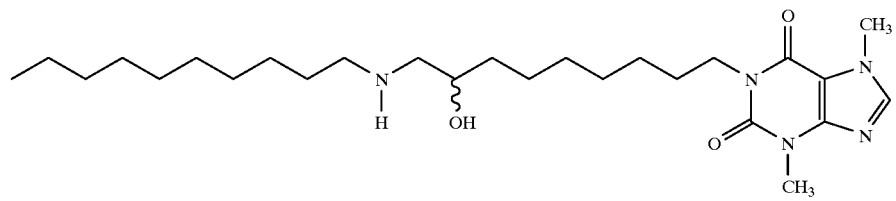
1-(9-Tetradecylamino-8-hydrononyl)-3,7-dimethylxanthine
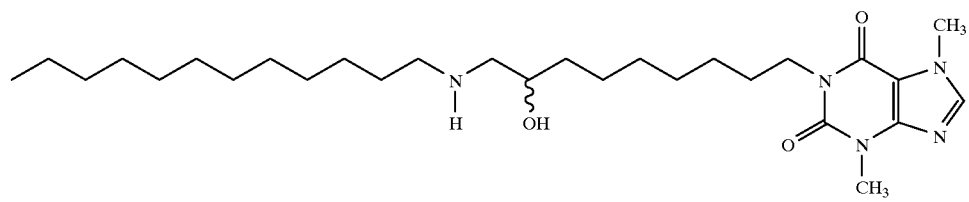
1-(9-Tetradecylamino-8-hydroxynonyl)-3,7-dimethylxanthine
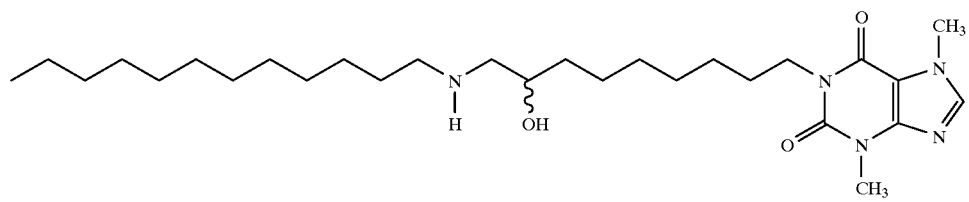
1-(11-Hexylamino-10-hydroxyundecyl)-3,7-dimethylxanthine
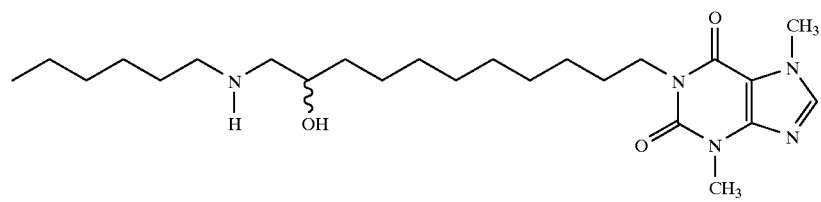
1-(11-Octylamino-10-hydroxyundecyl-3,7-dimethylxanthine
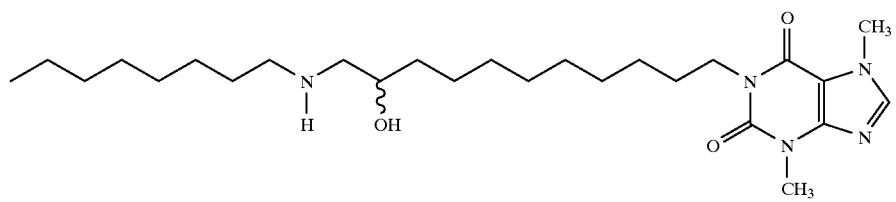

TABLE 1-continued
1-(6-Allylamino-5-hydroxyhexyl)-3,7-dimethylxanthine
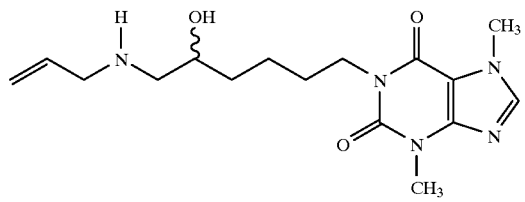
1-(11-Allylamino-10-hydroxyundecyl)-3,7-dimethylxanthine
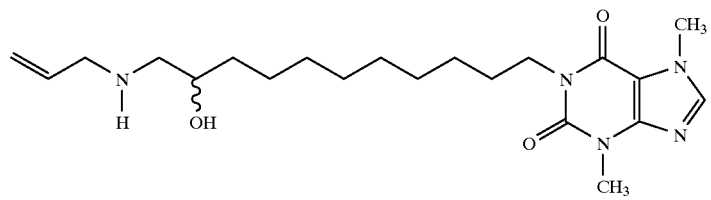
1-(6-N-Methyloctadecylamino-5-hydroxyhexyl)-3,7-dimethylxanthine
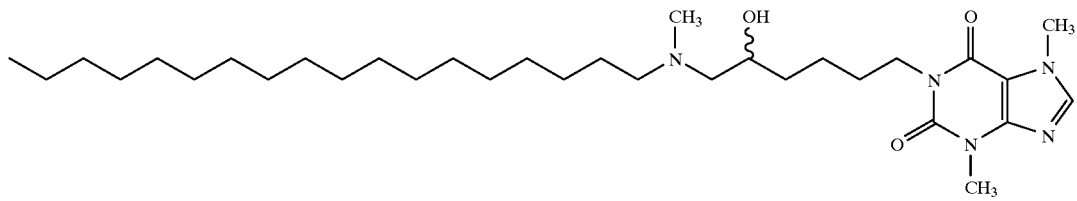
1-(11-Decylamino-10-hydroxyundecyl)-3,7-dimethylxanthine
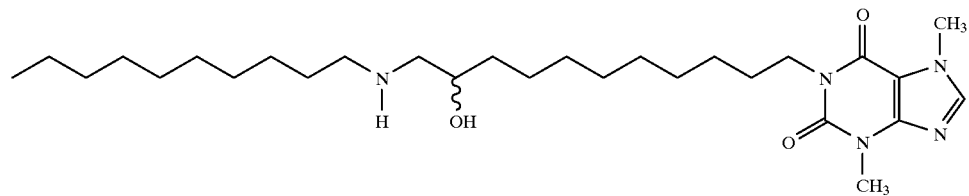
1-(11-Dodecylamino-10-hydroxyundecyl)-3,7-dimethylxanthine
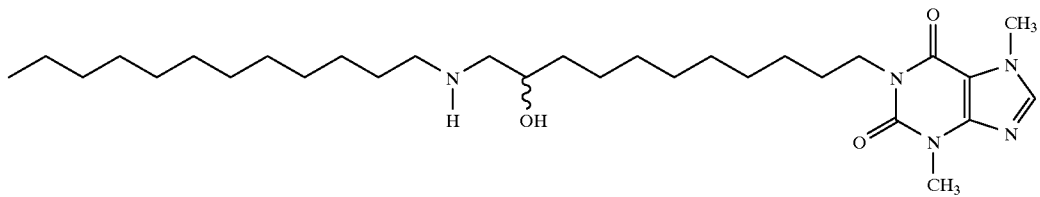
1-(11-Tetradecylamino-10-hydroxyundecyl)-3,7-dimethylxanthine
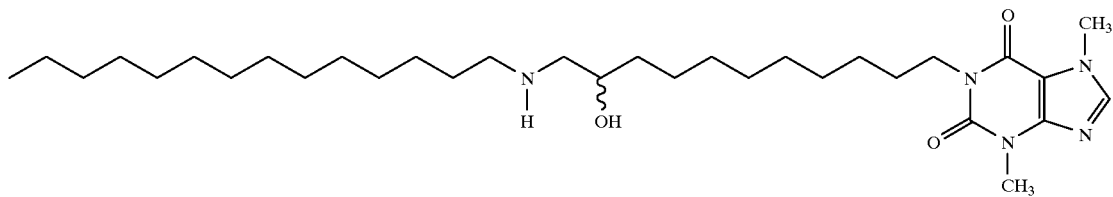

TABLE 1-continued

1[11-(4-Fluorobenzylamino)-10-hydroxyundecyl]-3,7-dimethylxanthine

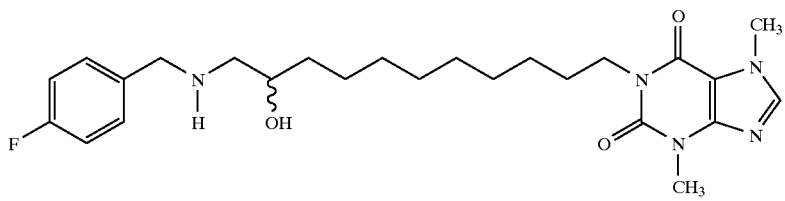

1-[11-(4-Trifluoromethylbenzylamino)-10-hydroxyundecyl]3,7-dimethylxanthine

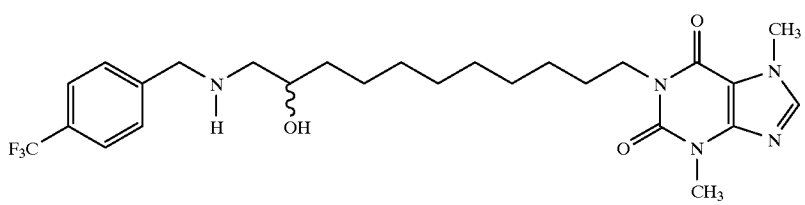

1-{11-(3-Diethylaminopropylamino)-10-hydroxyundecyl]-3,7-dimethlxanthine

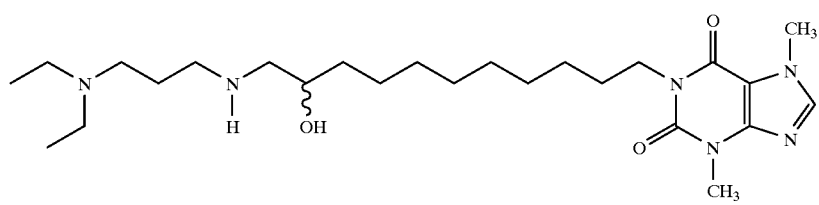

N,N'-bis[(10-yl-9-hydroxydecyl)-3,7-dimethylxanthine]diaminododecane

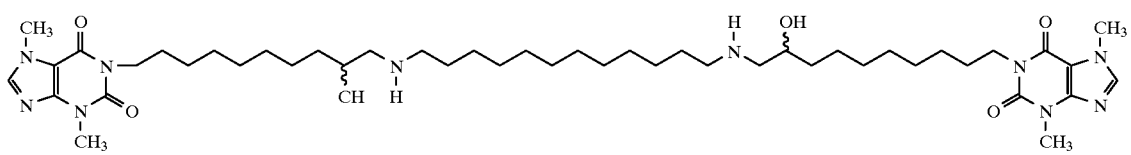

1-(14-Bromo-13-hydroxytetradecyl)-3,7-dimethylxanthine

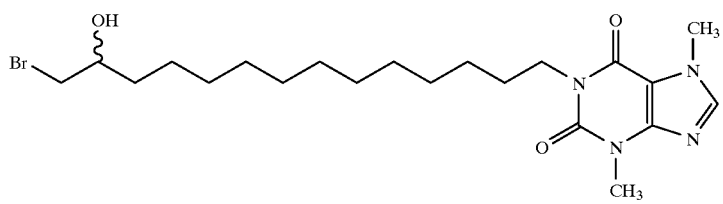

1-[11-(4-Aminobenzylamino)-10-hydroxyundecyl]-3,7-dimethylxanthine

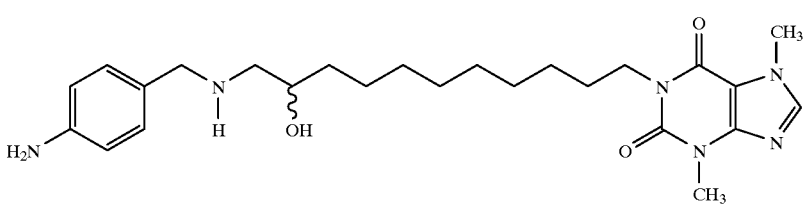

TABLE 1-continued
1-[11-(3,4,5-Trimethoxybenzylamino)-10-hydroxyundecyl]-3,7-dimethylxanthine
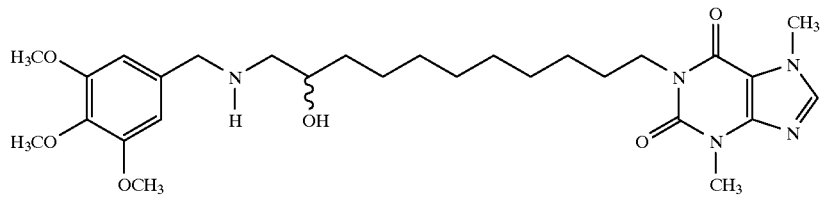
1-[11-(3-Butoxypropylamino)10-hydroxyundecyl}3,7-dimethylxanthine
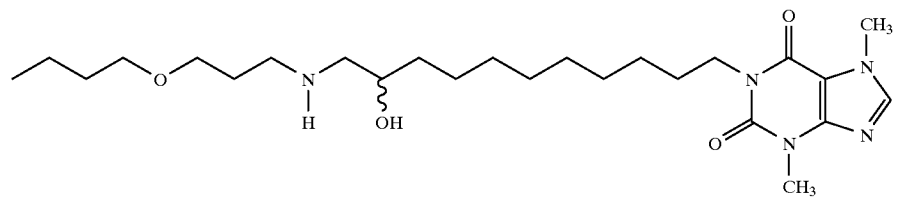
1-(14-Ocytlamino-13-hydroxytetradecyl]-3,7-dimethylxanthine
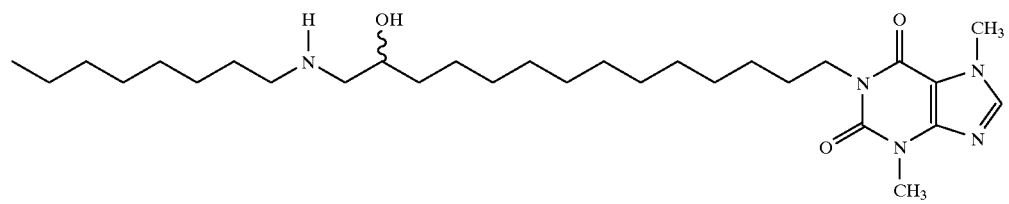
1-(11-Propylamino-10-hydroxyundecyl)-3,7-dimethylxanthine
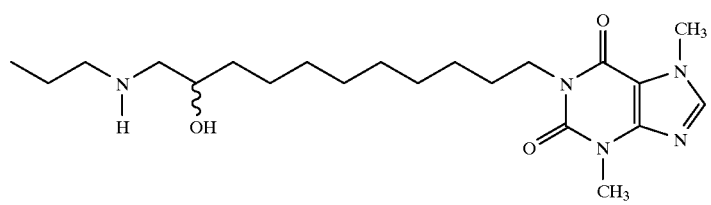
1-(1-Undecylamino-10-hydroxydecyl-3,7-dimethylxanthine
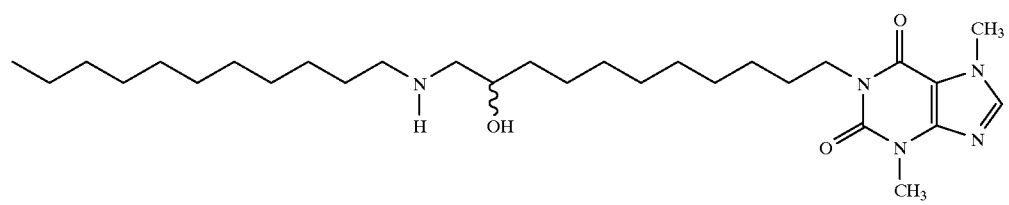
1-(11-Phenylamino-10-hydroxyundecyl)-3,7-dimethylxanthine
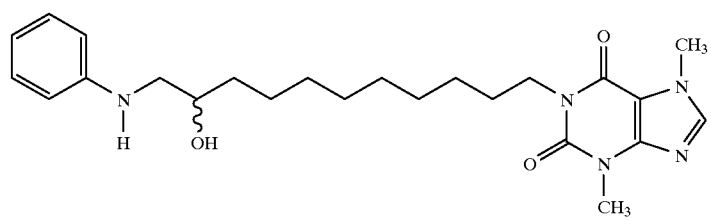

TABLE 1-continued
N,N-bis[11-yl-10-hydroxyundecyl)-3,7-dimethylxanthine]undecylamine
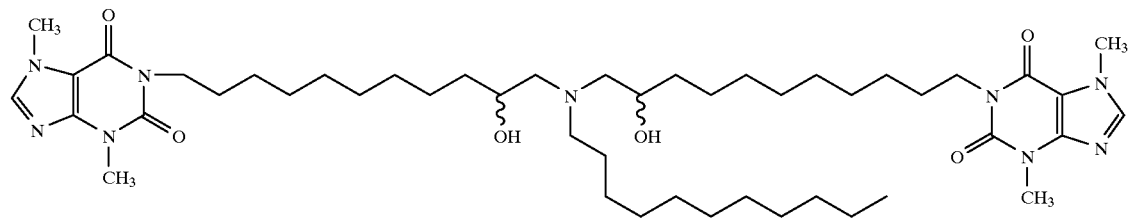
1-(11-Octadecylamino-10-hydroxyundecyl)-3,7-dimethylxanthine
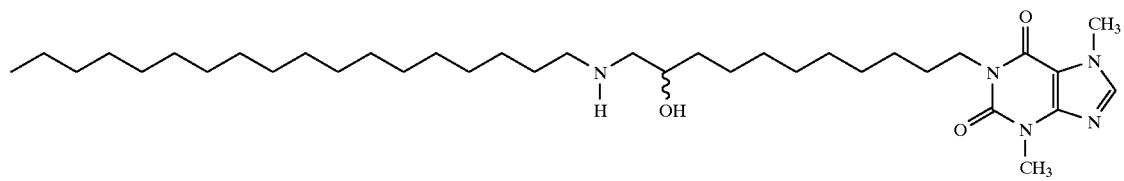
1-[9-(N-Methyloctylamino-8-hydroxynonyl)]-3,7-dimethylxanthine
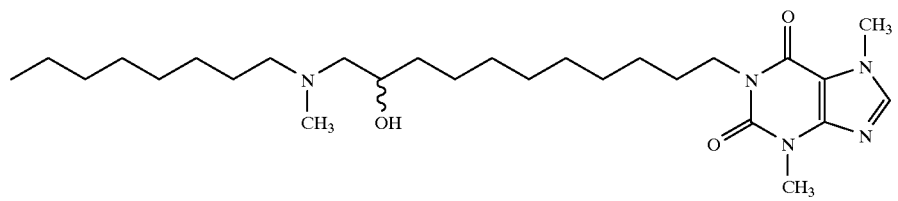
1-(4-Tetradecylamino-3-hydroxybutyl)-3,7-dimethylxanthine
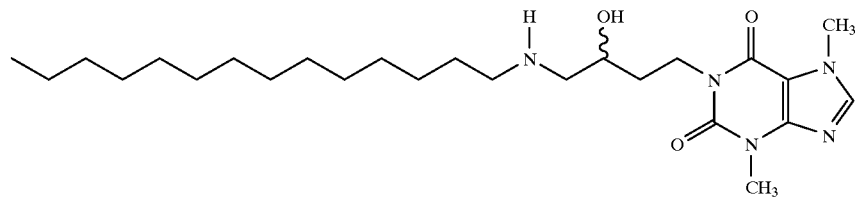
1-[9-(2-hydroxydecyl-1-amino)nonyl)-3,7-dimethylxanthine
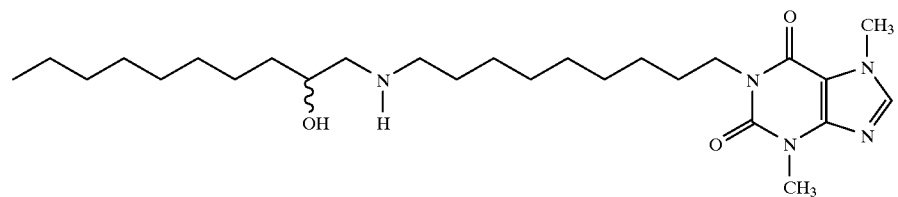
1-(6-Octadecylamino-5-hydroxyhexyl)-3,7-dimethylxanthine
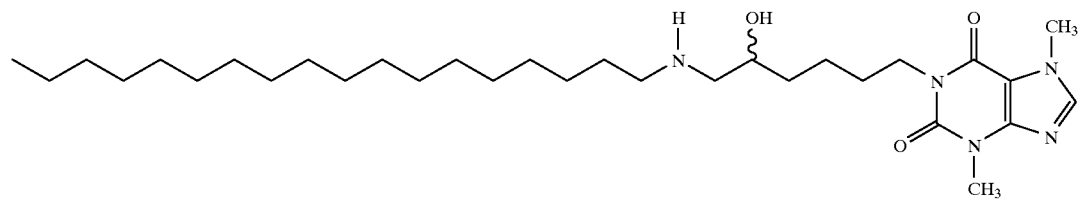

TABLE 1-continued

1-[11-(N-Octylacetamido)10-hydroxyundecyl]-3,7-dimethylxanthine

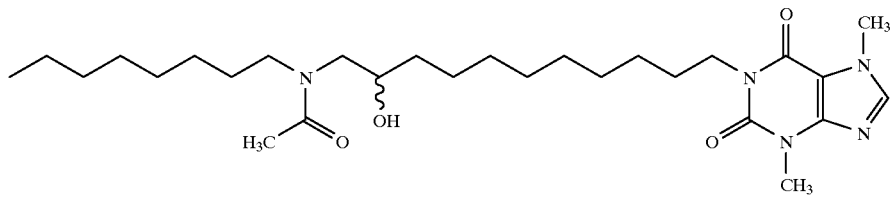

11-Octylamino-10-hydroxyundecanoic acid amide

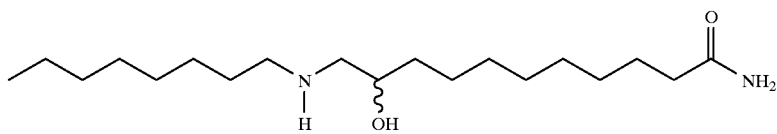

2-(11-Octylamino-10-hydroxyundecyl)-N-methylbenzamide

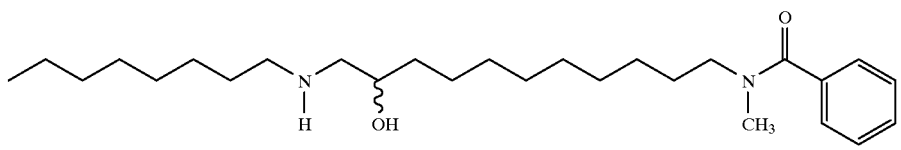

1-{11-(N-Methyl-N-octylamino)-10-hydroxyundecyl)-3,7-dimethylxanthine

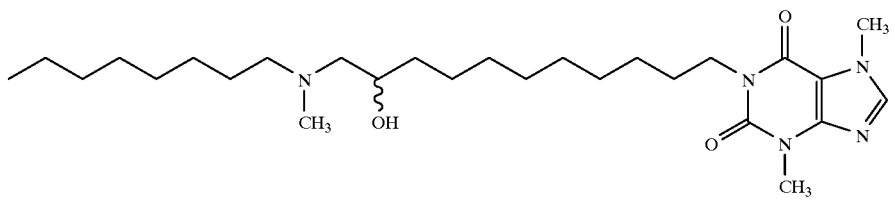

Formulation and Dosage

It will be recognized by one of skill in the art that the form and character of the pharmaceutically acceptable carrier or diluent is dictated by the amount of active ingredient with which it is to be combined, the route of administration and other well-known variables. An amino alcohol or chiral secondary alcohol compound or a pharmaceutically acceptable salt or hydrate or solvate thereof is administered to a patient in an amount sufficient to treat or prevent the disease. The route of administration of the illustrated compound (e.g., amino alcohol or chiral primary or secondary alcohol-substituted heterocyclic compound) is not critical but is usually oral or parenteral, preferably oral. The term parenteral, as used herein, includes intravenous, intramuscular, subcutaneous, intranasal, intrarectal, transdermal, opthalmic, intravaginal or intraperitoneal administration. The subcutaneous and intramuscular forms of parenteral administration are generally preferred. The daily parenteral dosage regimen will preferably be from about 0.01 mg/kg to about 25 mg/kg of total body weight, most preferably from about 0.1 mg/kg to about 4 mg/kg. Preferably, each parenteral dosage unit will contain the active ingredient in an amount of from about 0.1 mg to about 400 mg. The compounds are generally active when given orally and can be formulated as liquids, for example, syrups, suspensions or emulsions, tablets, capsules and lozenges. A liquid formulation will generally consist of a suspension or solution of the compound or pharmaceutically acceptable salt in a suitable liquid carrier(s), for example, ethanol, glycerine, non-aqueous solvent, for example polyethylene glycol, oils, or water with a suspending agent, preservative, flavoring or coloring agent. A composition in the form of a tablet can be prepared using any suitable pharmaceutical carrier(s) routinely used for preparing solid formulations. Examples of such carriers include magnesium stearate, starch, lactose, sucrose and cellulose. A composition in the form of a capsule can be prepared using routine encapsulation procedures. For example, pellets containing the active ingredient can be prepared using standard carriers and then filled into a hard gelatin capsule. Alternatively, a dispersion or suspension can be prepared using any suitable pharmaceutical carrier(s), for example, aqueous gums, celluloses, silicates or oils and the dispersion or suspension then filled into a soft gelatin capsule. The daily oral dosage regimen will preferably be from about 0.01 mg/kg to about 40 mg/kg of total body weight. Preferably, each oral dosage unit will contain the active ingredient in an amount of from about 0.1 mg to about 1000 mg.

It will be recognized by one of skill in the art that the optimal quantity and spacing of individual dosages of a compound or a pharmaceutically acceptable salt or hydrate or solvate thereof will be determined by the nature and extent of the condition being treated, the form, route and site of administration, and the particular patient being treated, and that such optimums can be determined by conventional techniques. It will also be appreciated by one of skill in the art that the optimal course of treatment (i.e., the number of doses of a compound or a pharmaceutically acceptable salt or hydrate or solvate thereof given per day and duration of therapy) can be ascertained by those skilled in the art using conventional course of treatment determination tests.

Without further elaboration, it is believed that one skilled in the art can, using the preceding description, utilize the present invention to its fullest extent. The following examples are, therefore, to be construed as merely illustrative and not a limitation of the scope of the present invention in any way.

EXAMPLE 1

This example illustrates an experiment where several compounds inhibited PDGFBB-induced proliferation of Balb/3T3 cells. Balb/3T3, clone A31 and Swiss 3T3 cells were grown in Dulbecco's modified Eagle's medium, high glucose and supplemented with 10% calf serum. Rest media for these cells consisted of DMEM and 0.2% calf serum. Cells were incubated overnight with PDGFBB (20 ng/ml, Pepro Tech, Inc., Rocky Hill, N.J.) and compound. Cell proliferation was determined by tritiated thymidine incorporation. Cell viability was determined with 2',7'-bis-(2-carboxyethyl)-5-(and)-carboxyflourescein, acetoxymethyl ester (BCECF, Molecular Probes, Inc., Eugene, Oreg.) added to a final concentration of 10 ug/ml for 30 minutes, 37° C. to each well. BCECF was removed, replaced with phosphate buffered saline and fluorescence determined using a Millipore Cytofluor 2300. The data (FIG. 1) show that the compounds inhibited cell proliferation at much lower concentrations than the cytotoxic concentration.

Figure 3:
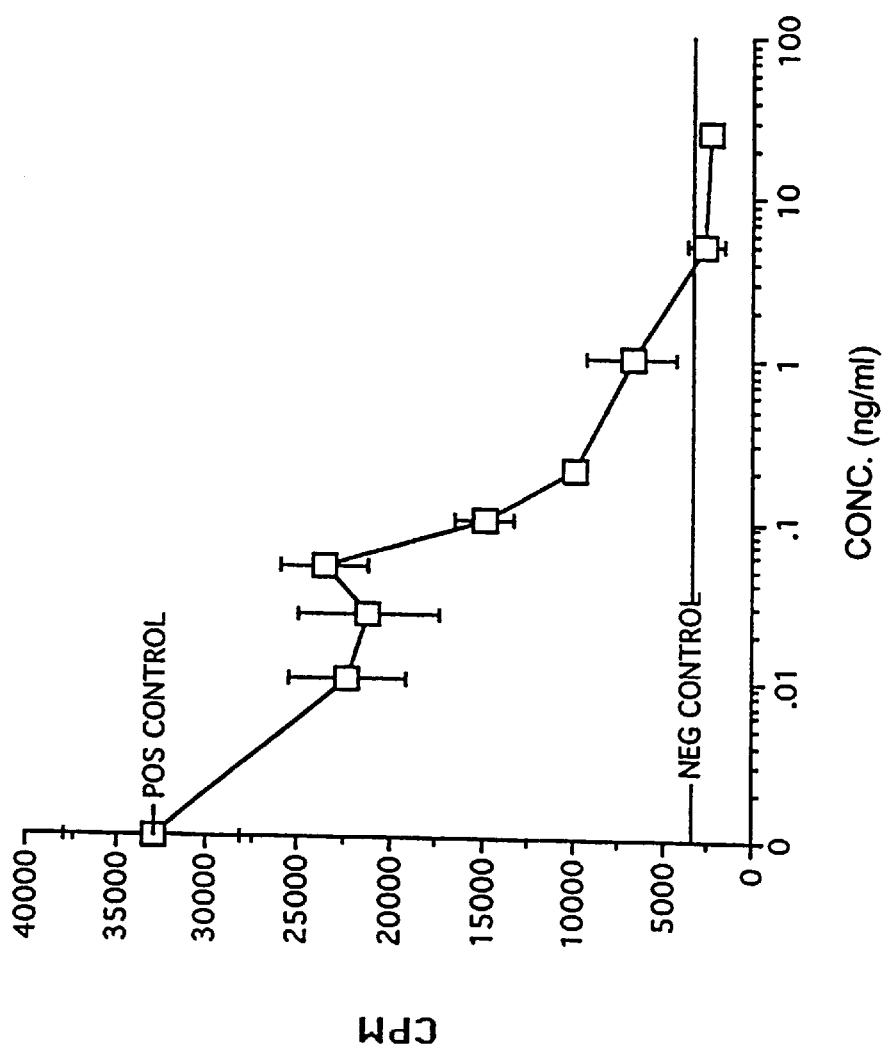
FIG. 3 illustrates that the proliferation of BALB /3T3 cells induced by PDGFBB was inhibited by CT-2576 (1-(11-octylamino-10-hydroxyundecyl)-3,7-dimethylxanthine) in a dose dependent manner. This is a predictive model for restenosis, atherogenesis, rheumatoid arthritis and degenerative kidney diseases.

FIG. 3 illustrates that the proliferation of BALB/3T3 cells induced by PDGFBB was inhibited by CT-2576 in a dose dependent manner. This is a predictive model for restenosis, atherogenesis, rheumatoid arthritis and degenerative kidney diseases.

Figure 5A:
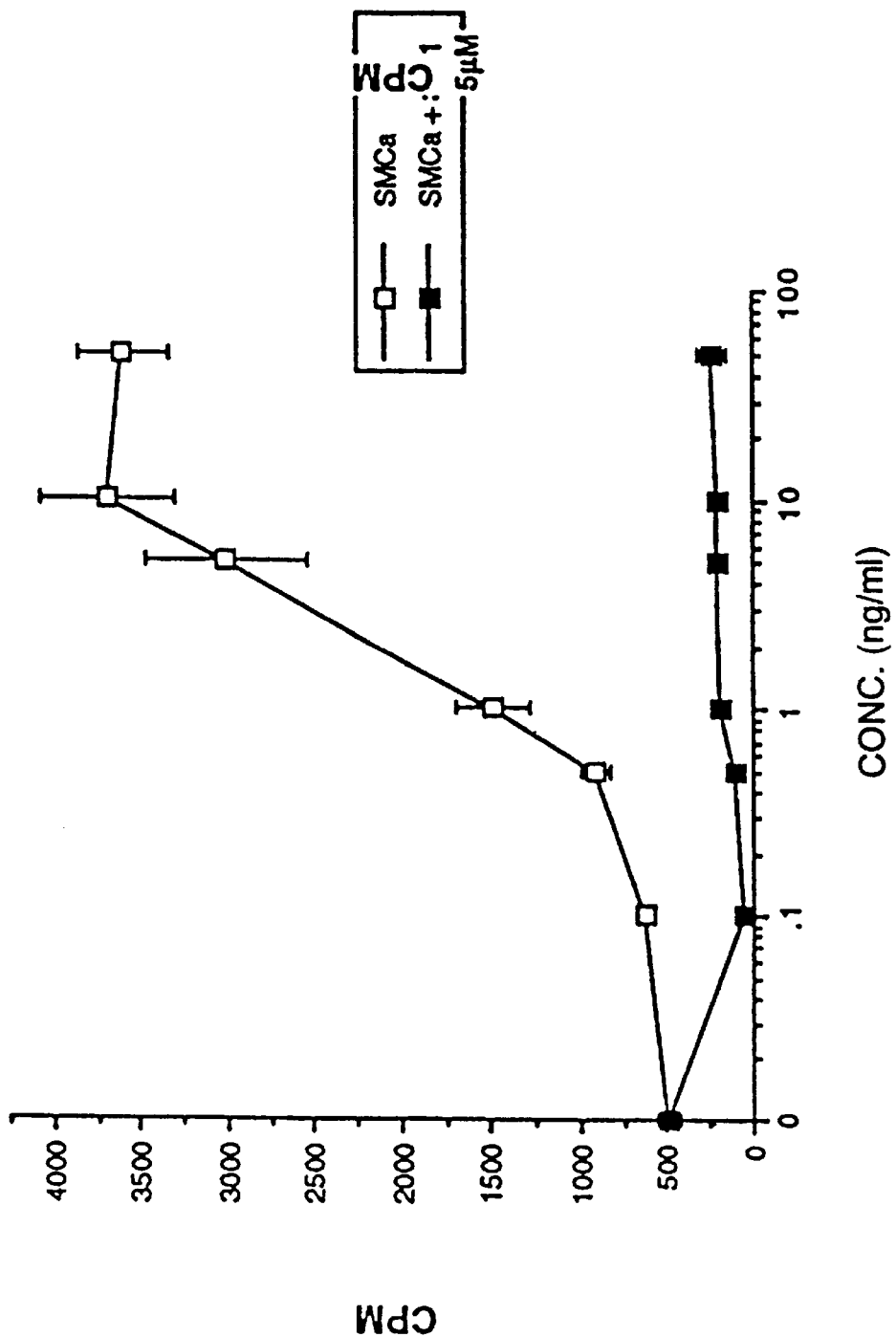
FIG. 5 illustrates that the proliferation of human pulmonary and aoritic smooth muscle cells, induced by PDGFBB, was inhibited by CT-3501 at a concentration of 5 $\mu$M. Quiescent cells were stimulated overnight with PDGFBB, with or without drug and proliferation was measured by tritiated thymidine uptake. This is a predictive model for restenosis.
Figure 5B:
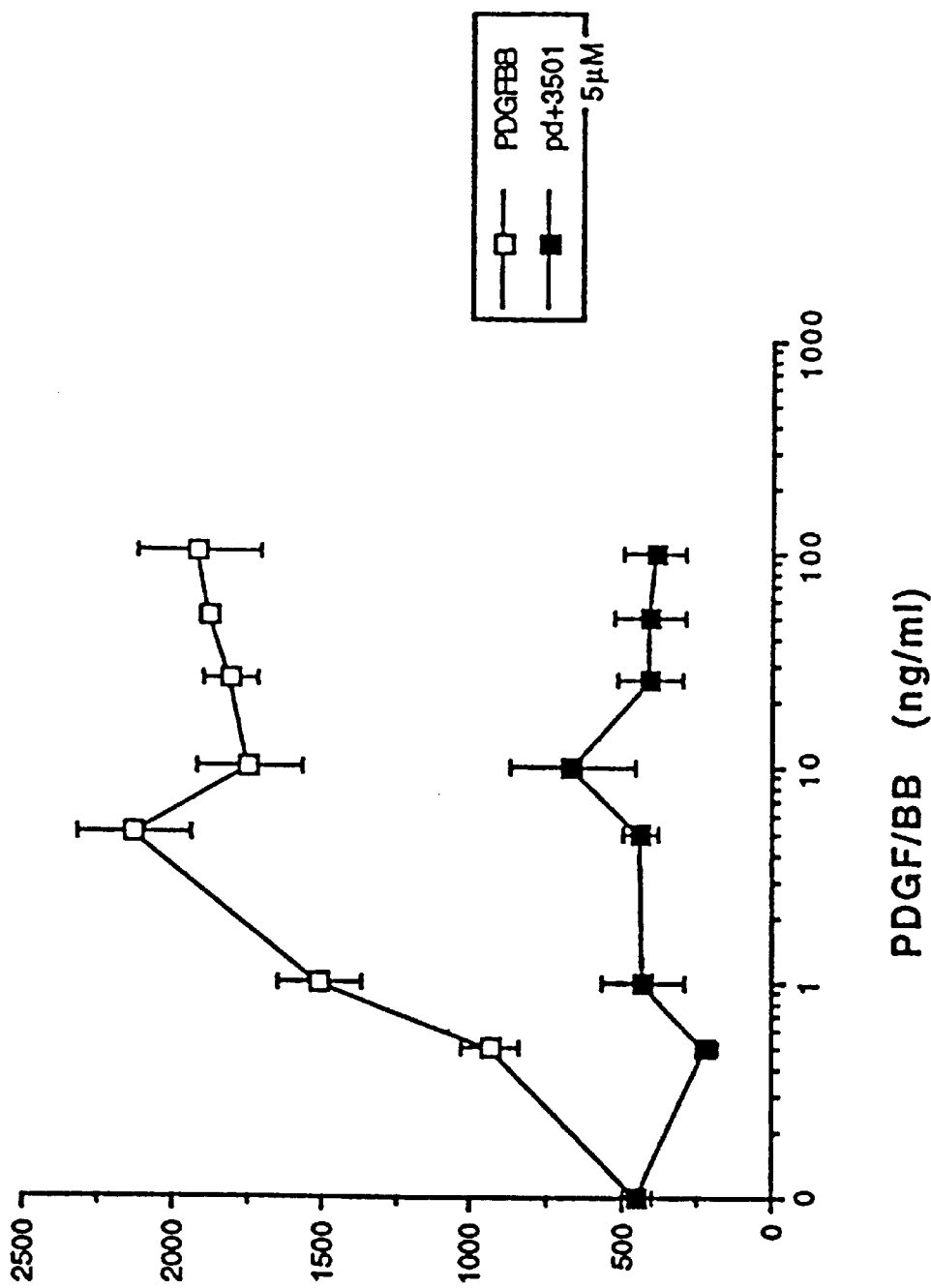

FIG. 5 illustrates that the proliferation of human pulmonary smooth muscle cells, induced by PDGFBB, was inhibited by CT-3501 at a concentration Of 5 $\mu$M. Normal human vascular SMC (aortic and pulmonary) were purchased from Clonetics, San Diego, Calif. and grown in smooth muscle growth medium containing 5% fetal bovine serum. Rest media consisted of DMEM containing 0.5% fetal bovine serum. Quiescent cells were stimulated overnight with PDGFBB with or without drug. Proliferation was measured by tritiated thymidine uptake. This is a predictive model for restenosis.

Figure 13:
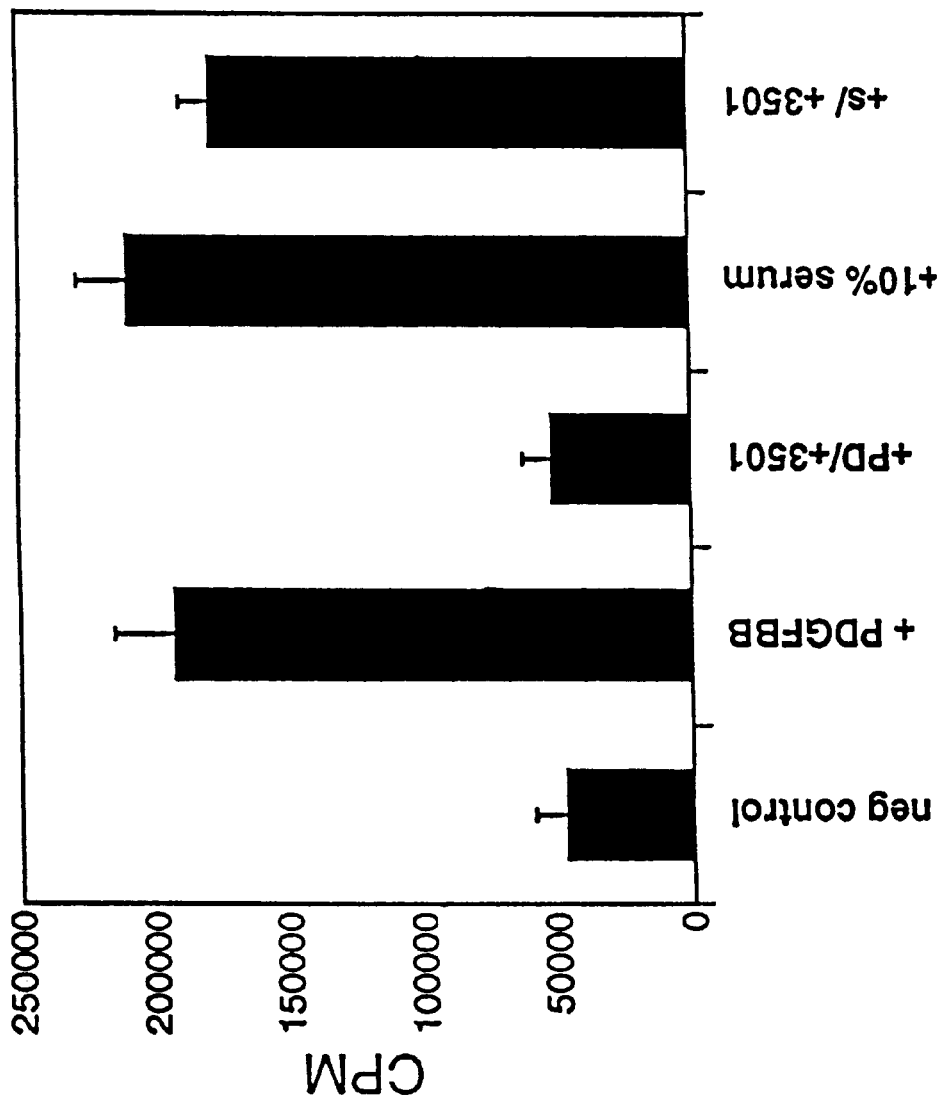
FIG. 13 demonstrates that CT-3501 (500 nM) abolished PDGFBB-induced proliferation of BALB/3T3 cells.

FIG. 13 demonstrates that CT-3501 (500 nM) abolished PDGFBB-induced proliferation of BALB/3T3 cells. However, CT-3501 had a minimal effect on serum induced proliferation. Cells were rested overnight, pre incubated for 1 hr with CT-3501, incubated with PDGFBB, and tritiated-thymidine was added for 24 hours. The cells were harvested and counted using a liquid scintillation counter as a measure of proliferation. This is a predictive model for restenosis and other proliferative disease states associated with PDGF. These data indicate that PDGF proliferative responses are blocked by CT-3501.

EXAMPLE 2

Figure 1:
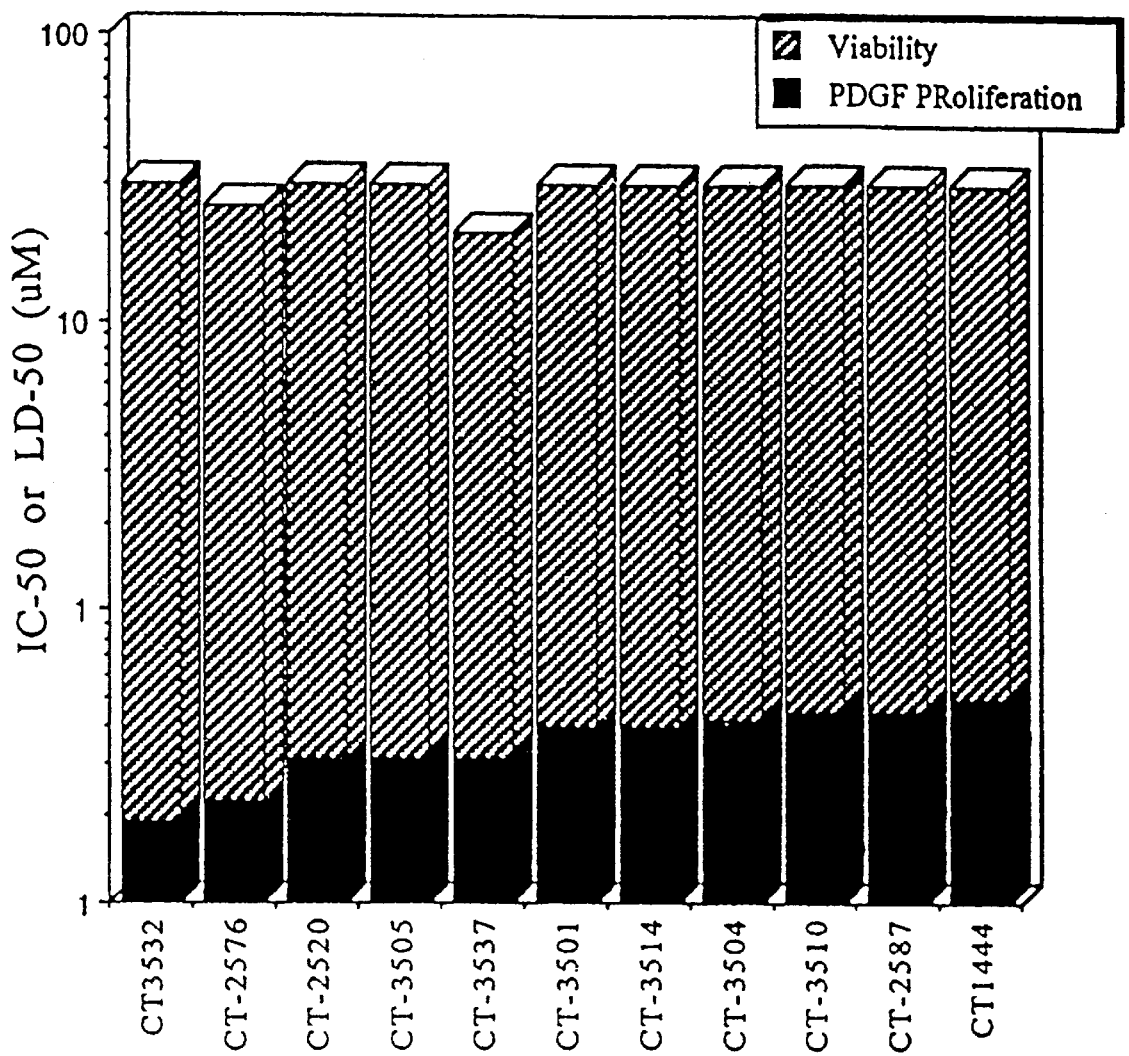
FIG. 1 illustrates data from an experiment where several compounds inhibited PDGFBB-induced proliferation of Balb/3T3 cells. Cells were incubated overnight with PDGFBB (25 ng/ml) and compound. Cell proliferation was determined by tritiated thymidine incorporation. Cell viability was determined using BCECF as an indicator dye. The data show that the compounds inhibited cell proliferation at much lower concentrations than the cytotoxic concentration.
Figure 2A:
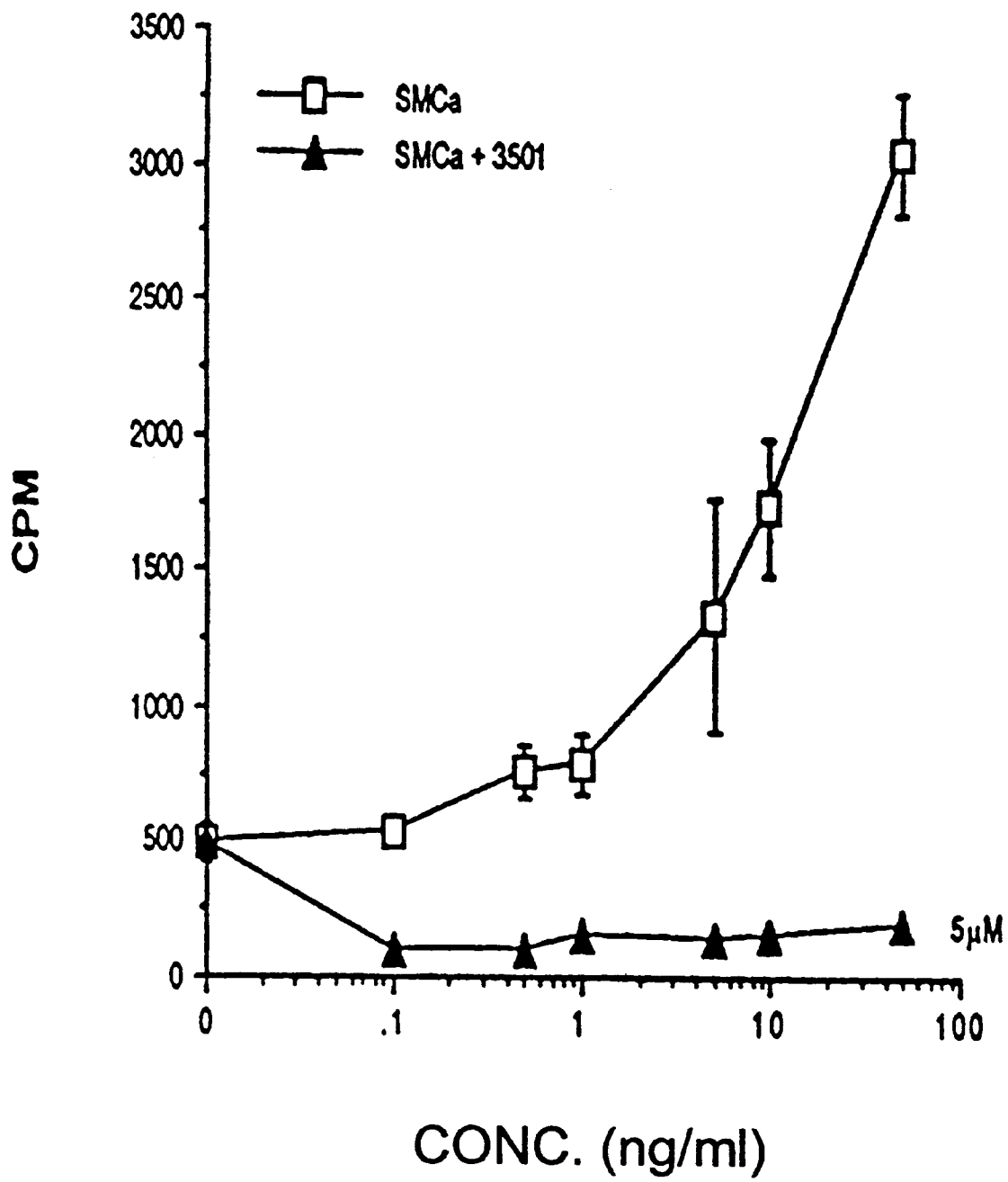
FIG. 2 illustrates data from a group of experiments that are a predictive model for restenosis. CT-3501 (1-[11-(3,4,5-trimethoxybenzylamino)-10-hydroxyundecyl]-3,7-dimethylxanthine) inhibited proliferation of human aortic smooth muscle cells stimulated by aFGF and bFGF. Rested cells were incubated overnight with aFGF or bFGF with or without drug at various indicated concentrations. The cells were pulsed with tritiated thymidine, harvested and counted to assay for proliferation. These data show that the drug inhibited the proliferative effects of FGF and is useful as a therapeutic agent for the treatment or prevention of restenosis and arteriosclerosis.
Figure 2B:
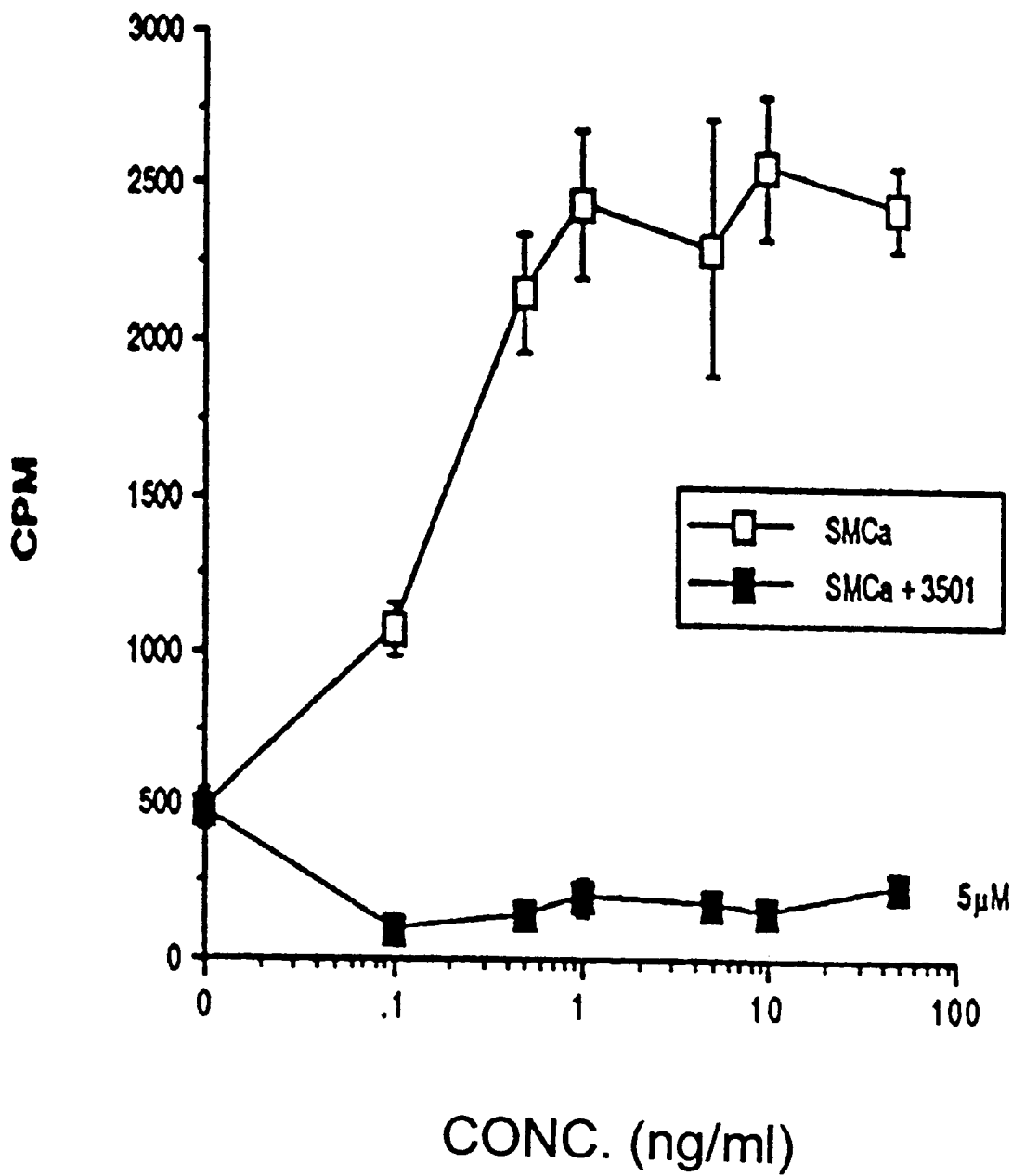

This example illustrates data from a group of experiments that are a predictive model for restenosis. CT-3501 inhibited proliferation of human aortic smooth muscle cells stimulated by aFGF and bFGF. Normal human vascular SMC (aortic and pulmonary) were purchased from Clonetics, San Diego, Calif. and grown in smooth muscle growth medium containing 5% fetal bovine serum. Rest media consisted of DMEM containing 0.5% fetal bovine serum. Rested cells were incubated overnight with aFGF or bFGF (Pepro Tech, Inc., Rocky Hill, N.J.) with or without drug at various indicated concentrations (FIG. 2). The cells were pulsed with tritiated thymidine, harvested and counted to assay for proliferation. These data show that the drug inhibited the proliferative effects of FGF and is useful as a therapeutic agent for treatment or prevention of restenosis and arteriosclerosis.

Figure 4A:
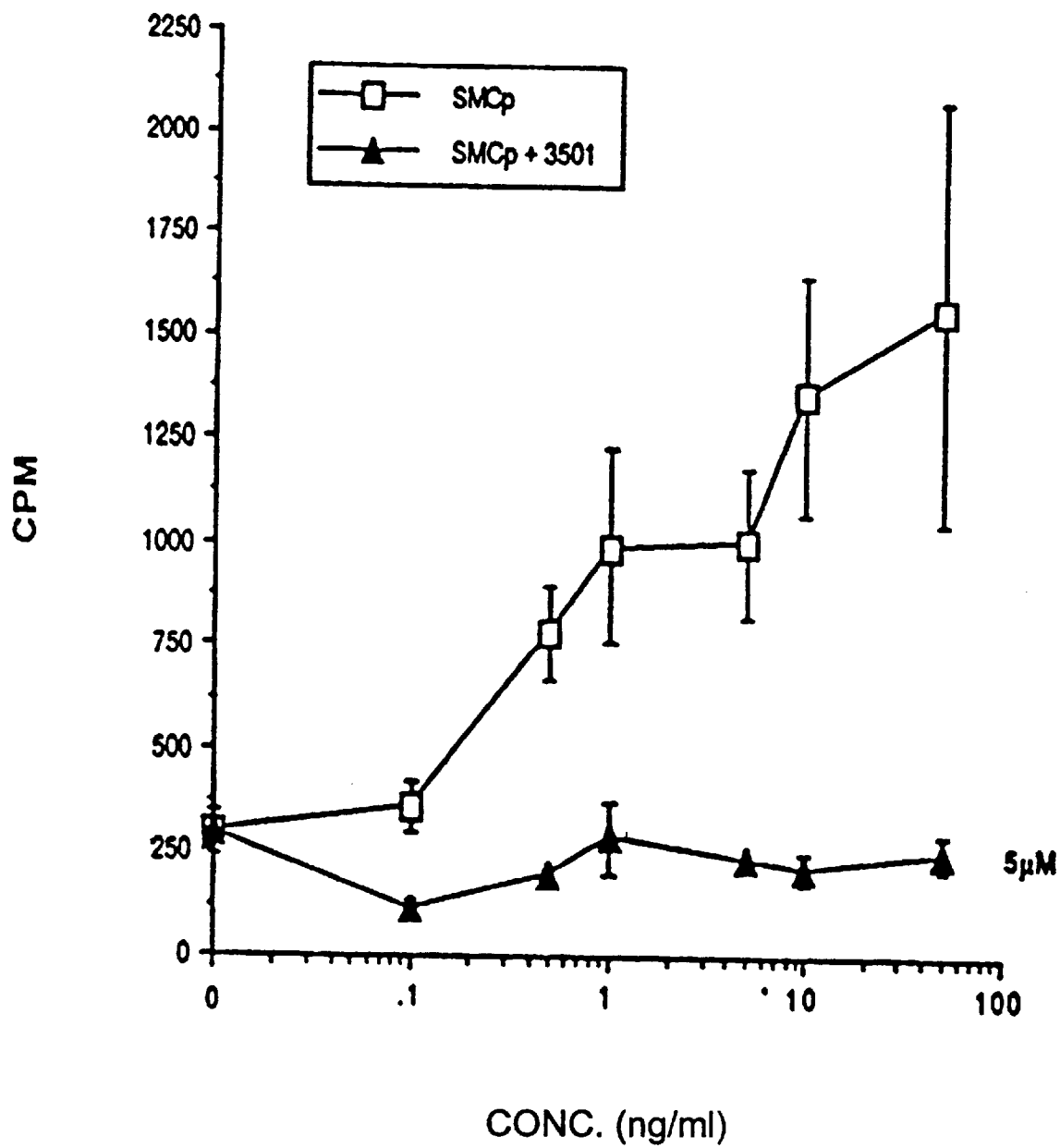
FIG. 4 illustrates that the proliferation of human pulmonary smooth muscle cells stimulated by bFGF and aFGF was inhibited by CT-3501 (1-[11-(3,4,5-trimethoxybenzylamino)-10-hydroxyundecyl]-3,7-dimethylxanthine). Rested cells were stimulated overnight with growth factor with or without drug and all cells were pulsed with tritiated thymidine. FGF induced cellular proliferation in a dose-dependent manner. The drug (5 $\mu$M) inhibited this induced proliferation at all FGF levels. This is a predictive model for angiogenesis, specifically in the context of tumor growth and metastasis.
Figure 4B:
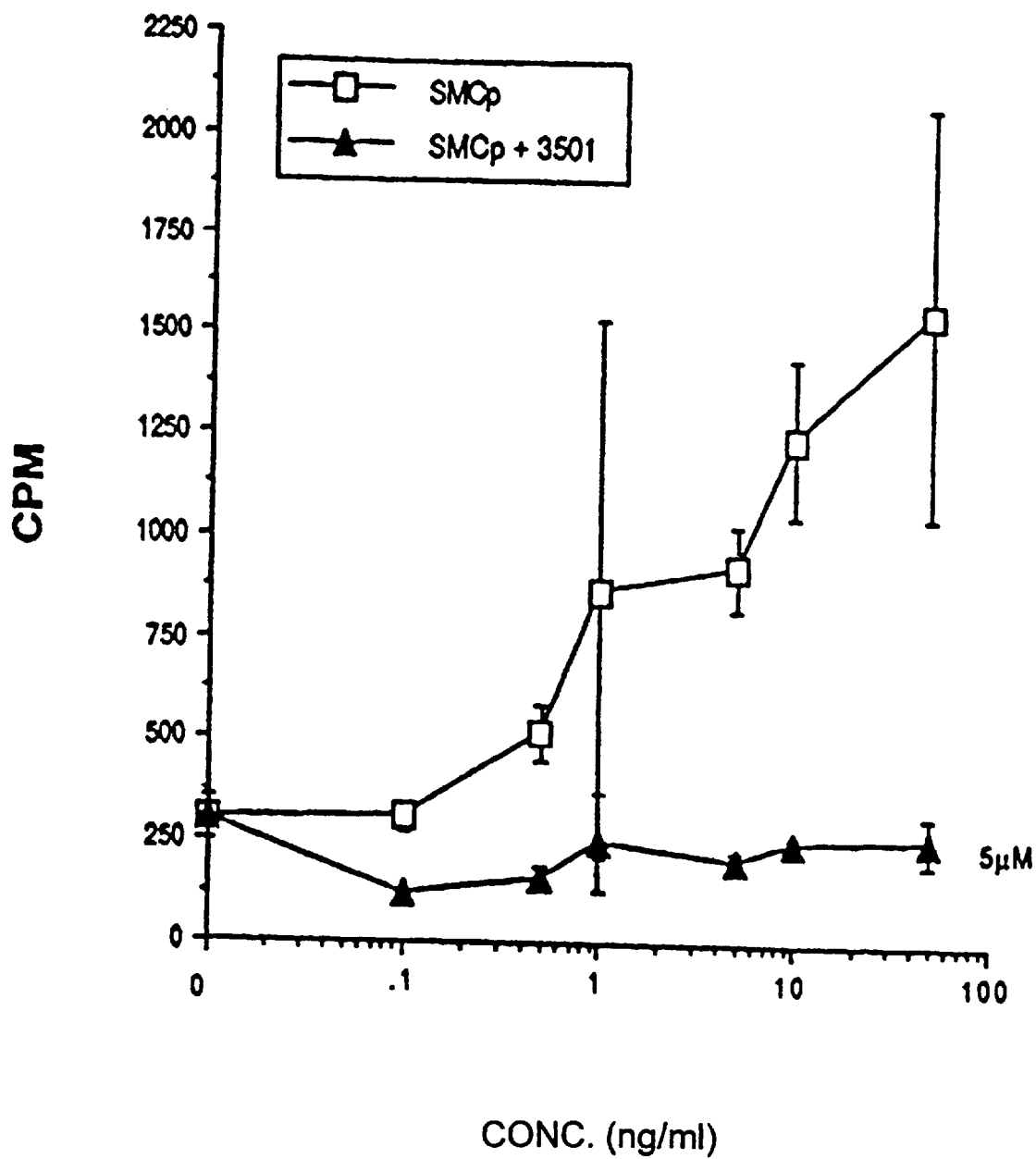

FIG. 4 illustrates that the proliferation of human pulmonary smooth muscle cells stimulated by bFGF and aFGF was inhibited by CT-3501. Normal human vascular SMC (aortic and pulmonary) were purchased from Clonetics, San Diego, Calif. and grown in smooth muscle growth medium containing 5% fetal bovine serum. Rest media consisted of DMEM containing 0.5% fetal bovine serum. Rested cells were stimulated overnight with FGF with or without drug and all cells were pulsed with tritiated thymidine. The drug inhibited cellular proliferation in a dose-dependent manner. This is a predictive model for angiogenesis, specifically in the context of tumor growth and metastasis.

EXAMPLE 3

Figure 6:
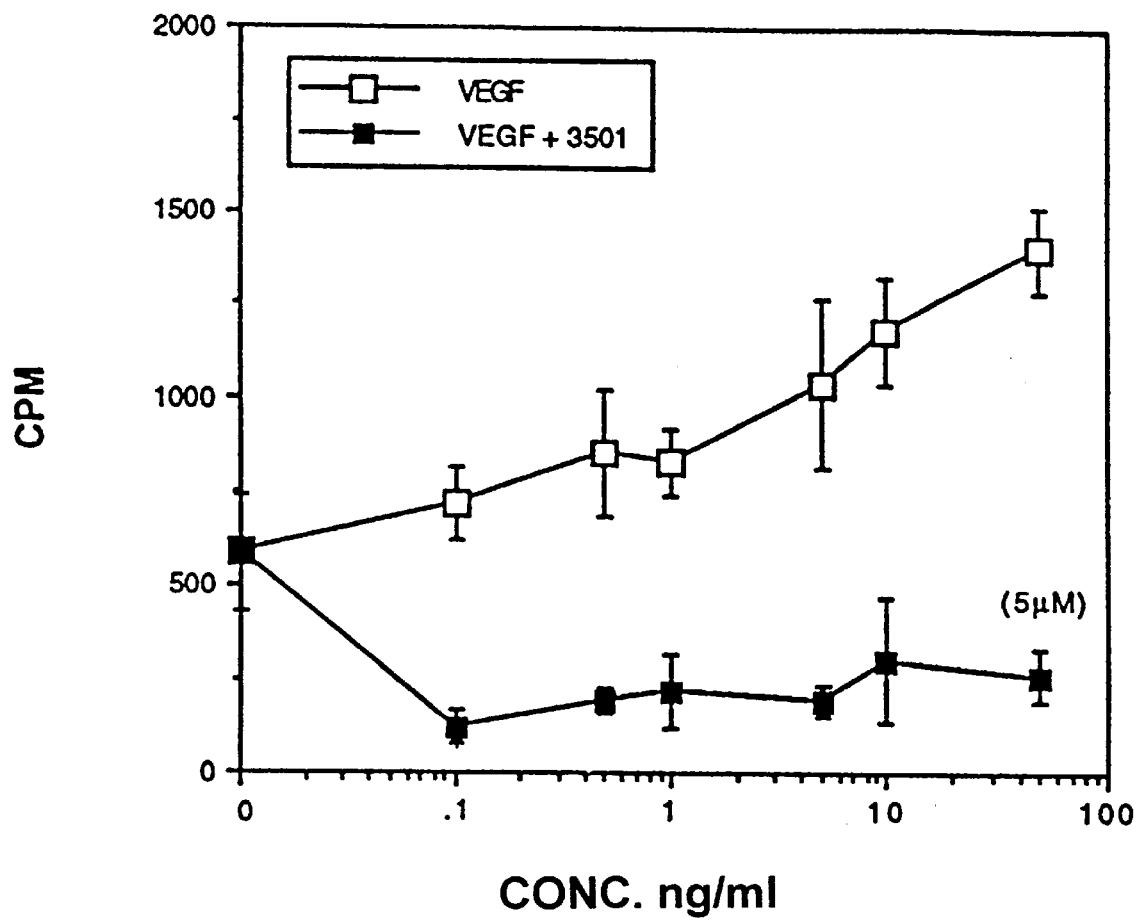
FIG. 6 illustrates that the VEGF induced proliferation of human umbilical vein endothelial cells (HUVEC) was inhibited by CT-3501. HUVEC's were grown for 3 days in 96 well plates, rested overnight in media containing 0.5% fetal bovine serum, and stimulated with VEGF. Proliferation was measured by tritiated thymidine uptake.

This example illustrates that the VEGF induced proliferation of human umbilical vein endothelial cells was inhibited by CT-3501. Normal human umbilical vein endothelial cells (HUVEC) were purchased from Clonetics, grown in endothelial growth medium containing 2% fetal bovine serum and rested in DMEM containing 0.5% fetal bovine serum. HUVEC's were not used past passage 6. HUVEC's were grown for 3 days in 96 well plates, rested overnight in DMEM containing 0.5% fetal bovine serum, stimulated with VEGF (R&D Systems Minneapolis, Minn.). Proliferation was measured by tritiated thymidine uptake. As seen in FIG. 6, the drug inhibited VEGF-induced proliferation in these cells. This is a predictive model for angiogenesis.

Figure 7:
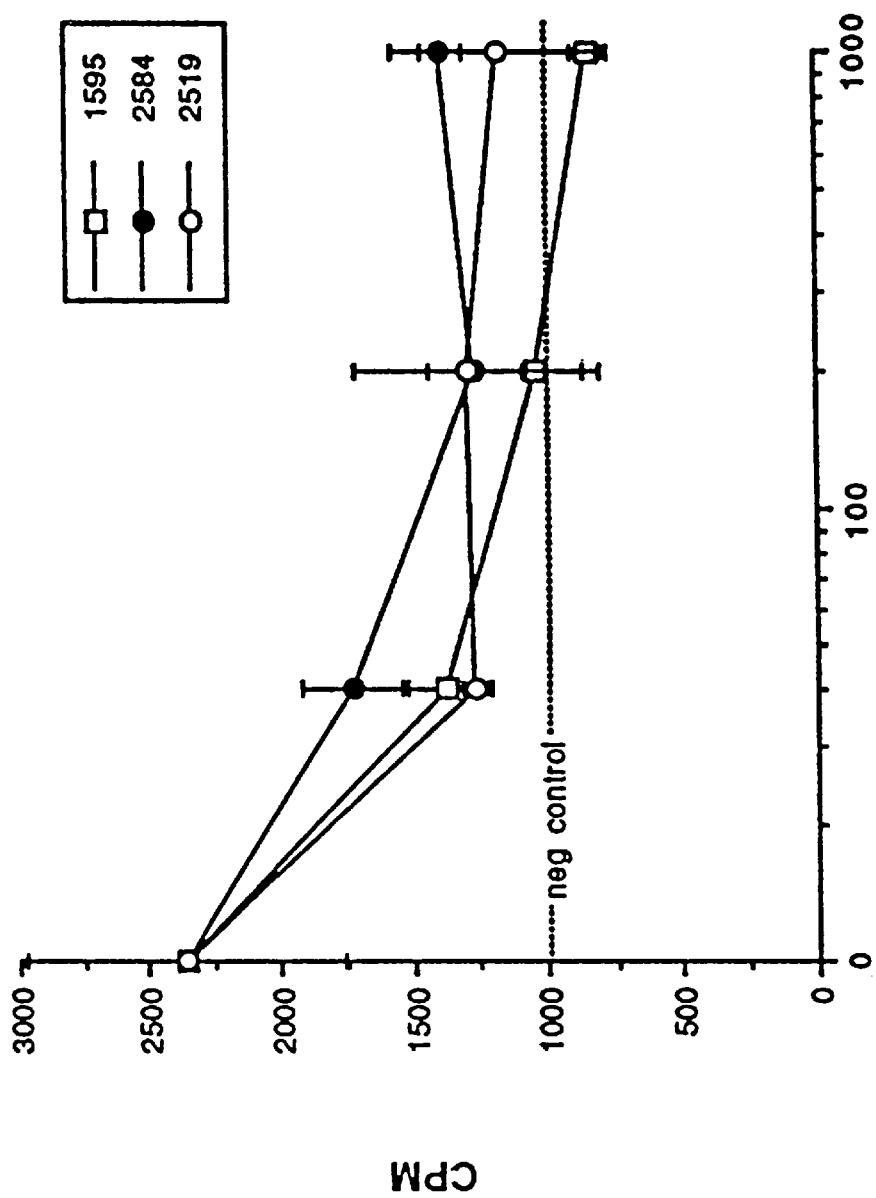
FIG. 7 illustrates that VEGF induced proliferation of HUVEC's is inhibited by compounds CT-1595 (1-(6-chloro-5-oxohexyl)-3,7-dimethylxanthine), CT-2584 (1-(11-dodecylamino-10-hydroxyundecyl)-3,7-dimethylxanthine) and CT-2519(1-(5-isothiocyanatihexyl)-3,7-dimethylxanthine) without inhibiting uninduced proliferation. HUVEC's were grown for 3 days in 96 well plates, rested overnight in media containing 0.5% fetal bovine serum, and stimulated with VEGF. Proliferation was measured by tritiated thymidine uptake.
Figure 8:
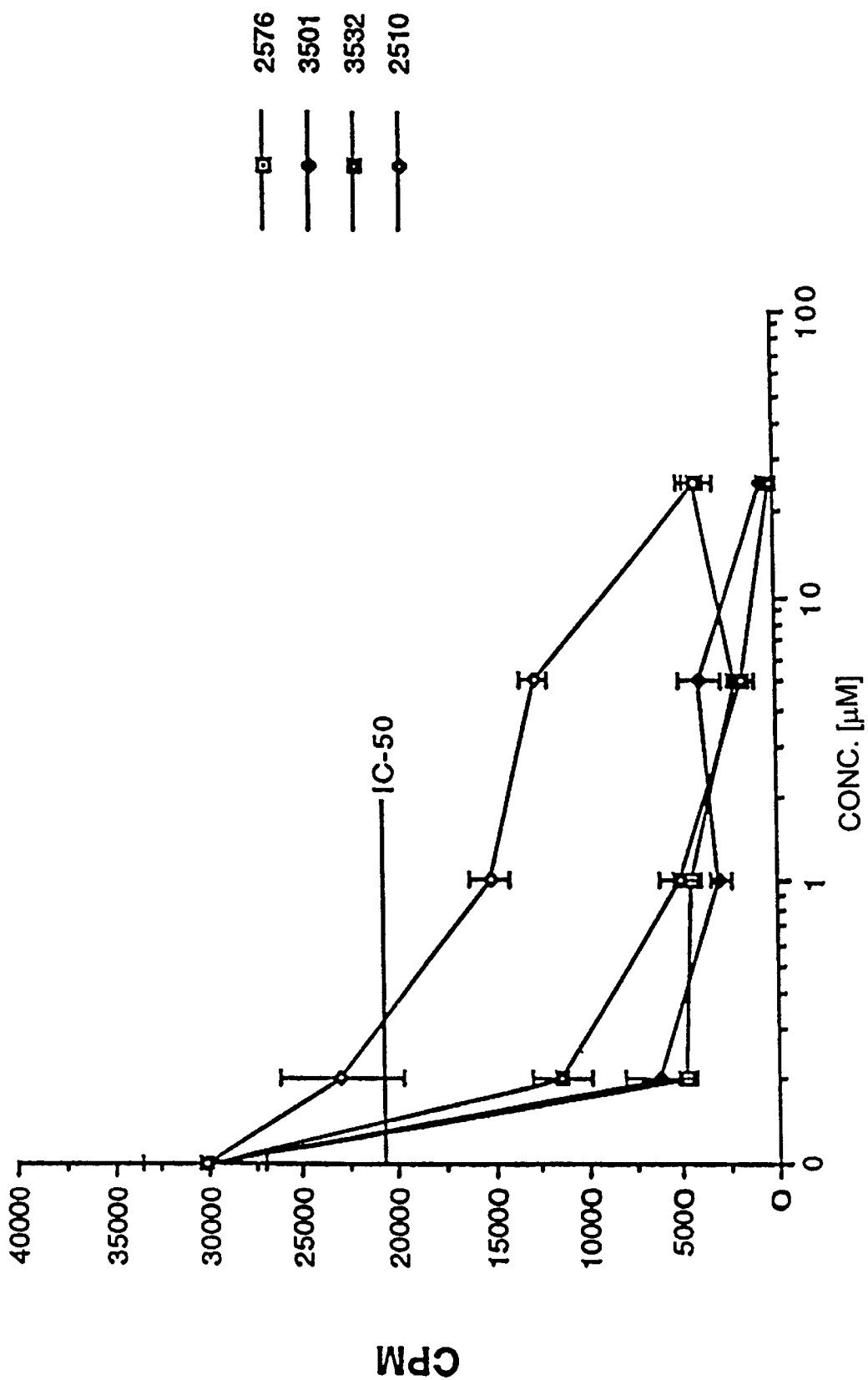
FIG. 8 illustrates data from an experiment with CT-2576 (compound name), CT-3501, CT-3532 (1-[11-(N-octylacetamido)-10-hydroxyundecyl]-3,7-dimethylxanthine), and CT-2510 (1-(oxoundecyl)-3,7-dimethylxanthine) that illustrates inhibition of EGF-induced proliferation of Swiss 3T3 cells. Cells were rested overnight in media containing 0.2% serum and stimulated with 10 ng/ml EGF.

FIG. 7 illustrates that VEGF induced proliferation of HUVEC's is inhibited by compounds CT-1595, CT-2584 and CT-2519 without inhibiting uninduced proliferation. HUVEC's were grown for 3 days in 96 well plates, rested overnight in media containing 0.5% fetal bovine serum, and stimulated with VEGF. Proliferation was measured by tritiated thymidine uptake. As seen in FIG. 7, the compounds inhibited VEGF-induced proliferation in these cells. This is a predictive model for angiogenesis.

EXAMPLE 4

This example illustrates data from an experiment with CT-2576, CT-3501, CT-3532, and CT-2510 that illustrates inhibition of EGF-induced proliferation of Swiss/3T3 cells. Cells were rested overnight in media containing 0.2% serum and stimulated with 10 ng/ml EGF (R&D Systems Minneapolis, Minn.). As seen in FIG. 8, all of the compounds inhibited EGF-induced proliferation in a dose-dependent manner, with CT-2510 being the least potent of the compounds tested. These data show that the compounds tested block EGF-mediated proliferative activity which is an important determinant in inflammation, cancer cell growth and metastasis.

EXAMPLE 5

Figure 9:
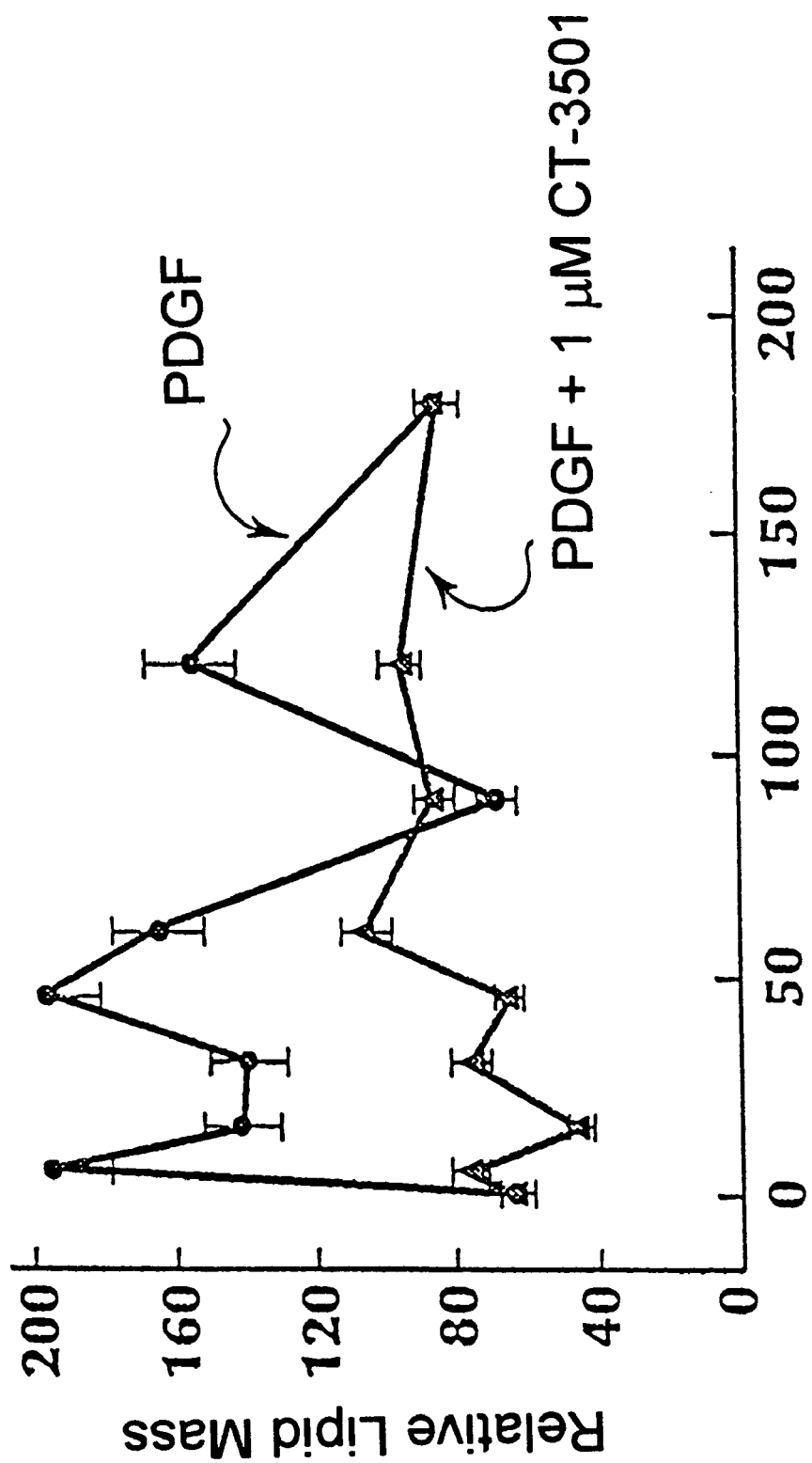
FIG. 9 illustrates a comparison of PA concentration in relative lipid mass at various time after stimulation of Balb/3T3 cells with PDGFBB with and without CT-3501. Cells were rested overnight and pulsed with 25 ng/ml PDGFBB in the presence or absence of 1 $\mu$M CT-3501. Cells were fixed in ice-cold methanol and Folch extracted. The phospholipids were separated by HPLC. Several PA species were observed, including "late migrating PA" which include, for example, 1-o-octadecanyl 2-oleoyl PA (687), 1-oleoyl 2-linoleoyl PA (697 or 698), 1-o-octadecanyl 2-linoleoyl PA (681), 1-o-octadecanyl-9,12-dienyl 2-linoleoyl PA (679), 1-myristoyl 2-oleoyl PA (645), and 1-o-myristoyl 2-stearoyl PA (633). PA species were identified using standards and fast atom bombardment mass spectrometry.

This example illustrates a comparison of PA concentration in relative lipid mass at various time after stimulation of Balb/3T3 cells with PDGFBB with and without CT-3501. Cells were rested overnight and pulsed with 25 ng/ml PDGFBB in the presence or absence of 1 μM CT-3501. Cells were fixed in ice-cold methanol and Folch extracted, the phospholipids were separated by HPLC. Several PA species were observed, including "late migrating PA" which include, for example, 1-o-octadecanyl 2-oleoyl PA (687), 1-oleoyl 2-linoleoyl PA (697 or 698), 1-o-octadecanyl 2-linoleoyl PA (681), 1-o-octadecanyl-9,12-dienyl 2-linoleoyl PA (679), 1-myristoyl 2-oleoyl PA (645), and 1-o-myristoyl 2-stearoyl PA (633). PA species were identified using standards and fast atom bombardment mass spectrometry (FIG. 9).

Figure 10:
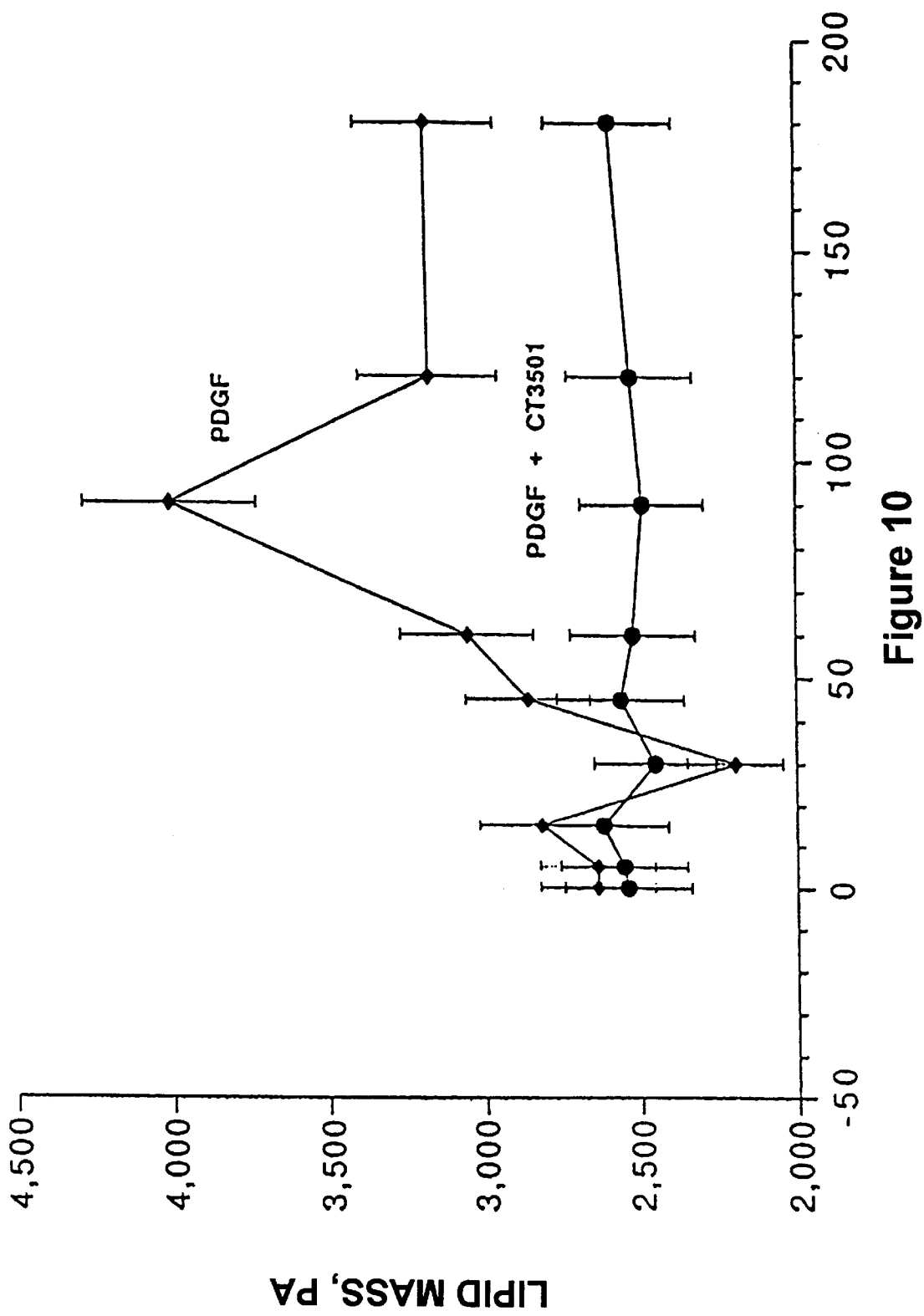
FIG. 10 illustrates differential induction of "early" PA species in Balb/3T3 cells induced by PDGFBB and their inhibition by CT-3501. Cells were rested overnight and pulsed with 25 ng/ml PDGFBB in the presence or absence of 1 $\mu$M CT-3501. Cells were fixed in ice-cold methanol and Folch extracted. The phospholipids were separated by HPLC. Several PA species were observed, including "early migrating PA" which include, for example, 1,2-sn-dilinoleoyl PA (695), 1-oleoyl 2-linoleoyl PA (697), 1,2-dioleoyl PA (699), 1-stearoyl 2-linoleoyl PA (699), and 1-stearoyl 2-oleoyl PA(701). PA species were identified using standards and fast atom bombardment mass spectrometry.
Figure 11A:
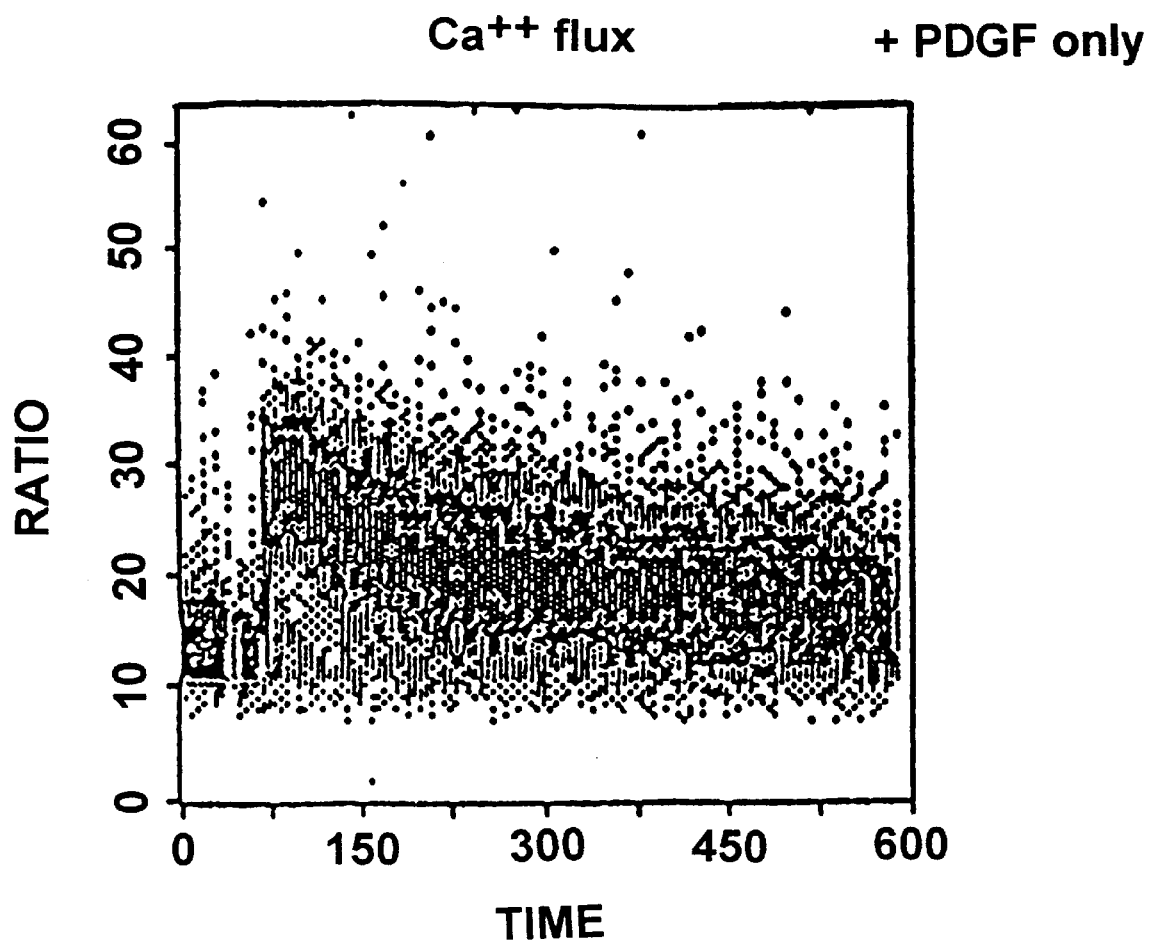
FIG. 11 shows three panels from a cell sorting experiment of 3T3 cells stimulated with PDGFBB with or without compound CT-1509 (1-(6,7-cis-oxidononyl)-3,7-dimethylxanthine (10:1 cis:trans)). Panel a shows that calcium mobilization was induced by PDGFBB and was unaffected by CT-1509 at 5 $\mu$M (panel b). Panel c illustrates that cells incubated with CT-1509 did not respond to diluent, but were capable of fluxing calcium in response to ionomycin. Cells were rested overnight in serum free media, incubated for 30 minutes in 10 $\mu$M Indo-1-AM (Molecular Probes, Junction City, OR) at 37° C. and maintained on ice until brought to 37° C. immediately prior to use. Indo-1 ratios (calcium mobilization) were determined with a Coulter Epics® elite flow cytometer utilizing a HeCd laser. These data show that CT-1509 has no effect on PDGF-induced calcium mobilization. Therefore, the activity of such compounds is specific.
Figure 11B:
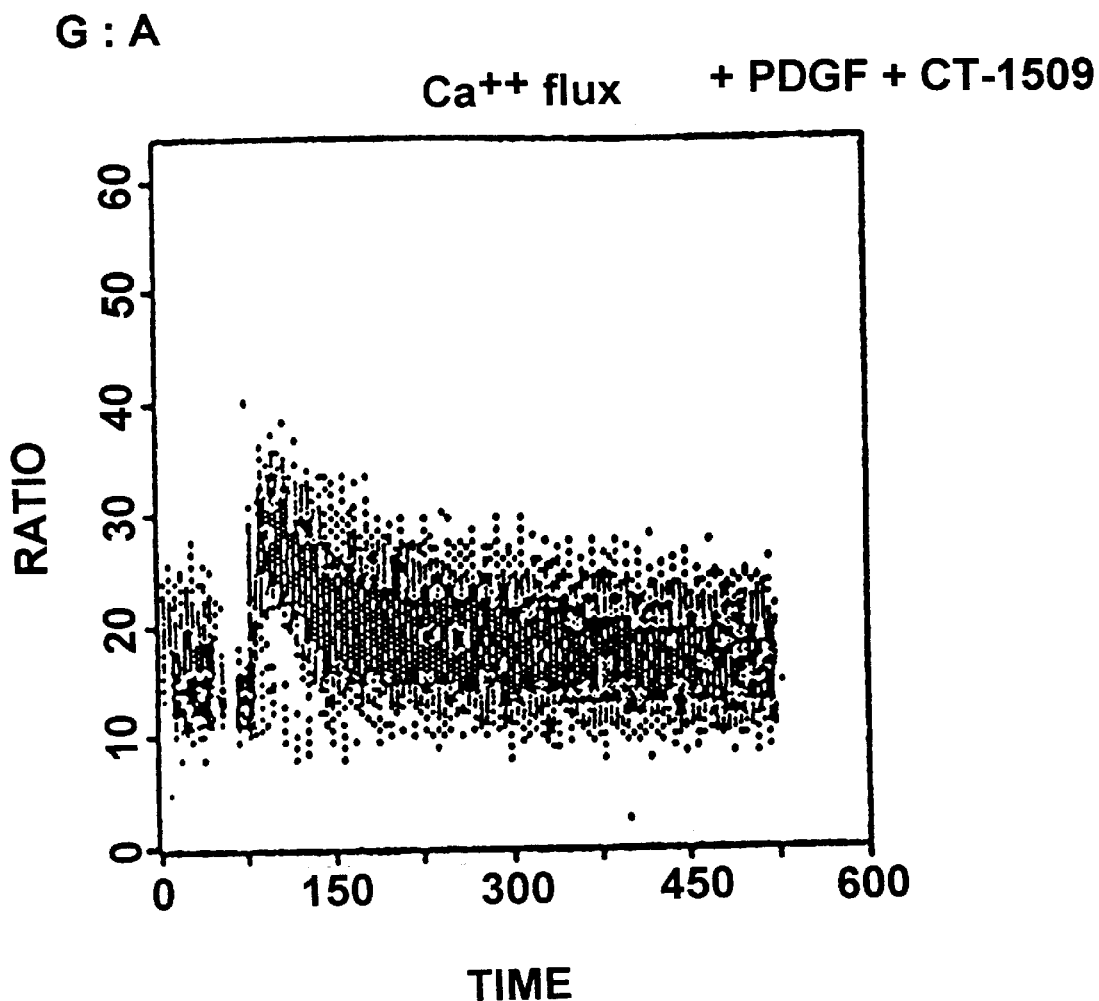
Figure 11C:
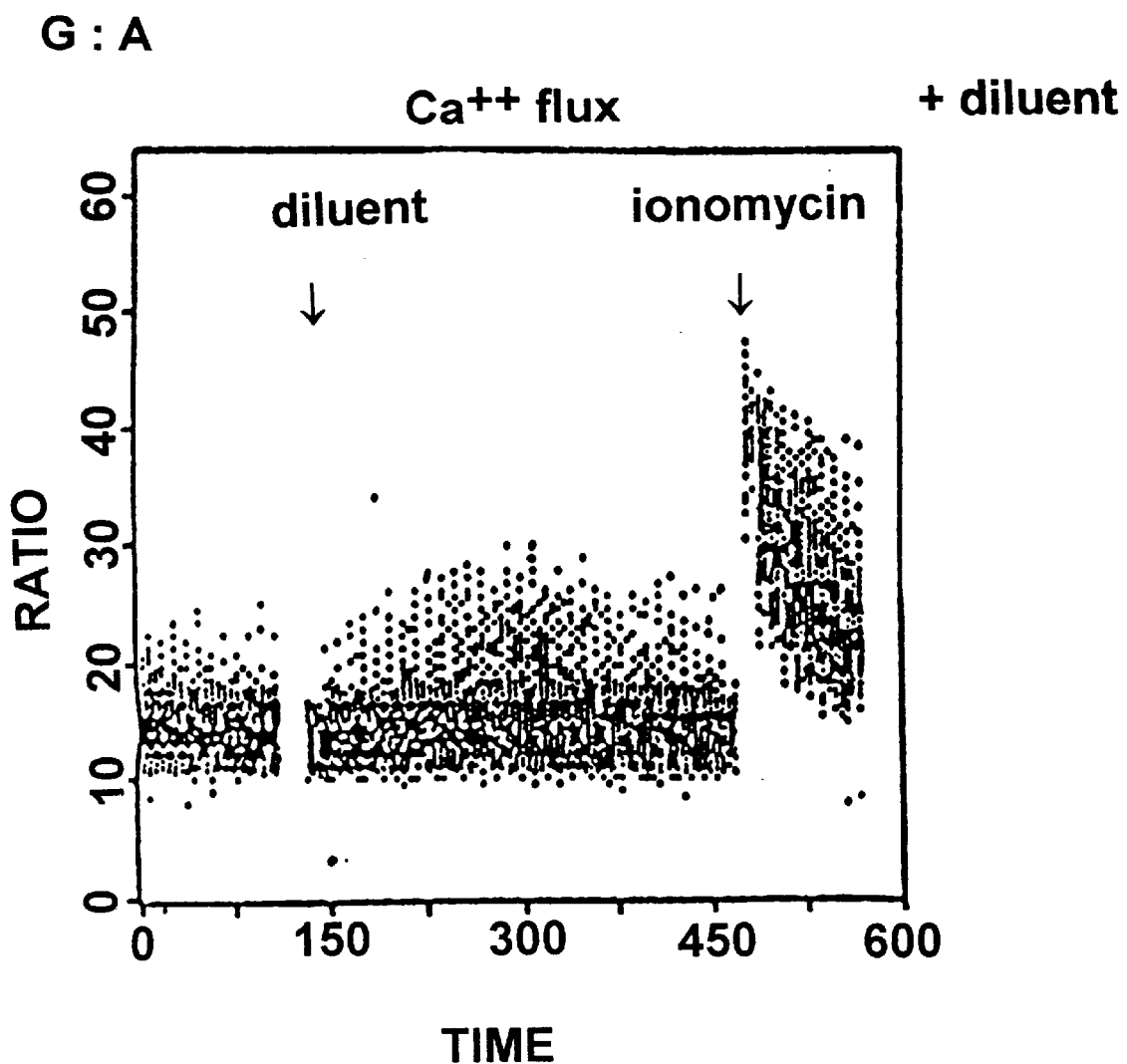

FIG. 10 illustrates differential induction of "early" PA species in Balb/3T3 cells induced by PDGFBB and their inhibition by CT-3501. Cells were rested overnight and pulsed with 25 ng/ml PDGFBB in the presence or absence of 1 μM CT-3501. Cells were fixed in ice-cold methanol and Folch extracted, the phospholipids were separated by HPLC. Several PA species were observed, including "early migrating PA" which include, for example, 1,2-sn-dilinoleoyl PA (695), 1-oleoyl 2-linoleoyl PA (697), 1,2-dioleoyl PA (699), 1-stearoyl 2-linoleoyl PA (699), and 1-stearoyl 2-oleoyl PA(701). PA species were identified using standards and fast atom bombardment mass spectrometry.

EXAMPLE 6

This example illustrates a cell sorting experiment of 3T3 cells stimulated with PDGFBB with or without compound CT-1509. FIG. 11, panel a shows that calcium mobilization was induced by PDGFBB and was unaffected by CT-1509 at 5 μM (panel b). Panel c illustrates that cells incubated with CT-1509 did not respond to diluent, but were capable of fluxing calcium in response to ionomycin. Cells were rested overnight in serum free media, incubated for 30 minutes in 10 μM Indo-1-AM (Molecular Probes, Junction City, Oreg.) at 37° C. and maintained on ice until brought to 37° C. immediately prior to use. Indo-1ratios (calcium mobilization) were determined with a Coulter Epics® elite flow cytometer utilizing a HeCd laser. These data show that CT-1509 has no effect on PDGF-induced calcium mobilization. Therefore, the activity of such compounds is specific.

EXAMPLE 7

Figure 12:
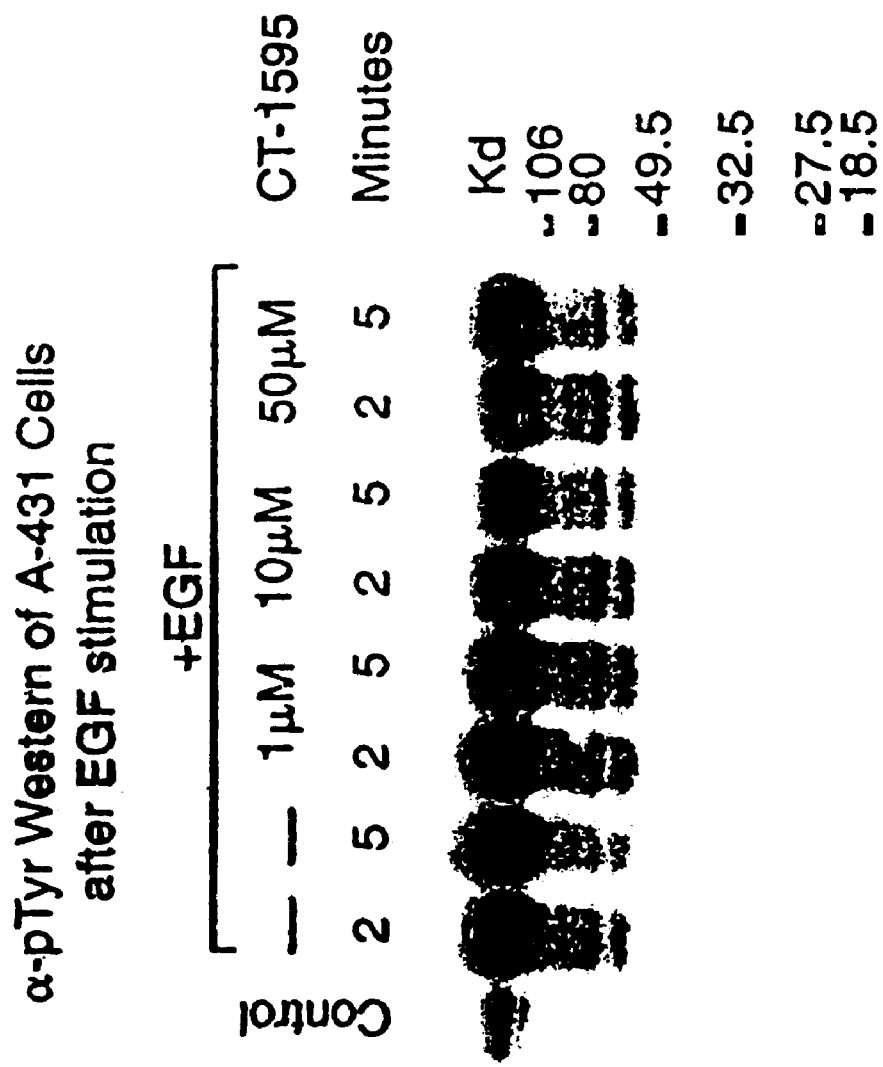
FIG. 12 illustrates that EGF-induced phosphorylation of EGF receptor is uneffected by compound CT-1595. A431 cells were rested overnight in serum free media, stimulated with 1 nM EGF with or without CT-1595, lysed and run on 4–20% PAGE, transferred and blotted with an anti-phosphotyrosine antibody (Upstate Biotechnology Inc.). Proteins containing phosphotyrosine were visualized with $^{125}$I-protein A (Amersham Life Sciences, Arlington Heights, Ill.). Similar results are seen with BALB/3T3 cells stimulated with PDGFBB. These data illustrate the specificity of compounds, such as CT-1595.

This example illustrates that EGF-induced phosphorylation of EGF receptor is uneffected by compound CT-1595 (FIG. 12). A431 cells were rested overnight in serum free media, stimulated with 1nM EGF with or without CT-1595, lysed and run on 4–20% PAGE, transferred and blotted with an anti-phosphotyrosine antibody (Upstate Biotechnology Inc.). Proteins containing phosphotyrosine were visualized with $^{125}$I-protein A (Amersham Life Sciences, Arlington Heights, Ill.). Similar results are seen with BALB/3T3 cells stimulated with PDGFBB. These data illustrate the specificity of compounds such as CT-1595.

FIG. 14 illustrates data from an experiment showing that compound CT-3501 blocked a PDGF-induced proliferative signal in HepG2 cells transfected with portions of the PDGF receptor shown in the panel on the left. Cells transfected with receptor capable of binding phospholipase c gamma or phosphotidylinositol-3-kinase only were inhibited by CT-3501 (500 nM).

EXAMPLE 8

This example illustrates a comparison CT-3501 inhibiting invasiveness of 3LL cells (FIG. 17, left panel) and VEGF-induced migration of HUVEC's with three dose levels of CT-3501. Lewis lung carcinoma cells (3LL) were maintained in RPMI media containing 10% fetal calf serum. Cells were placed into a Matrigel invasion assay system (Becton Dickinson, Bedford, Mass.) and assessed for invasiveness (3LL cells) or VEGF induced migration (HUVEC's) with or without CT-3501 after 48 hours. CT-3501 decreased invasiveness at a concentration of 5 μM, and inhibited VEGF-induced migration in a dose-response manner. These data indicate that CT-3501 will block VEGF-mediated proliferative events which have been associated with cancer cell metastasis, invasiveness and angiogenesis.

EXAMPLE 9

This example illustrates that various species of PA and lyso-Phosphatidic acid induced Balb/3T3 cells to proliferate and that this proliferation is inhibited by CT-3501 at a concentration of 500 nM (FIGS. 16a–e). The various species of PA are indicated on each figure. Phosphatidic Acid (PA's) derivatives were synthesized or purchased from Avanti Polar-Lipids, Inc., Alabaster, Ala. PA's were dissolved in chloroform, dried under $N_2$ and stored under Argon. PA's were reconstituted in phosphate buffered saline containing 0.1% fatty-acid free bovine serum albumin by sonication on ice. As shown in FIGS. 16a–e, addition of various types of PA's, including L-a PA (derived from natural sources), 1,2 dilauroyl-sn-glycero-3-phosphate, 1,2 dioleoyl-sn-glycero-3-phosphate, 1-stearolyl-2-aracidonyl-sn-glycero-3-phosphate and 1-alkyl-oleoyl-2-oleoyl-PA, were mitogenic in Balb/3T3 cells. All of the mitogenic responses induced through the addition of these PA's to the cells were inhibited by CT-3501. Thus, CT-3501 block the formation of and the activity of specific PA species.

FIGS. 17–21 illustrate a mass spectrograph of a designated lipid fraction isolated from Balb 3T3 fibroblasts stimulated with PDGF (25 ng/ml) in the presence or absence of compound CT-3501. Specifically, FIG. 17 shows a mass spec of a PA HPLC peak 5 seconds after stimulation with PDGF including the 1-o-alkyl C18 PA derivatives including 697 (1-o-'en-octadeca-9,12-dienyl 2 linoleoyl PA), 681 (1-o-octadeca-9,12-dienyl 2-linoleoyl PA), 683 (1-o-octadeca-9-enyl 2-linoleoyl 2-stearoyl PA), and related PA derivatives with C20 sn-2 components such as 703 (1-o-octadeca-9,12-dienyl 2-arachidonoyl PA), and 707 (1-o-octadeca-9-enyl 2-arachidonoyl PA). FIG. 18 shows that synthesis of Type 1B PA species (especially 679 and 681) was maintained after 15 seconds of stimulation with PDGF. Type 1B PA species include, for example, 1-o-octadecanyl 2-oleoyl PA (687), 1-oleoyl 2-linoleoyl PA (697 or 698), 1-o-octadecanyl 2-linoleoyl PA (681), 1-o-octadecanyl-9,12-dienyl 2-linoleoyl PA (679), 1-myristoyl 2-oleoyl PA (645), and 1-o-myristoyl 2-stearoyl PA (633) PA species. FIG. 19 further shows the 15 second stimulation maintaining the Type 1B PA species and, in addition, 673 (1-palmitoyl, 2-oleoyl PA) and 671 (1-palmitoyl, 2-linoleoyl PA) PA species.

In FIG. 20, 5 μM CT-3501 was added. FIG. 20 is the 5 second time point and shows (in comparison to FIG. 17 without drug) that whereas synthesis of 1-stearoyl 2-linoleoyl PA is maintained, the synthesis of the other PA species was greatly reduced. Similarly, in FIG. 21, PA species with masses from 675 to 740 were all but obliterated by CT-3501 treatment, but the synthesis of saturated palmitoyl and myristoyl PA's was maintained or increased (675 is 1-palmitoyl, 2-stearoyl PA or 1-stearoyl, 2-palmitoyl PA, 647 is 1-palmitoyl, 2-palmitoyl PA or 1-myristoyl, 2-stearoyl PA, and 619 is 1-myristoyl, 2-palmitoyl PA).

We claim:

1. A method for treating atherogenesis, vasculopathies due to atherogenesis, coronary artery disease, restenosis, or atherosclerosis comprising administering a compound that inhibits signal transduction through cellular accumulation of non-arachidonyl phosphatidic acid (PA) selected from the group consisting of 1-o-octadecanyl 2-oleoyl PA (687), 1-oleoyl 2-linoleoyl PA (697 or 698) 1-o-octadecanyl 2-linoleoyl PA (681), 1-o-octadecanyl-9,12-dienyl 2-linoleoyl PA (679), 1-myristoyl 2oleoyl PA (645), 1-o-myristoyl 2-stearoyl PA (633), 1,2-sn-dilinoleoyl PA (695), 1-oleoyl 2-linoleoyl PA (697), 1-stearoyl 2-oleoyl PA (701), 1-o-oleoyl 2-20:4 PA (707), 1-o-lineleoyl 2-20:4 PA (705), 1-o-linoleoyl 2-20:5 PA (703), and combinations thereof, the compound having a formula:

(X)j–(core moiety), wherein j is an integer from one to three, the core moiety comprises at least one five to seven-membered substituted or unsubstituted heterocyclic ring and X is a racemic mixture or R or S enantiomer of:

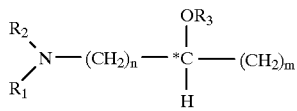

wherein * C is a chiral carbon atom n is an integer from one to four, wherein one or more carbon atoms in $(CH_2)_n$ may be substituted by a keto or hydroxy group, m is an integer from one to fourteen, $R_1$ and $R_2$ are independently H, a straight or branched chain alkane or alkene of up to twelve carbon atoms in length, —$(CH_2)_m R_5$, or $R_1$ and $R_2$ form a cyclo saturated or unsaturated aromatic ring or substituted aromatic ring having from four to eight carbon atoms and including the nitrogen atom within the ring and $R_3$ is H or $C_{1-3}$, and $R_5$ is a substitute or unsubstituted aryl group wherein the substituted aryl group is mono, di or tri substituted with hydroxy, chloro, fluoro, bromo, or alkoxy ($C_{1-6}$) substituents, or

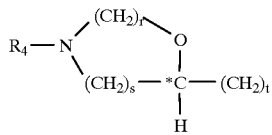

wherein $R_4$ is a hydrogen or a straight or branched chain alkane or alkene of up to eight carbon atoms in length, —$(CH_2)_m R_5$, or $R_4$ forms a cyclo saturated or unsaturated aromatic ring or substituted aromatic ring having from four to eight carbon atoms and including the nitrogen atom within the ring, r and s are independently integers from one to four, the sum (r+s) is not greater than five, wherein one or more carbon atoms in $(CH_2)_q$ or $(CH_2)_p$ may be substituted by a keto or hydroxy group, t is an integer from one to fourteen, and $R_5$ is a substituted or unsubstituted aryl group wherein the substituted aryl group is mono, di or tri substituted with hydroxy, chloro, fluoro, bromo, or alkoxy ($C_{1-6}$) substituents, or X is independently hydrogen, $C_{1-6}$ alkyl, a resolved enantiomer ω-1 secondary alcohol-substituted alkyl ($C_{5-8}$) substantially free of the other enantiomer, or a branched —$(CH_2)_a$—$CHR_6$—$(CH_2)_b$—$R_7$, wherein a is an integer from about 4 to about 12, b is an integer from 0 to 4, $R_6$ is an enantiomer (R or S) or racemic mixture ($C_{1-6}$)alkyl, or alkenyl, and $R_7$ is a hydroxy, keto, cyano, chloro, iodo, flouro, or chloro group, with the proviso that at least one X is the resolved ω-1 secondary alcohol-substituted alkyl.

2. A method for suppressing accelerated atherogenesis, comprising administering a compound that inhibits signal transduction through cellular accumulation of non-arachidonyl phosphatidic acid (PA) selected from the group consisting of 1-o-octadecanyl 2-oleoyl PA, 1-oleoyl 2-linoleoyl PA, 1-o-octadecanyl 2-linoleoyl PA, 1-o-octadecanyl-9,12-dienyl 2-linoleoyl PA, 1-myristoyl 2-oleoyl PA, 1-o-myristoyl 2-stearoyl PA, 1,2-sn-dilinoleoyl PA, 1-oleoyl 2-linoleoyl PA, 1-stearoyl 2-oleoyl PA, 1-o-oleoyl 2-20:4 PA, 1-o-linoleoyl 2-20:4 PA, 1-o-linoleoyl 2-20:5 PA, and combinations thereof, the compound having a formula:

(X)j–(core moiety), wherein j is an integer from one to three, the core moiety comprises at least one five to seven-membered substituted or unsubstituted heterocyclic ring and X is a racemic mixture or R or S enantiomer of:

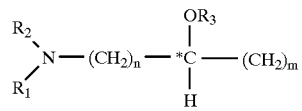

wherein * C is a chiral carbon atom, n is an integer from one to four, wherein one or more carbon atoms in $(CH_2)_n$ may be substituted by a keto or hydroxy group, m is an integer from one to fourteen, $R_1$ and $R_2$ are independently H, a straight or branched chain alkane or alkene of up to twelve carbon atoms in length —$(CH_2)_m R_5$, or $R_1$ and $R_2$ form a cyclo saturated or unsaturated aromatic ring or substituted aromatic ring having from four to eight carbon atoms and including the nitrogen atom within the ring and $R_3$ is H or $C_{1-3}$, and $R_5$ is a substituted or unsubstituted aryl group wherein the substituted aryl group is mono, di or tri substituted with hydroxy, chloro, fluoro, bromo, or alkoxy ($C_{1-6}$) substituents, or

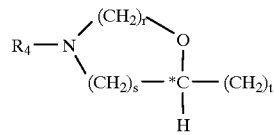

wherein $R_4$ is a hydrogen or a straight or branched chain alkane or alkene of up to eight carbon atoms in length, —$(C_2)_m R_5$, or $R_4$ forms a cyclo saturated or unsaturated aromatic ring or substituted aromatic ring having from four to eight carbon atoms and including the nitrogen atom within the ring, r and s are independently integers from one to four, the sum (r+s) is not greater than five, wherein one or more carbon atoms in $(CH_2)_q$ or $(CH_2)_p$ may be substituted by a keto or hydroxy group, t is an integer from one to fourteen, and $R_5$ is a substituted or unsubstituted aryl group wherein the substituted aryl group is mono, di or tri substituted with hydroxy, chloro, fluoro, bromo, or alkoxy ($C_{1-6}$) substituents, or X is independently hydrogen, $C_{1-6}$ alkyl, a resolved enantiomer ω-1 secondary alcohol-substituted alkyl ($C_{5-8}$) substantially free of the other enantiomer, or a branched —(CH$_2$)$_a$—CHR$_6$—(CH$_2$)$_b$—R$_7$, wherein a is an integer from about 4 to about 12, b is an integer from 0 to 4, R$_6$ is an enantiomer (R or S) or racemic mixture (C$_{1-6}$) alkyl or alkenyl, and R$_7$ is a hydroxy, keto, cyano, chloro, iodo, flouro, or chloro group, with the proviso that at least one X is the resolved ω-1secondary alcohol-substituted alkyl.

3. The method of claim 2 wherein the core moiety of the compound is selected from the group consisting of substituted or unsubstituted barbituric acid, benzamide, glutarimide, homophthalimide, imidazole amide, isocarbostyrile, lumazine, pthalimide, piperidine, pyridine, pyrimidine, pteridine, pyrrole amide, quinazolinedione, quinazolinone, quinolone, recorsinol, succinimide, thymine, triazine, and uracil.

4. The method of claim 2 wherein the core moiety of the compound is selected from the group consisting of methylbarbituric acid, 3,3-dimethylglutarimide, 2-hydroxypyridine, methyldihydroxypyrazolopyrimidine, 1,3-dimethyldihydroxypyrazolo pyrimidine, methylpyrrolopyrimidine, 1-methylpyrrolo pyrimidine, 2-pyrrole amides, 3-pyrrole amides, 1,2,3,4-tetrahydroisoquinolone, 1-methyl-2,4(1H,3H)-quinazolinedione, 1-methylbenzoyleneurea, quinazolin-4(3H)-one; alkyl-substituted (C$_{1-6}$) thymine, methylthymine, alkyl-substituted (C$_{1-6}$) uracil, 6-aminouracil, 1-methyl-5,6-dihydrouracil, 1-methyluracil, 5and/or 6-position substituted uracils, 1-methylthymine, glutarimide, phthalimide, pteridine, 1-methyl-2,4(1H, 3H)-quinazolinedione, homophthalimide, succinimide, 1,3-dihydroxynaphthalene, imidazole amides, piperdine, 2-hydroxypyridine, isocarbostyril, and quinazolin-4(3H)-one.

5. The method of claim 2 wherein the compound is selected from the group consisting of N-(11-octylamino-10-hydroxyundecyl)-homophthalimide, N-(11-octylamino-10-hydroxyundecyl)-2-piperdone, 3-(11-octylamino-10-hydroxyundecyl)-1-methyluracil, 3-(11-octylamino-10-hydroxyundecyl)-1-methyldihydrouracil.

6. The method of claim 1 wherein the core moiety of the compound is selected from the group consisting of substituted or unsubstituted barbituric acid, benzamide, flutarimide, glutarimide, homophthalimide, imidazole amide, isocarbostyrile, lumazine, pthalimide, piperidine, pyridine, pyrimidine, pteridine, pyrrole amide, quinazolinedione, quinazolinone, quinolone, recorsinol, succinimide, thymine, triazine, and uracil.

7. The method of claim 1 wherein the core moiety of the compound is selected from the group consisting of methylbarbituric acid 3,3-dimethylglutarimide, 2-hydroxypyridine, methyldihydroxypyrazolopyrimidine, 1,3-dimethyidihydroxypyrazolo pyrimidine, methylpyrrolopyrimidine, 1-methylpyrrolo pyrimidine, 2-pyrrole amides, 3-pyrrole amides, 1,2,3,4-tetrahydroisoquinolone, 1-methyl-2,4(1H,3H)-quinazolinedione, 1-methylbenzoyleneurea, quinazolin-4(3H)-one; alkyl-substituted (C$_{1-6}$) thymine, methylthymine, alkyl-substituted (C$_{1-6}$) uracil, 6-aminouracil, 1-methyl-5,6-dihydrouracil, 1-methyluracil, 5 and/or 6-position substituted uracils, 1-methylthymine, glutarimide, phthalimide, pteridine, homophthalimide, succinimide, 1,3-dihydroxynaphthalene, imidazole amides, piperdine, 2-hydroxypyridine, isocarbostyril, and quinazolin-4(3H)-one.

8. The method of claim 1 wherein the compound is selected from the group consisting of N-(11-octylamino-10-hydroxyundecyl)-homophthalimide, N-(11-octylamino-10-hydroxyundecyl)-2-piperdone, 3-(11-octylamino-10-hydroxyundecyl)-1-methyluracil, 3-(11-octylamino-10-hydroxyundecyl)-1-methyldihydrouracil.

9. The method of claim 2 wherein the compound is 1-[11-(3,4,5-trimethoxybenzylamino)-10-hydroxyundecyl]-3,7-dimethylxanthine.

10. The method of claim 2 wherein the core moiety is selected from the group consisting of 1,7-dimethylxanthine, 3,7-dimethylxanthine; 3-methylxanthine; 3-methyl-7-methylpivaloylxanthine, 8-amino-3-methylxanthine, 7-methylhypoxanthine, 3,7-dimethylxanthine, 3-methylxanthine, 3-methyl-7-methylpivaloylxanthine, 8-amino-3-methylxanthine, and 7-methylhypoxanthine.

11. The method of claim 1 wherein the compound is selected from the group consisting of R-1-(5-hydroxyhexyl)-3,7-dimethylxanthine, N-(11-octylamino-10-hydroxyundecyl)-3-methylxanthine, 1-(9-decylamino-8-hydroxynonyl)-3,7-dimethylxanthine, 1(9-dodecylamino-8-hydroxynonyl)-3,7-dimethylxanthine, 1-(11-hexylamino-8-hydroxyundecyl)-3,7-dimethylxanthine, N-(11-phenylamino-10-hydroxyundecyl)-3,7-dimethylxanthine, and 1-(9-(2-hydroxydecyl-1-amino)nonyl)-3,7-dimethylxanthine.

12. The method of claim 1 wherein the core moiety is selected from the group consisting of 1,7-dimethylxanthine, 3,7-dimethylxanthine; 3-methylxanthine, 3-methyl-7-methylpivaloylxanthine, 8-amino-3-methylxanthine, 7methylhypoxanthine, 3,7-dimethylxanthine, 3-methylxanthine, 3-methyl-7-methylpivaloylxanthine, 8-amino-3-methylxanthine, and 7-methylhypoxanthine.

13. The method of claim 1 wherein the compound is selected from the group consisting of R-1-(5-hydroxyhexyl)-3,7-dimethylxanthine, N-(11-octylamino-10-hydroxyundecyl)-3-methylxanthine, 1-(9-decylamino-8-hydroxynonyl)-3,7-dimethylxanthine, 1-(9-dodecylamino-8-hydroxynonyl)-3,7-dimethylxanthine, 1-(11-hexylamino-8-hydroxyundecyl)-3,7-dimethylxanthine, N-(11-phenylamino-10-hydroxyundecyl)-3,7-dimethylxanthine, and 1-(9-(2-hydroxydecyl-1-amino)nonyl)-3,7-dimethylxanthine.

* * * * *